(12) United States Patent
Hart et al.

(10) Patent No.: US 7,820,624 B2
(45) Date of Patent: Oct. 26, 2010

(54) PEPTIDE LIGANDS

(75) Inventors: Stephen Lewis Hart, London (GB); Michele Writer, London (GB)

(73) Assignee: ICH Productions Limited, London (GB)

( * ) Notice: Subject to any disclaimer, the term of this patent is extended or adjusted under 35 U.S.C. 154(b) by 1218 days.

(21) Appl. No.: 10/559,758

(22) PCT Filed: Jun. 7, 2004

(86) PCT No.: PCT/GB2004/002421

§ 371 (c)(1),
(2), (4) Date: Mar. 3, 2006

(87) PCT Pub. No.: WO2004/108938

PCT Pub. Date: Dec. 16, 2004

(65) Prior Publication Data

US 2009/0170792 A1   Jul. 2, 2009

(30) Foreign Application Priority Data

Jun. 6, 2003   (GB)   ................................ 0313132.3

(51) Int. Cl.
A61K 38/08   (2006.01)
A61K 48/00   (2006.01)
(52) U.S. Cl. ............................ 514/17; 514/18; 435/455
(58) Field of Classification Search ................ None
See application file for complete search history.

(56) References Cited

U.S. PATENT DOCUMENTS 5,976,787 A * 11/1999 Velicer et al. .................. 435/5
2008/0234183 A1 * 9/2008 Hallbrink et al. .............. 514/12

FOREIGN PATENT DOCUMENTS

| DE | 198 45 251 | 3/2000 |
| WO | WO 91/18010 | 11/1991 |
| WO | WO 9704105 A1 * | 2/1997 |
| WO | WO 98/44121 | 10/1998 |
| WO | WO 98/54347 | 12/1998 |
| WO | WO 0112816 A1 * | 2/2001 |
| WO | WO 01/58940 | 8/2001 |
| WO | WO 02/057445 | 7/2002 |
| WO | WO 02/057447 | 7/2002 |
| WO | WO 02/072616 | 9/2002 |
| WO | WO 03/004646 | 1/2003 |
| WO | WO 03/008537 | 1/2003 |
| WO | WO 03/094974 | 11/2003 |
| WO | WO 03/008537 | 12/2003 |

OTHER PUBLICATIONS

Office Action, dated Jan. 20, 2010, issued in European patent application No. 04 736 220.7.

Bachman et al., "Integrin receptor-targeted transfer peptides for efficient delivery of antisense oligodeoxynucleotides", *J. Mol. Med.*, 76(2): 126-132 (1998).

Bandyopadhyay, "Nucleotide exchange in genomic DNA of rat hepatocytes using RNA/DNA oligonucleotides. Targeted delivery of liposomes and polyethyleneimine to the asialoglycoprotein receptor", *J. Biol. Chem.*, 274(15): 10163-10172 (1999).

Bettinger et al., "Size reduction of galactosylated PEI/DNA complexes improves lectin-mediated gene transfer into hepaotcytes", *Bioconjugate Chem.* 10(4): 558-561 (1999).

Boer et al., "Design and synthesis of potent and selective alpha(4)beta(7) integrin antagonists", *J. Med. Chem.*, 44(16): 2586-2592 (2001).

Brandao et al., "CD40-targeted adenoviral gene transfer to dendritic cells through the use of a novel bispecific single-chain Fv antibody enhances cytotoxic T cell activation", *Vaccine*, 21(19-20): 2268-2272 (2003).

Boussif et al., "A versatile vector for gene and oligonucleotide transfer into cells in culture and in vivo: polyethylenimine" *Proc. Natl. Acad. Sci. USA*, 92(16): 7297-7301 (1995).

Castilho et al., "An integrated process for mammalian cell perfusion cultivation and product purification using a dynamic filter", *Biotechnol. Prog.*, 18(4): 776-781 (2002).

Chowdhury et al., "Fate of DNA targeted to the liver by asialoglycoprotein receptor-mediated endocytosis in vivo. Prolonged persistence in cytoplasmic vesicles after partial hepatectomy", *J. Biol.Chem.*, 268(15): 11265-11271 (1993).

Cole-Strauss et al., "Correction of the mutation responsible for sickle cell anemia by an RNA-DNA oligonucleotide", *Science*, 273(5280): 1386-1389 (1996).

Cruz et al., "Process development of a recombinant antibody/interleukin-2 fusion protein expressed in protein-free medium by BHK cells", *J. Biotechnol.*, 96(2): 169-183 (2002).

Curiel et al., "Adenovirus enhancement of transferring-polylysine-mediated gene delivery", *Proc. Natl. Acad. Sci. USA*, 88(19): 8850-8854 (1991).

Durocher et al., "High-level and high-throughput recombinant protein production by transient transfection of suspension-growing human 293-EBNA1 cells", *Nucleic Acids Res.*, 30(2): E9 (2002).

(Continued)

*Primary Examiner*—Christina Bradley
(74) *Attorney, Agent, or Firm*—Leon R. Yankwich; David G. O'Brien; Yankwich & Associates, PC

(57) ABSTRACT

A peptide consisting of or comprising an amino acid sequence selected from a) $PX^1X^2X^3T$ [SEQ.ID.NO.:1];
b) $PSX^4S$ [SEQ.ID.NO.:2];
c) $QX^5X^6X^7Q$ [SEQ.ID.NO.:3];
d) $SX^8S$ [SEQ.ID.NO.:4], in which $X^1$, $X^2$ and $X^3$, which may be the same or different, each represents an amino acid residue;
$X^4$ represents an amino acid residue; and
$X^5$ and $X^7$, which may be the same or different, each represents an amino acid residue, $X^6$ represents an amino acid residue having an amide side chain; and
$X^8$ represent an amino acid having an aliphatic side chain, which peptide binds to dendritic cells and also to other types of cells. The peptide may be used a target non-viral and viral vectors to such cells.

15 Claims, 19 Drawing Sheets

OTHER PUBLICATIONS

Ehsan et al., "Long-term stabilization of vein graft wall architecture and prolonged resistance to experimental atherosclerosis after E2F decoy oligonucleotide gene therapy", *J. Thorac. Cardiovasc. Surg.*, 121(4): 714-722 (2001).

Ehsan et al., "Endothelial healing in vein grafts: proliferative burst unimpaired by genetic therapy of neointimal disease", *Circulation*, 105(14): 1686-1692 (2002).

Erbacher et al., "Gene transfer with synthetic virus-like particles via the integrin-mediated endocytosis pathway", *Gene Therapy*, 6(1): 138-145 (1999).

Felgner et al., "Nomenclature for synthetic gene delivery systems", *Hum. Gene Ther.*, 8(5): 511-512 (1997).

Goncz et al., "Targeted replacement of normal and mutant CFTR sequences in human airway epithelial cells using DNA fragments", *Hum. Mol. Genet.*, 7(12): 1913-1919 (1998).

Groth et al., "A phage integrase directs efficient site-specific integration in human cells", *Proc. Natl. Acad. Sci. USA*, 97(11): 5995-6000 (2000).

Han et al., "Receptor-mediated gene transfer to cells of hepatic origin by galactosylated albumin-polylysine complexes", *Biol. Pharm. Bull.*, 22(8): 836-840 (1999).

Ivanenkov et al., "Targeted delivery of multivalent phage display vectors into mammalian cells", *Biochimica et Biophysica Acta*, 1448(3): 463-472 (1999).

Knudsen et al., "Application of peptide nucleic acid in cancer therapy", *Anti-cancer Drugs*, 8(2): 113-118 (1997).

Kren et al., "In vivo site-directed mutagenesis of the factor IX gene by chimeric RNA/DNA oligonucleotides", *Nat. Med.*, 4(3): 285-290 (1998).

Krieg et al., "CpG motifs in bacterial DNA trigger direct B-cell activation", *Nature*, 374(6522): 546-549 (1995).

Mann et al., "Ex-vivo gene therapy of human vascular bypass grafts with E2F decoy: the Prevent single-centre, randomized, controlled trial", *Lancet*, 354(9189): 1493-1498 (1999).

Mannion et al., "Sustained reduction of neointima with c-myc antisense oligonucleotides in saphenous vein grafts", *Ann. Thorac. Surg.*, 66(6): 1948-1952 (1998).

Morishita et al., "A gene therapy strategy using a transcription factor decoy of the E2F binding site inhibits smooth muscle proliferation in vivo", *Proc. Natl. Acad. Sci. USA*, 92(13): 5855-5859 (1995).

Nicklin et al., "Ablating adenovirus type 5 fiber-CAR binding and HI loop insertion of the SIGYPLP peptide generate an endothelial cell-selective adenovirus", *Mol. Ther.*, 4(6): 534-542 (2001).

Olivares et al., "Phage R4 integrase mediates site-specific integration in human cells", *Gene*, 278(1-2): 167-176 (2001).

Pereboev et al., "Coxsackievirus-adenovirus receptor genetically fused to anti-human CD40 scFv enhances adenoviral transduction of dendritic cells", *Gene Ther.*, 9(17): 1189-1193 (2002).

Reddy et al., "Optimization of folate-conjugated liposomal vectors for folate receptor-mediated gene therapy", *J. Pharm. Sci.*, 88(11): 1112-1118 (1999).

Reddy et al., "Enhanced folate receptor mediated gene therapy using a novel pH-sensitive lipid formulation", *J. Controlled Release*, 64(1-3): 27-37 (2000).

Rosenkranz et al., "Receptor-mediated endocytosis and nuclear transport of a transfecting DNA contruct", *Exp. Cell Res.*, 199(2): 323-329 (1992).

Shi Y., "Mammalian RNAi for the masses", *Trends Genet.*, 19(1) 9-12 (2003).

Stoll et al., "Phage TP901-1 site-specific integrase functions in human cells", *J. Bacteriol.*, 184(13): 3657-3663 (2002).

Thyagarajan et al., "Mammalian genomes contain active recombinase recognition sites", *Gene*, 244(1-2): 47-54 (2000).

Thyagarajan et al., "Site-specific genomic integration in mammalian cells mediated by phage phiC31 integrase", *Mol. Cell. Biol.*, 21(12): 3926-3934 (2001).

Tillman et al., "Maturation of dendritic cells accompanies high-efficiency gene transfer by a CD40-targeted adenoviral vector", *J. Immunol.*, 162(11): 6378-6383 (1999).

Wade-Martins et al., "Infectious delivery of a 135-kb LDLR genomic locus leads to regulated complementation of low-density lipoprotein receptor deficiency in human cells", *Molecular Therapy*, 7(5 Pt 1): 604-612 (2003).

Wang et al., "Increasing epithelial junction permeability enhances gene transfer to airway epithelia in vivo", *Am. J. Respir. Cell Mol. Biol.*, 22(2): 129-138 (2000).

Watkins et al., "The 'adenobody' approach to viral targeting: specific and enhanced adenoviral gene delivery", *Gene Ther.*, 4(10): 1004-1012 (1997);.

Wickham et al., "Targeting endothelium for gene therapy via receptors up-regulated during angiogenesis and inflammation", *Cancer Immunol. Immunother.*, 45(3-4): 149-151 (1997).

Woolf et al., "Toward the therapeutic editing of mutated RNA sequences", *Proc. Natl. Acad. Sci. USA*, 92(18): 8298-8302 (1995).

Wu et al., "Receptor-mediated in vitro gene transformation by a soluble DNA carrier system", *J. Biol. Chem.*, 262(10): 4429-4432 (1987).

Wu et al., "Receptor-mediated gene delivery in vivo. Partial correction of genetic analbuminemia in Nagase rats", *J. Biol. Chem.*, 266(22): 14338-14342 (1991).

Yano et al., "Improved gene transfer to neuroblastoma cells by a monoclonal antibody targeting RET, a receptor tyrosine kinase", *Hum. Gene Ther.*, 11(7): 995-1004 (2000).

Yant et al., "Somatic integration and long-term transgene expression in normal and haemophilic mice using a DNA transposon system", *Nat. Genet.*, 25(1): 35-41 (2000).

Yoon et al., "Targeted gene correction of episomal DNA in mammalian cells mediated by a chimeric RNA. DNA oligonucleotide", *Proc. Natl. Acad. Sci. USA*, 93(5): 2071-2076 (1996).

\* cited by examiner

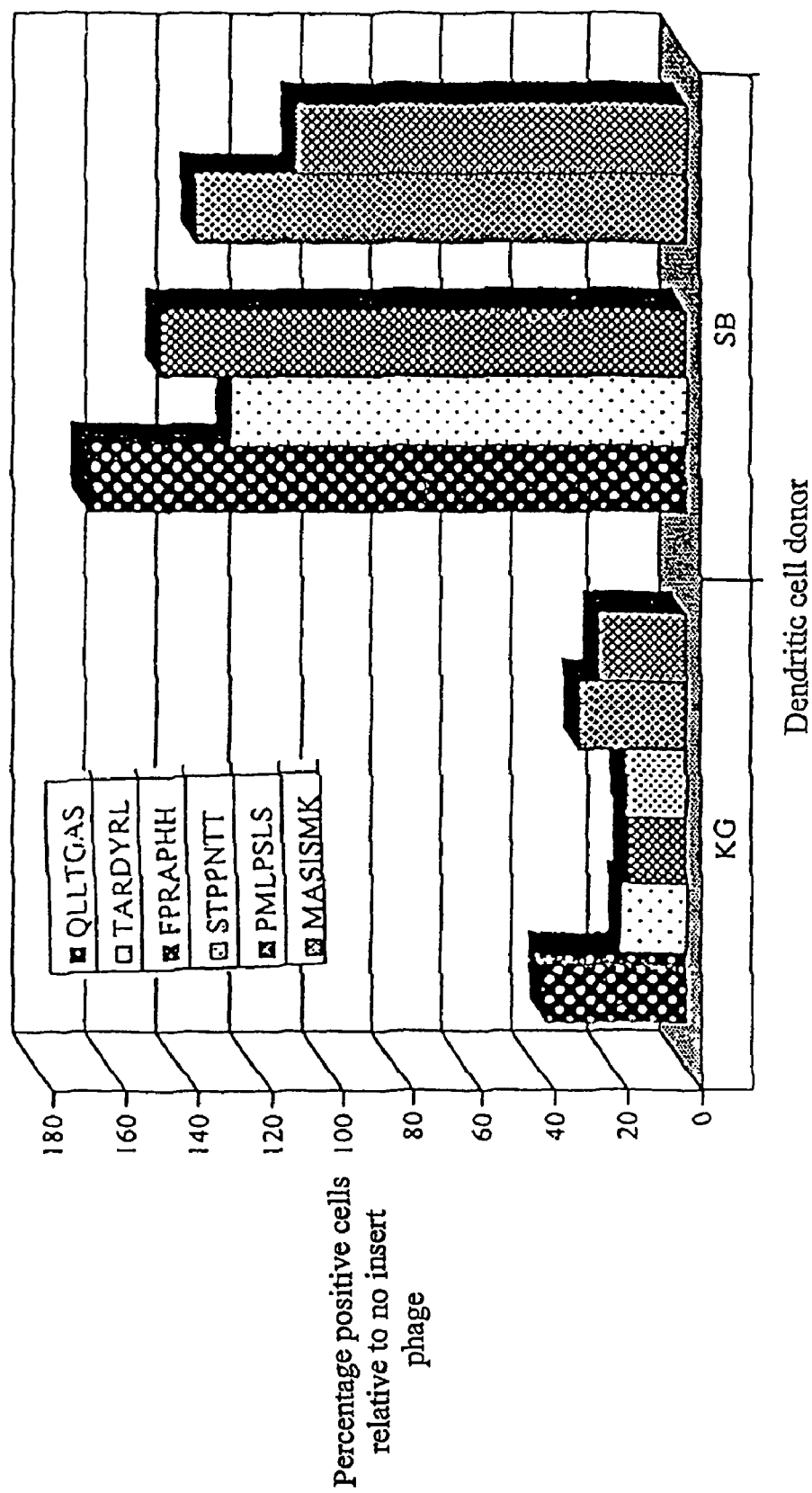

PEPTIDE LIGANDS

This application is a United States national filing under 35 U.S.C.§371 of international (PCT) application No. PCT/GB2004/002421, filed Jun. 7, 2004, designating the US and claiming priority to Great Britain Application No. 0313132.3, filed Jun. 6, 2003.

FIELD OF THE INVENTION

The present invention relates to peptide ligands that bind to dendritic cells, and their use inter alia in vector systems having improved efficiency of gene transfer.

BACKGROUND OF THE INVENTION

Gene therapy and gene vaccination are techniques that offer interesting possibilities for the treatment and/or prophylaxis of a variety of conditions, as does anti-sense therapy. Such techniques require the introduction of a nucleic acid of interest into target cells. The ability to transfer sufficient nucleic acid to specific target cells remains one of the main limitations to the development of gene therapy, anti-sense therapy and gene vaccination. Both viral and non-viral nucleic acid delivery systems have been proposed. The nucleic acid is generally DNA, but in some cases RNA is used.

The term "gene" is used somewhat loosely in the context of gene vaccination and, especially, gene therapy. While, initially, the term "gene" in those contexts was used to denote the coding sequence of a protein, the term is now used in a general sense to refer to a useful nucleic acid. Examples of nucleic acids that can be used in gene therapy and/or in gene vaccination include the coding sequence of a protein and the cDNA copy and genomic version thereof, the latter including introns as well as exons, and also the regulatory upstream and downstream sequences. Other useful nucleic acids include sequences involved in repairing genes and in homologous recombination. These can be molecules such as RNA/DNA chimeras (Bandyopadhyay et al., 1999; Cole-Strauss et al., 1996; Kren et al., 1998; Yoon et al., 1996) or DNA oligonucleotides (Goncz et al., 1998). A useful nucleic acid can be a short sequence contained in a plasmid, or another large nucleic acid encoding an enzyme that mediates integration of plasmids or nucleic acids, for example, the φC31 phage attB/integrase system (Groth et al., 2000; Olivares et al., 2001; Stoll et al., 2002; Thyagarajan et al., 2000; Thyagarajan et al., 2001) and the "Sleeping Beauty" transposon/transposase system (Yant et al., 2000).

DNA oligonucleotides can be delivered for purposes of antisense regulation (Bachmann et al., 1998; Knudsen and Nielsen, 1997; Mannion et al., 1998; Woolf et al., 1995) or as transcription factor decoys (Ehsan et al., 2001; Ehsan et al., 2002; Mann et al., 1999; Morishita et al., 1995). CpG-rich oligonucleotide sequences may be useful as adjuvants to boost vaccine responses (Krieg et al., 1995).

Another important new class of nucleic acids that can be used in gene therapy includes double-stranded RNA 20-30 nt in length known as small interfering RNA molecules (siRNA). RNA interference in mammalian cells has emerged in the last two or three years as an important new approach to the regulation of gene expression, with a high degree of specificity (reviewed Shi 2003). siRNA molecules target homologous regions of mRNA then activate a conserved pathway that leads to degradation of the mRNA target. The precise mechanism of action of siRNA is under intense investigation but it is clear that the application of siRNA to mammalian cells has the potential to revolutionize the field of functional genomics. The ability to simply, effectively, and specifically down-regulate the expression of genes in mammalian cells holds enormous scientific, commercial, and therapeutic potential.

Currently there is no way to predict an effective siRNA target so screening of numerous sequences is performed and numerous potential molecules may have to be screened. Such screening is most conveniently performed with chemically synthesised siRNA molecules delivered by non-viral vectors. Improved vectors for siRNA transfection would thus provide benefits of cost-effectiveness as well as greater functionality. In vivo use of siRNA molecules in animal models is at a much earlier stage of development but there, too, the potential is enormous.

There are two main modes of transfer of nucleic acid into cells, namely, transfer of naked nucleic acid, and vector-mediated transfer. Non-viral or synthetic vectors fall into three main groups, lipid vectors (lipoplex vectors), vectors comprising other non-lipidic cationic polymers including peptides, dendrimers, and polyethylenimine (PEI) (polyplex vectors), and vectors comprising both cationic polymers and lipids (lipopolyplex vectors) (Felgner et al., 1997). Targeted vectors include viral vectors and receptor-targeted synthetic vectors.

Viral vectors commonly used for gene transfer and hence gene therapy and gene vaccination include genetically engineered, replication-defective derivatives of retrovirus, lentivirus, adenovirus, adeno-associated virus (AAV), and herpes simplex virus (HSV). They generally exhibit high efficiency of gene transfer in vitro and in some cases, in vivo, in cell types for the which the virus is trophic, i.e., which contain the native receptors. However, gene transfer is poor in cell types that do not contain a native receptor for the virus. Additionally retroviruses are restricted to transducing cells that are dividing rapidly. Furthermore, most viral vectors are restricted in their packaging capacity for nucleic acids, for example, AAV 5 kb; adenovirus 7-8 kb; 35 kb for helper-dependent adenovirus; and retrovirus 10 kb. HSV can package much larger constructs, up to 135-kb (Wade-Martins et al., 2003). Methods of production of replication deficient viral vectors are generally prolonged procedures and in some cases yields of virus are low.

Receptor-mediated gene delivery is a non-viral method of gene transfer that exploits the physiological cellular process of receptor-mediated endocytosis to internalise the nucleic acid. Examples include vectors targeted against insulin receptors, see for example, Rosenkranz et al Experimental Cell Research 199, 323-329 (1992), asialoglycoprotein receptors, see for example, Wu & Wu, Journal of Biological Chemistry 262, 4429-4432 (1987), Chowdhury et al Journal of Biological Chemistry 268, 11265-11271 (1993), and transferrin receptors, see for example, Ciriel et al, Proc. Natl. Acad. Sci. USA 88, 8850-8854 (1991). Further examples of vectors include monoclonal antibodies that target receptors on neuroblastoma cells (Yano et al, 2000), folate conjugated to liposomes (Reddy & Low 2000, Reddy et al. 1999), galactose for targeting liver cells (Han et al. 1999 Bettinger et al. 1999) and asialogylcoprotein, also for liver cells (Wu et al. 1991).

Receptor-mediated non-viral vectors have several advantages over viral vectors. In particular, they lack pathogenicity; they allow targeted gene delivery to specific cell types and they are not restricted in the size of nucleic acid molecules that can be packaged. Gene expression is achieved only if the nucleic acid component of the transfection complex is released intact from the endosome to the cytoplasm and then crosses the nuclear membrane to access the nuclear transcription machinery. However, transfection efficiency is generally poor relative to viral vectors owing to endosomal degradation of the nucleic acid component, failure of the nucleic acid to enter the nucleus and the exclusion of aggregates larger than about 150 nm from clathrin coated vesicles.

Desirable properties of targeting ligands for vectors are that they should bind to cell-surface receptors with high affinity and specificity and mediate efficient vector internalisation. Short peptides have particular advantages as targeting ligands since they are straightforward to synthesise in high purity and, importantly for in vivo use, they have low immunogenic potential.

WO 98/54347 discloses a mixture comprising an integrin-binding component, a polycationic nucleic acid-binding component, and a lipid component, and also discloses a transfection complex comprising (i) a nucleic acid, especially a nucleic acid encoding a sequence of interest, (ii) an integrin-binding component, (iii) a polycationic nucleic acid-binding component, and (iv) a lipid component.

The transfection complex is primarily an integrin-mediated transfection vector.

It is considered that the components described in WO 98/54347 associate electrostatically to form the vector complex, the vector being of the lipopolyplex type. The vector complexes of WO 98/54347 are found to transfect a range of cell lines and primary cell cultures with high efficiency, with integrin specificity and with low toxicity. For example, vascular smooth muscle cells are transfected with 50% efficiency, endothelial cells with 30% efficiency and haematopoietic cells with 10% efficiency. Furthermore, in vivo transfection of bronchial epithelium of rat lung and pig lung with an efficiency comparable with that of an adenoviral vector has been demonstrated.

Vectors that utilise integrin receptors to mediate gene transfer have the advantage that they target a large number of different types of cells in the body as integrin receptors are relatively widespread. In some circumstances, for example, in in vivo treatment, however, it may be preferable to target recipient cells more specifically.

The dendritic cell is the most potent antigen presenting cell of the immune system and is the only antigen presenting cell capable of stimulating naïve T cell clones, which requires not only recognition of antigenic peptide presented by MHC but also binding costimulatory molecules. The main function of immature dendritic cells is antigen uptake from the surrounding environment. Maturation occurs upon exposure of the cell to danger signals and the function of the cell changes from antigen uptake to peptide presentation on the MHC molecules, combined with trafficking of the dendritic cell to the lymph nodes. Full maturation occurs when the dendritic cells are within the lymph nodes and it is thought that injection or other administration of mature dendritic cells may lead to impairment of homing of the cells.

Transduction or transfection of immature dendritic cells also allows for the introduction of cytokine genes to increase the immune response, whilst also allowing for presentation of peptides taken up from the environment where they have been injected.

Transduction efficiencies to immature dendritic cells using nonviral vectors have been poor, partly due to toxicity. Transfection efficiencies to immature dendritic cells using adenovirus have required high titres of virus, due at least in part to the paucity of the primary adenoviral receptor, the Coxsackie-Adenovirus Receptor (CAR) on the immature dendritic cell surface. Using nonviral vectors, efficiencies have been increased by altering the lipid used. Various strategies have been attempted to increase adenoviral transduction of dendritic cells, including targeting using bispecific antibody fragments (scFv) (Brandao 2003). The use of less adenovirus and a shorter transduction time would be preferable for ex vivo transduction for clinical purposes.

It is an object of the present invention to provide improved vector complexes with enhanced cell targeting properties. The present invention is based on the development of synthetic, targeting non-viral vector complexes that carry a ligand that is more cell-type selective than the ligands of the prior art.

In the development of effective targeting vectors it is useful for several different target-binding ligands to be available. Effective targeted transfection requires not only good targeting but also effective transfer of the vector nucleic acid to the nucleus of the target cell. Even if a ligand is effective in targeting and binding to a target cell, effective gene transfection does not always occur. The reasons for that are, at present, not clear. Accordingly, there remains a degree of unpredictability regarding whether a ligand that binds effectively to a target cell will also bring about effective transfection. It is therefore desirable to have available a "pool" of ligands for any particular cell surface receptor from which an effective transfection ligand may be selected. Such selection may take place by means of a gene transfer assay using, for example, a reporter gene, or by any other suitable means.

SUMMARY OF THE INVENTION

The invention is based on the identification of peptides comprising specific amino acid motifs, which peptides bind to human immature dendritic cells. The identified peptide motifs mediate binding to human dendritic cells and also to other types of cells.

The present invention relates to a peptide having, consisting of or comprising an amino acid sequence selected from
 a) $PX^1X^2X^3T$ [SEQ. ID. NO.:1];
 b) $PSX^4S$ [SEQ. ID. NO.:2];
 c) $QX^5X^6X^7Q$ [SEQ. ID. NO.:3];
 d) $SX^8S$ [SEQ. ID. NO.:4], in which $X^1$, $X^2$ and $X^3$, which may be the same or different, each represents an amino acid residue;

$X^4$ represents an amino acid residue;

$X^5$ and $X^7$, which may be the same or different, each represents an amino acid residue, and $X^6$ represents an amino acid residue having an amide side chain, for example, N or Q.

$X^8$ represents an amino acid residue having an aliphatic side chain, for example, L or I.

The conventional single letter system of abbreviation is used herein to denote amino acids.

The invention provides the use of a peptide of the invention to target an entity that may be a nucleic acid or another molecule, for example, a therapeutically or pharmaceutically active molecule, or a molecule comprising a detectable label to a cell.

The present invention also provides a peptide derivative of the formula A-B-C in which A denotes a peptide of the present invention, B denotes a chemical bond or a spacer element, and C denotes a polycationic nucleic acid binding component.

The present invention further provides a transfection mixture that comprises (i) a lipid component, (ii) a polycationic nucleic acid binding component, and (iii) a peptide of the invention.

The present invention further provides a non-viral transfection complex that comprises (i) a lipid component, (ii) a polycationic nucleic acid binding component, (iii) a peptide of the invention, and (iv) a nucleic acid.

In a transfection mixture or transfection complex of the invention components (ii) and (iii) are preferably in the form of a peptide derivative of the invention.

The invention also provides a viral vector, which vector comprises a peptide of the invention.

In one embodiment, the viral vector is an adenovirus retargeted from its native CAR receptor by incorporation of a peptide of the invention in the adenoviral vector, for example, in the HI region of the fibre protein in the capsid, for example, of adenovirus type 5.

The invention also provides processes for the production of a transfection mixture, a transfection complex, and a viral vector of the invention.

The invention further provides a pharmaceutical composition which comprises a transfection mixture, transfection complex or viral vector of the invention in admixture or conjunction with a pharmaceutically suitable carrier.

The invention further provides a method for the treatment or prophylaxis of a condition caused in a human or in a non-human animal by a defect and/or a deficiency in a gene which comprises administering a transfection complex or a viral vector of the invention the human or to the non-human animal.

The term "a defect and/or a deficiency in a gene" as used herein denotes not only a defect or deficiency in the coding region of a gene, but a defect or deficiency in a control element for the gene, for example, a control element in trans or in cis, or a defect or deficiency in any other element that is involved in the transcription or translation of the gene, whether directly or indirectly.

The invention further provides a method for therapeutic or prophylactic immunisation of a human or of a non-human animal, which comprises administering a transfection complex or a viral vector of the invention comprising an antisense nucleic acid to the human or to the non-human animal.

The invention also provides a method of anti-sense therapy, which comprises administering a transfection complex or a viral vector of the invention to a human or to a non-human animal in which the nucleic acid is a nucleic acid suitable for use in anti-sense therapy.

The invention further provides a transfection complex or a viral vector of the invention for use as a medicament or a vaccine.

The invention also provides the use of a transfection complex or a viral vector of the invention for the manufacture of a medicament for the prophylaxis of a condition caused in a human or a non-human animal by a defect and/or a deficiency in a gene, or for therapeutic or prophylactic immunisation, or for anti-sense therapy.

The invention additionally provides a kit that comprises (i) nucleic acid, (ii) a lipid component, (iii) a polycationic nucleic acid-binding component, and (iv) a peptide of the invention;

a kit that comprises (i) nucleic acid, (iii) a polycationic nucleic acid-binding component, and (iv) a peptide of the invention; and a kit that comprises (ii) a lipid component, (iii) a polycationic nucleic acid-binding component, and (iv) a peptide of the invention.

In a kit of the invention, components (iii) and (iv) are preferably in the form of a peptide derivative of the invention, as described above.

BRIEF DESCRIPTION OF THE FIGURES

FIG. 1 shows binding to day 6 human monocyte-derived immature dendritic cells obtained from donors JD, S and LA. Numbers of phage are shown as plaque forming units (pfu). Sequencing of the bound phage identified peptides APSNSTA [SEQ. ID. NO.:15], QLLTGAS [SEQ. ID. NO.: 30], TARDYRL [SEQ. ID. NO.:31], FQSQYQK [SEQ. ID. NO.:26], PLMPSLS, FPRAPHH [SEQ. ID. NO.:32], MASISMK [SEQ. ID. NO.:27], DWWHTSA [SEQ. ID. NO.: 28], SHVKLNS [SEQ. ID. NO.:29] and SPALKTV [SEQ. ID. NO.:16] and also denotes a phage with no inserted peptide.

FIG. 2 shows binding of phage clones to day 4 human monocyte-derived immature dendritic cells, as measured by fluorescence activate cell sorting (FACS). The percentage cells positive for FITC was measured by FACS analysis.

FIG. 3 shows phage clone binding to day 4 human monocyte-derived immature dendritic cells as measured by FACS. FIG. 3a shows binding to cells from donors KG and SB.

FIG. 4 shows transfection of human monocyte-derived immature dendritic cells using phage-derived targeting peptides in a lipid-peptide-DNA (LID) transfection vector.

FIG. 6 shows transfection and cell death after transfection of day 3 dendritic cells using peptide derivatives A, B, C, D, F and 6 in the same vector system as described in the brief description of FIG. 5.

FIG. 7 shows transfection and cell death after transfection of human peripheral blood monocytes using the LID vector system described in the legend of FIG. 5 with peptide derivatives A, B, C, D, F and 6 and also using no peptide as a control.

DETAILED DESCRIPTION OF THE INVENTION

Figure 1:
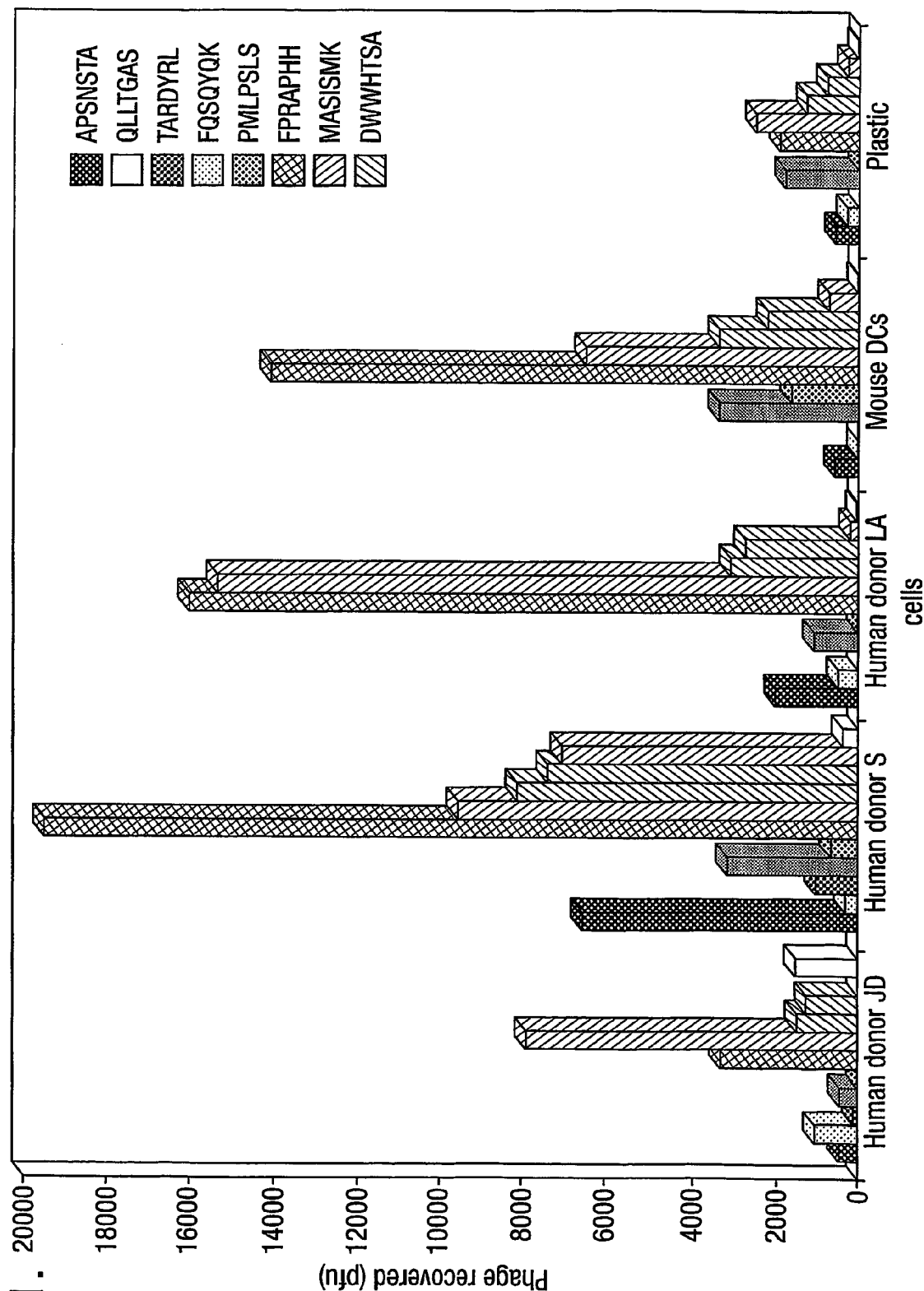
FIG. 1 shows the results of titration of phage clone binding to human and mouse dendritic cells, with binding to plastic as a control.

The invention is based on the identification of peptides comprising specific amino acid motifs, which peptides bind to dendritic cells. The identified peptide motifs mediate binding to human immature monocyte-derived dendritic cells and also to other types of cells, including human primary macrophages, N2a cells (also called Neuro2A cells), a mouse neuroblastoma cell line, HAEo- cells (a human airway epithelial cell line), HepG2 cells (a human hepatocyte cell line) and primary mouse cells, including bone-marrow derived dendritic cells and Sca1+ve mouse stem cells.

The present invention relates to a peptide having, consisting of or comprising an amino acid sequence selected from
a) $PX^1X^2X^3T$ [SEQ. ID. NO.:1];
b) $PSX^4S$ [SEQ. ID. NO.:2];
c) $QX^5X^6X^7Q$ [SEQ. ID. NO.:3];
d) $SX^8S$ [SEQ. ID. NO.:4], in which $X^1$, $X^2$ and $X^3$, which may be the same or different, each represents an amino acid residue;
$X^4$ represents an amino acid residue;
$X^5$ and $X^7$, which may be the same or different, each represents an amino acid residue, and $X^6$ represents an amino acid residue having an amide side chain, for example, N or Q;
$X^8$ represents an amino acid residue having an aliphatic side chain, for example, L or I.

In the aspect of the invention concerning the peptide per se, the invention does not include a peptide comprising an amino acid sequence of SEQ. ID. NO.:1, 2, 3 OR 4, which peptide is a naturally-occurring full length protein.

The conventional single letter system of abbreviation is used herein to denote amino acids. According to that system A denotes (=) alanine, R=arginine, N=asparagine, D=aspartic acid, C=cysteine and cystine, G=glycine, E=glutamic acid, Q=glutamine, H=histidine, I=isoleucine, L=leucine, K=lysine, M=methionine, F=phenylalanine, P=proline, S=serine, T=threonine, W=tryptophan, Y=tyrosine, and V=valine. In this specification, the letter "X" is used to denote any amino acid residue.

In a peptide $PX^1X^2X^3T$ [SEQ. ID. NO.:1] $X^2$ may be, for example, N or L, giving a peptide $PX^N{}_LXT$ [SEQ. ID. NO.:39], which is a recurring motif, see below. $X^1$ may be, for example, S, A or P. $X^3$ may be, for example, S, K or T, or may be A.

A peptide $PX^1X^2X^3T$ [SEQ. ID. NO.:1] in which $X^2$ represents L is a peptide $PX^1LX^3T$ [SEQ. ID. NO.:5]. $X^1$ and $X^3$, which are the same or different, may be as described above. For example, $X^1$ may represent S, A or P, for example, A. $X^3$ may, for example, represent S, K or Y, for example, K. An example of a peptide $PX^1LX^3T$ [SEQ. ID. NO.:5] is peptide PALKT [SEQ. ID. NO.:6].

In a peptide $PX^1X^2X^3T$ [SEQ. ID. NO.:1], $X^2$ may represent N, which peptide is $PX^1NX^3T$ [SEQ. ID. NO.:7], which is a recurring motif, see below. $X^3$ is, for example, S or T, for example, S, giving a peptide $PXN^T\backslash_S T$ [SEQ. ID. NO.:40], which is a recurring motif (see below). $X^1$ and $X^3$ may be the same or different. $X^1$ is, for example, S or P, for example, S. Both $X^1$ and $X^3$ may be S. Examples of a peptide $PX^1NX^3T$ are peptide PSNST [SEQ. ID. NO.:8], and PPNTT [SEQ.ID. NO.:9].

A peptide $PX^1X^2X^3T$ [SEQ. ID. NO.:1] may have, independently, one or more additional residues at the N-terminus and/or at the C-terminus. For example, a peptide $PX^1X^2X^3T$ [SEQ. ID. NO.:1], for example, any of the peptides of SEQ. ID. NO.:1 described above, may also comprise an additional residue. for example, an A or V residue at the C-terminus. Such a peptide has the sequence $PX^1X^2X^3TX^9$ [SEQ. ID. NO.:10] in which $X^9$ represents an amino acid residue, for example, A or V. Examples of such peptides are $PX^1LX^3TX^9$ [SEQ. ID. NO.:11] and $PX^1NX^3TX^9$ [SEQ. ID. NO.:12].

Independently, a peptide $PX^1X^2X^3T$ [SEQ. ID. NO.:1] may have an additional residue at the N-terminus, which peptide has the sequence $X^{10}PX^1X^2X^3T$ [SEQ. ID. No.:13] in which $X^{10}$ represents an amino acid residue, for example, an A, S or T residue.

When an additional residue is present at both the N-terminus and the C-terminus the peptide has the sequence $X^{10}PX^1X^2X^3TX^9$ [SEQ. ID. NO.: 14] in a peptide of $X^{10}PX^1X^2X^3TX^9$ [SEQ. ID. NO.:14], $X^1$, $X^2$, $X^3$, $X^9$ and $X^{10}$ may have the preferred meanings given above.

Examples of peptides of SEQ. ID. NO.:1 having additional residues include APSNSTA [SEQ. ID. NO.:15], SPALKTV [SEQ. ID. NO.:16] and STPPNTT [SEQ. ID. NO.:17]. Variants of such peptides have the N-terminal and/or C-terminal residue omitted.

In a peptide $PSX^4S$ [SEQ. ID. NO.:2], $X^4$ may be, for example, N or L. Examples of peptides of $PSX^4S$ include PSNS [SEQ. ID. NO.:18] and PSLS [SEQ. ID. NO.:19].

A peptide $PSX^4S$ may have, independently, one or more amino acid residues at the N-terminus and/or the C-terminus, for example, an A or L residue at the N-terminus, giving a peptide $X^{11}PSX^4S$ [SEQ. ID. NO.:20] in which $X^{11}$ represents A or L. Such a peptide is $^A\backslash_L PSXS$ [SEQ. ID. NO.:41], which is a recurring motif, see below. In such a peptide $X^4$ may be N or L. Examples of such peptides include APSNS [SEQ. ID. NO.:21] and LPSLS [SEQ. ID. NO.:22].

If desired, one or more further residues may be present at the N-terminus, for example, as in peptides, MLPSLS [SEQ. ID. NO.:23] and PMLPSLS [SEQ. ID. NO.:24].

In a peptide $QX^5X^6X^7Q$ [SEQ. ID. NO.:3], $X^6$ may be an N or Q residue. Such a peptide is $QX^N\backslash_Q XQ$ [SEQ. ID. NO.:42], which is a recurring motif, see below. $X^3$ may be, for example, K or S. $X^5$ may be, for example, P or Y.

A peptide $QX^5X^6X^7Q$ [SEQ. ID. NO.:3] may have, independently, one or more amino acid residues at the N-terminus and/or the C-terminus. A peptide of $QX^5X^6X^7Q$ [SEQ. ID. NO.:3] may have, for example, an N-terminal S or F residue and may have, independently, an M or K residue at the C-terminus. Such peptides include, for example, SQKNPQM [SEQ. ID. NO.25:] and FQSQYQK [SEQ. ID. NO.:26] and variants in which the N- and/or C-terminal residue is omitted.

A further peptide of the invention has the motif $SX^8S$ [SEQ. ID. NO.:4], in which $X^8$ is an amino acid residue having an aliphatic side chain, for example, L or I. Such a peptide is $S^L\backslash_I S$ [SEQ. ID. NO.:43], which is a recurring motif, see below. A peptide $SX^8S$ may have, independently, one or more amino acid residues at the N-terminus and/or the C-terminus. Examples of such peptides include MASISMK [SEQ. ID. NO.:27], and derivatives thereof in which any one or more of the N-terminal and/or C-terminal residues are omitted.

A peptide of the invention may be up to 30 amino acids in length, or may be longer. A peptide of the invention generally has at least about 5 amino acids but may have fewer, for example, as in the case of peptides of SEQ. ID. NOs. 2 and 3. Generally, a peptide of the invention has any number of amino acids from about 6 to about 30 inclusive. The peptide may have 6, 7, 8, 9, 10, 11, 12, 13, 14, 15, 16, 17, 18, 19, 20, 21, 22, 23, 24, 25, 26, 27, 28, 29 or 30 amino acids. Generally, a peptide of the invention may have 25 or fewer amino acids, for example, 20 or fewer, for example 15 or fewer. For example, a peptide of the invention may have 12 amino acids or fewer, for example, 10 amino acids or fewer. Generally, it is preferred for a peptide of the invention to have 5 or more amino acids. For example, a peptide of the invention may have 6 or more amino acids, for example 7 or more amino acids. In the case of a peptide comprising SEQ. ID. NO.:2, the minimum size is 4 amino acids; in the case of a peptide comprising SEQ. ID. NO.:1 the minimum size is 5 amino acids; in the case of a peptide comprising SEQ. ID. NO. 3 the minimum size is 5 amino acids. Generally, for clinical use, it is preferable to use a short peptide to avoid immunogenic reactions.

Generally, the peptides of the invention are 100 or fewer amino acids in length; for example, 50 or fewer amino acids in length, for example, there may be 100 amino acids or fewer, for example, 95 or fewer, for example, 90 or fewer, for example, 85 or fewer, for example, 80 or fewer, for example, 75 or fewer, for example, 70 or fewer, for example, 65 or fewer, for example, 60 or fewer, for example, 55 or fewer, for example, 50 or fewer, for example, 45 or fewer, for example, 40 or fewer, for example, 35 or fewer, for example, 30 or fewer amino acids. Typically, they are of sizes described above.

In so far as any motif or any peptide of the invention occurs in a known naturally-occurring protein, see Example 4, the embodiment of the invention that relates to peptides per se does not include such a known naturally-occurring full-length protein.

A peptide of the invention may comprise a cyclic region. For example, a motif of the invention may be flanked by two or more cysteine residues that are capable of forming one or more disulphide bond(s).

In certain cases it may be desirable that the peptide is larger than described above. A peptide of the invention may be part of a recombinant polypeptide or part of a fusion protein, for example fused to a amino acid sequence that has a desired function, for example, a sequence suitable for use in affinity chromatography. A further example of a fusion protein comprises a peptide of the invention and a viral capsid protein or a region thereof for targeted delivery, or a protein that facilitates peptide display for targeting purposes.

A further fusion protein comprises a peptide of the invention and an antibody against a viral capsid protein or subunits thereof. The antibody component may be of any antibody class, may be an appropriate antigen-binding domain or domains, and may be or be derived from a chimeric or humanised antibody. Such a fusion protein, which may be used in retargeting a viral vector, is part of the present invention.

The peptides of the invention bind to dendritic cells, in particular to human dendritic cells, for example to immature human dendritic cells and mouse dendritic cells. The peptides of the invention may therefore be used to target desired entities to such cells. For example, a peptide of the invention may be used to target a nucleic acid or an antigen to dendritic cells. A peptide of the invention may be used to target a pharmaceutically active substance to dendritic cells.

It is not yet known to which receptor(s) on dendritic cells the peptides of the invention bind. However, we have found that the peptides of the present invention also bind to other cells and other types of cells, including including human primary macrophages, N2a cells (Neuro2A cells, a mouse neuroblastoma cell line), HAEo- cells (a human airway epithelial cell line), HepG2 cells (a human hepatocyte cell line) and primary mouse cells including bone-marrow derived dendritic cells and Sca1+ve mouse stem cells. A peptide of the invention may be used to target entities, for example, nucleic acids, antigens and pharmaceutically active substances, to such cells.

Identification of peptides of the invention and their binding to different cell types may be determined readily, for example, by a phage peptide clone screening assay using either whole cell flow cytometry, for example, FACS, or titration of phage, or by transduction of cells with retargeted adenovirus bearing the peptide of interest. Such assays are described below and in detail in the following Examples.

A peptide of the present invention, for example, a dendritic cell-binding component, may be identified by selection from a peptide library of oligomeric peptides, for example, a library of random peptide oligomers, generally of the same length. While in principle the oligomeric peptides may be of any length, a peptide that is too long may present difficulties of chemical synthesis and may be immunogenic in vivo, while a peptide that is too short may not have any binding domain. Examples of targeting motifs that are generally suitable are those having from about four to about 30 amino acid residues, see above.

In studies that are described in detail in the Examples below, random 7-mers (peptides having seven amino acid residues) displayed on filamentous phage particles were used.

The 7-mer library used was a C7C library i.e. random 7-mer peptides flanked by cysteine residues, obtained from New England Biolabs Inc.

As indicated above, the dendritic cell binding peptides of the invention were identified by selection from a phage display library comprising random peptide sequences seven residues in length flanked by cysteine residues to allow cyclisation. Such selection procedures are generally known. According to such procedures, suspensions of phage are incubated with target cells. Unbound phage are then washed away and, subsequently, bound phage are extracted either by washing the remaining cells with a low pH buffer or by lysing the cells. E. coli are then infected with released phage and a preparation of first round phage is obtained. The cycle is performed repeatedly, for example, three times and, in order to enrich for targeting phage, the stringency conditions may be increased in the later rounds of selection, for example by increasing the number of wash steps, introducing a low pH wash prior to elution, and preselecting with wells coated with medium blocker.

Following selection by successive rounds of phage amplification, we found that phage with high affinity for dendritic cells may be selected further by whole cell flow cytometry and phage titration assays.

The amino acid sequences of clones obtained from cell lysis eluted C7C phage in a first experiment are shown in Table 1.

TABLE 1

Phage sequences obtained from cells lysis of elude phage

| Sequence | Clone frequency (%) | SEQ. ID |
|---|---|---|
| APSNSTA | 21 | 15 |
| DWWHTSA | 20 | 28 |
| SHVKLNS | 12 | 29 |
| SQKNPQM | 7 | 25 |
| QLLTGAS | 6 | 30 |
| SPALKTV | 6 | 16 |
| FQSQYQK | 6 | 26 |
| TARDYRL | 5 | 31 |
| FPRAPHH | 5 | 32 |
| STPPNTT | 4 | 17 |
| PMLPSLS | 1 | 24 |
| SEWLSAL | 1 | 33 |
| IGGIRRH | 1 | 34 |
| YTMEFNR | 1 | 35 |
| MASISMK | 1 | 27 |
| PAAYKAH | 1 | 36 |

Each of the peptides listed above is part of the present invention, as are longer and shorter derivatives thereof, for example, as described above.

Analysis of the 16 binding sequences from the phage clones shown in Table 1 identified four minimal motifs, namely $PX^1X^2X^3T$ [SEQ. ID. NO.:1], $PSX^4S$ [SEQ. ID. NO.:2], $QX^5X^6X^7Q$ [SEQ. ID. NO.:3], and $SX^8S$ [SEQ. ID. NO.:4] which are considered to potentially to play an important role in binding to receptors on dendritic cells. $PX^1X^2X^3T$ [SEQ. ID. NO.:1] comprises several motifs, including $PXXXT^A\backslash_V$ [SEQ. ID. NO.:37], PXNXT [SEQ. ID. NO.:38], $PX^M\backslash_L XT$ [SEQ. ID. NO.:39], and PXNNT [SEQ. ID. NO.:40]. A recurring motif based on $PSX^4S$ [SEQ. ID. NO.:2] is $^A\backslash_L PSXS$ [SEQ. ID. NO.:41], and a recurring motif based on QXXXQ [SEQ. ID. NO.:3] is $QX^M\backslash_Q XQ$ [SEQ. ID. NO.:42]. $S^L\backslash_F S$ [SEQ. ID. NO.:43] is a recurring form of the motif SXS.

Of the clones sequenced, 46% contained one or more of the above motifs, with the most frequent clone, APSNSTA [SEQ. ID. NO.:15], showing a degree of homology to three other peptide sequences, SPALKTV [SEQ. ID. NO.:16], STPPNTT [SEQ. ID. NO.:17] and PMLPSLS [SEQ. ID. NO.:24].

Phage were recovered and titred from each round of phage clone binding to immature dendritic cells. To summarise the procedure, $2 \times 10^{11}$ blocked phage were added to $5 \times 10^4$ blocked monocyte-derived immature dendritic cells for 1 hour on ice before washing cells three times with PBS-0.05% Tween 20, eluting phage with TBS pH5.5, and lysing cells to harvest the phage remaining bound. The numbers of phage harvested by cell lysis were calculated as plaque forming units (pfu). FIG. 1 shows results of some of the titrations. Sequencing of the bound phage shown in FIG. 1 identified the peptides as APSNSTA [SEQ. ID. NO.:15], QLLTGAS [SEQ. ID. NO.:30], TARDYRL [SEQ. ID. NO.:31], FQSQYQK [SEQ. ID. NO.:26], PLMPSLS [SEQ. ID. NO.:24], FPRAPHH [SEQ. ID. NO.:32], MASISMK [SEQ. ID. NO.:27], DWWHTSA [SEQ. ID. NO.:28], SHVKLNS [SEQ. ID. NO.:29], and SPALKTV [SEQ. ID. NO.:16].

Sequencing of 81 phage clones from the cell-associated fraction from the third round of titration of phage clone binding to immature dendritic cells identified 16 different sequences, see Table 2.

TABLE 2

Phage sequences from third round of titration of phage clone binding to dendritic cells

| Sequence | Number of clones | Percentage of clones | SEQ. ID. NO: |
|---|---|---|---|
| APSNSTA | 17 | 21 | 15 |
| DWWHTSA | 16 | 20 | 28 |
| SHVKLNS | 10 | 12 | 29 |
| SQKNPQM | 6 | 7 | 25 |
| QLLTGAS | 5 | 6 | 30 |
| SPALKTV | 5 | 6 | 16 |
| FQSQYQK | 5 | 6 | 26 |
| TARDYRL | 4 | 5 | 31 |
| FPRAPHH | 4 | 5 | 32 |
| STPPNTT | 3 | 4 | 17 |
| PMLPSLS | 1 | 1 | 24 |
| SEWLSAL | 1 | 1 | 33 |
| IGGIRRH | 1 | 1 | 34 |
| YTMEFNR | 1 | 1 | 35 |
| MASISMK | 1 | 1 | 27 |
| PAAYKAH | 1 | 1 | 36 |

The three most frequent phage clones are present at 21% (APSNSTA) [SEQ. ID. NO.:15], 20% (DWWHTSA) [SEQ. ID. NO.:28] and 12% (SHVKLNS) [SEQ. ID. NO.:29], with the remainder present at 7% and below. Analysis of the 16 binding sequences from the phage clones identified five minimal motifs, namely, $PXN^T/_S T$ [SEQ. ID. NO.:40], $PXXXT^A/_V$ [SEQ. ID. NO.:37], $^A/_L PSXS$ [SEQ. ID. NO.:41], $S^L/_I S$ [SEQ. ID. NO.:43], and $QX^N/_Q XQ$ [SEQ. ID. NO.:42], see Table 3, which motifs may play an important role in binding to receptors on dendritic cells. Of all the clones sequenced, 46% contained one or more motifs, with the most frequent clone, APSNSTA [SEQ. ID. NO.:15], showing a degree of homology to three other peptide sequences, see Table 3.

TABLE 3

Conserved amino acid motifs in peptide sequences

| Peptide Homology | Motif | % clones containing motif |
|---|---|---|
| A*PS*NS*TA* [SEQ. ID. NO.:15] S*PALKTV* [SEQ. ID. NO.:16] | $PXXXT^A/_V$ [SEQ. ID. NO.:37] | 27 |
| ST*PP*N*TT* [SEQ. ID. NO.:32] A*PS*NS*TA* [SEQ. ID. NO.:15] | PXNXT [SEQ. ID. NO.:40] | 25 |
| ST*PP*N*TT* [SEQ. ID. NO.:32] A*PS*NS*TA* [SEQ. ID. NO.:15] S*PALKTV* [SEQ. ID. NO.:16] | $PX^N/_L XT$ [SEQ. ID. NO.:39] | 31 |
| A*PS*NS*TA* [SEQ. ID. NO.:15] PM*LPSLS* [SEQ. ID. NO.:24] | $^A/_L PSXS$ [SEQ. ID. NO.:41] | 22 |
| S*Q*K*NPQ*M [SEQ. ID. NO.:25] F*Q*SQY*Q*K [SEQ. ID. NO.:26] | $QX^N/_Q XQ$ [SEQ. ID. NO.:42] | 13 |
| PML*PSLS* [SEQ. ID. NO.:24] MA*SIS*MK [SEQ. ID. NO.:27] | $S^L/_I S$ [SEQ. ID. NO.:43] | 2 |

Identical amino acids are shown in bold and italic
Similar amino acids are shown in italic Titrations of phage clone binding to dendritic cells in most cases showed that the clones having peptide inserts bind to a greater extent to the cells than do phage that have no insert in the cells. Two clones, FPRAPHH [SEQ. ID. NO.:32] and MASISMK [SEQ. ID. NO.:27] bound in highest numbers in all titrations, including the titration of phage binding to mouse dendritic cells. The numbers of phage binding to plastic were low for all clones tested, suggesting that phage binding demonstrated by high titres in these experiments is due to binding to cells and not background non-specific binding to the wells or blocking molecules.

Figure 2A:
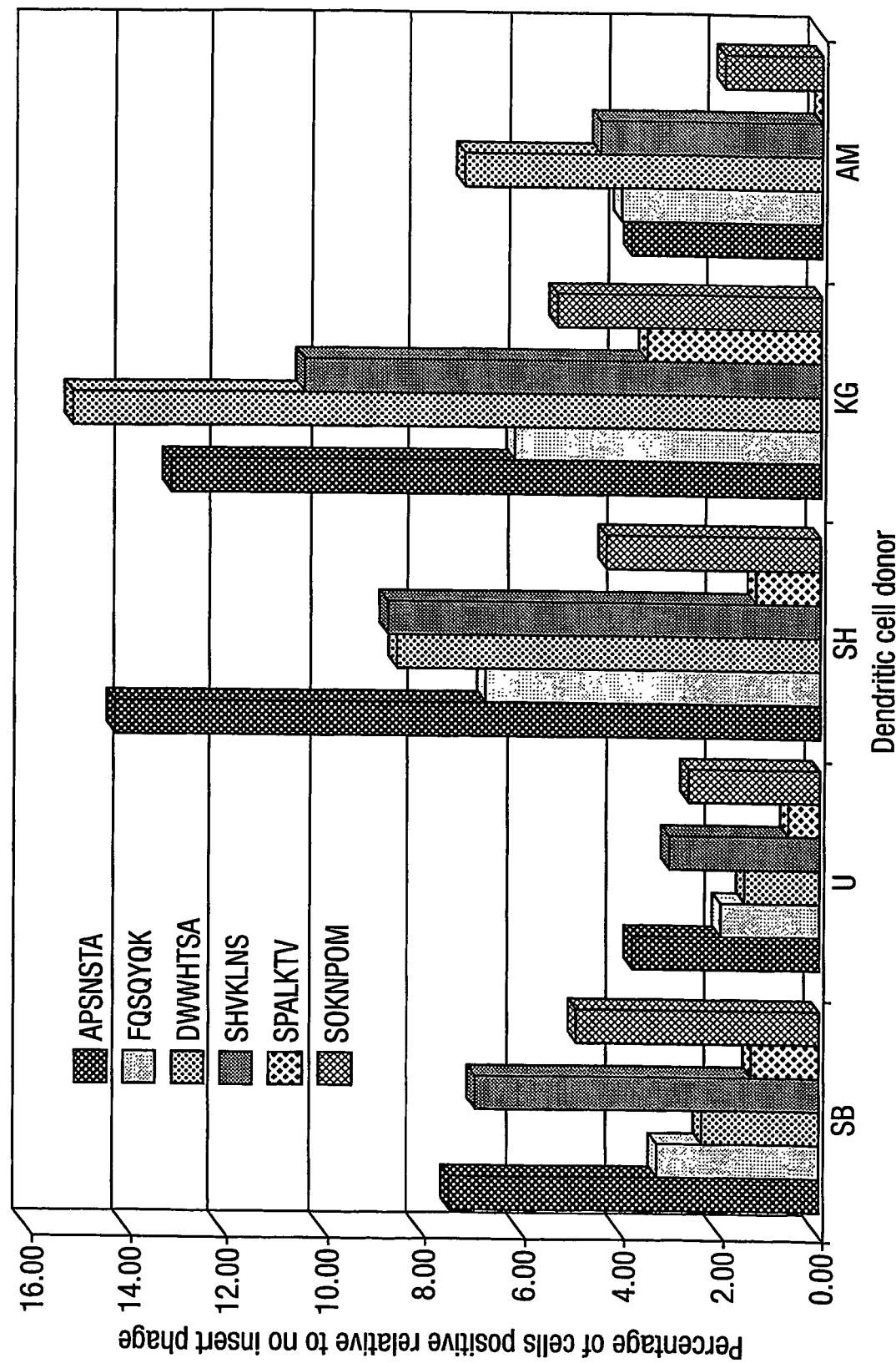
FIG. 2a shows binding to cells from donors SB, U, SH, KG and AM.
Figure 2B:
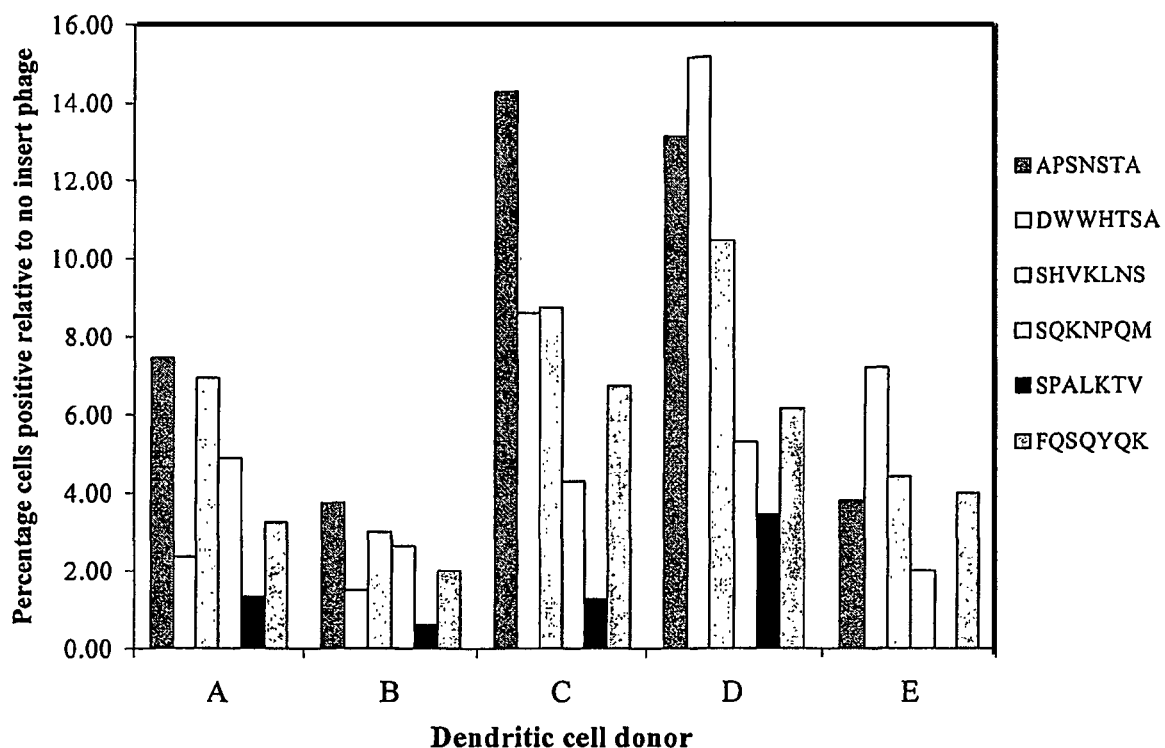
FIG. 2b shows binding to cells from donors A to E. In both cases, sequencing of the bound phage identified peptides APSNSTA [SEQ. ID. NO.:15], FQSQYQK [SEQ. ID. NO.: 26], DWWHTSA [SEQ. ID. NO.:28], SHVKLNS [SEQ. ID. NO.:29], SPALKTV [SEQ. ID. NO.:16] and, SQKNPQM [SEQ. ID. NO.: 25].

FACS analysis of phage binding to dendritic cells from five different dendritic cell donors with six of the most frequent clones namely APSNSTA [SEQ. ID. NO.:17], FQSQYQK [SEQ. ID. NO.:26], DWWHTSA [SEQ. ID. NO.:28], SHVKLNS [SEQ. ID. NO.:29], SPALKTV [SEQ. ID. NO.:16], and SQKNPQM [SEQ. ID. NO.:25] showed that all clones except for one, SPALKTV [SEQ. ID. NO.:16], were detected binding to a higher percentage of cells than a phage clone bearing no insert, see FIG. 2.

Figure 3B:
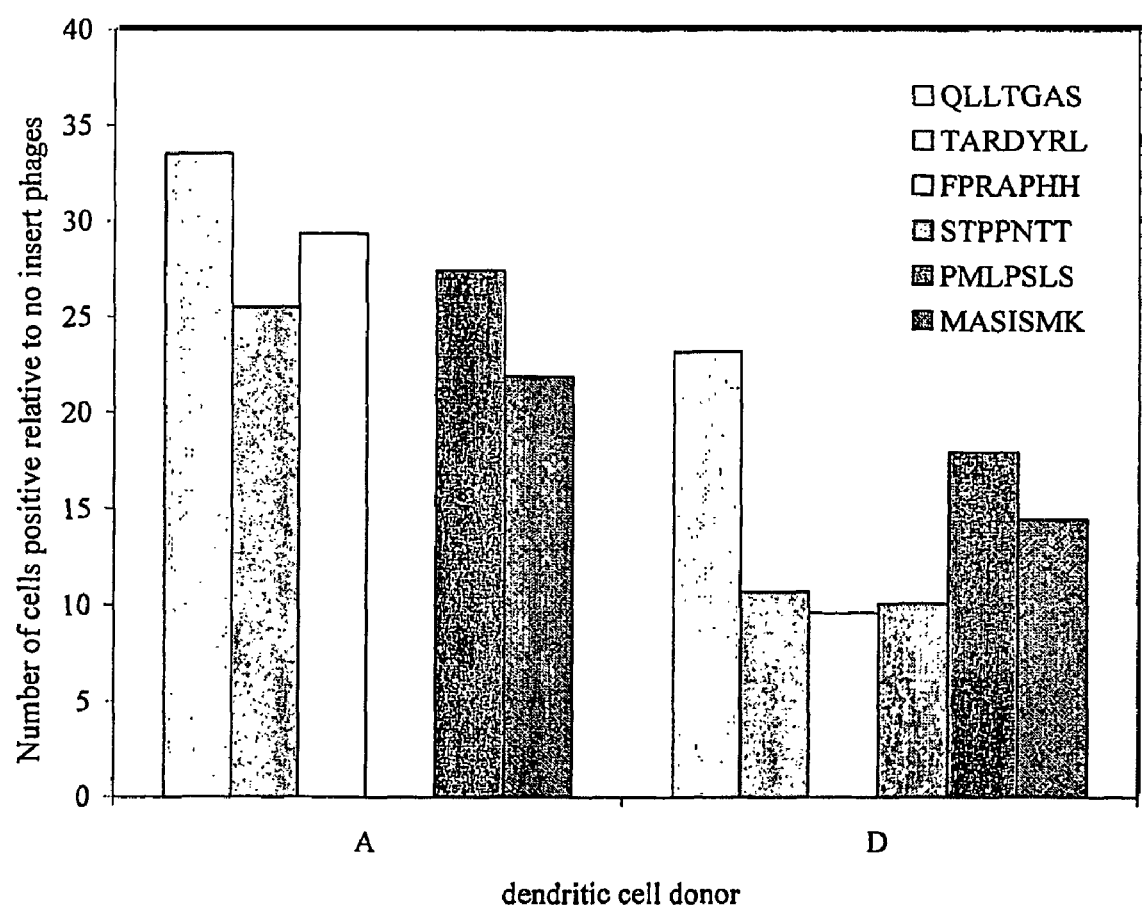
FIG. 3b shows binding to cells of donors A and B. In both cases subsequent sequencing of the bound phage identified peptides QLLTGAS [SEQ. ID. NO.:30], TARDYRL [SEQ. ID. NO.:31], PLMPSLS [SEQ. ID. NO.:24], FPRAPHH [SEQ. ID. NO.:32], MASISMK [SEQ. ID. NO.:27], STPPNTT [SEQ. ID. NO.:17].

The pattern of binding identified the three clones that bind to dendritic cells in highest amounts as those containing the peptides APSNSTA [SEQ. ID. NO.:17], DWWHTSA [SEQ. ID. NO.:28] and SHVKLNS [SEQ. ID. NO.:29], which were also the three most frequently isolated from the selection. For the second set of six clones tested, namely those containing the peptides QLLTGAS [SEQ. ID. NO.:30], TARDYRL [SEQ. ID. NO.:31], PMLPSLS [SEQ. ID. NO.:24], FPRAPHH [SEQ. ID. NO.:32], MASISMK [SEQ. ID. NO.:27], and STPPNTT [SEQ. ID. NO.: 32], all clones showed a higher percentage of cells positive for bound phage than the controls with no insert. QLLTGAS [SEQ. ID. NO.:30] binds to marginally more cells than the others, see FIG. 3.

Of the 16 phage sequences five, namely SHVKLNS [SEQ. ID. NO.:29] (peptide A), APSNSTA [SEQ. ID. NO.:15] (peptide B), MASISMK [SEQ. ID. NO.:27] (peptide C), FPRAHH [SEQ. ID. NO.:32] (peptide D), and DWWHTSA [SEQ. ID. NO.:28] (peptide F). were chosen for synthesis on the basis that they were amongst the most frequent clones and also were among the top binders in the FACS assay of phage clone binding.

From the Tables it may be seen that motifs were present in several of the clones. This strongly suggests that those motifs are important for dendritic cell binding. It is at present not known to which dendritic cell receptor(s) the sequences bind. The various motifs may target the same receptor or they may target different receptors on dendritic cells. The receptor(s) also occur on other cells, see below.

Good binding indicates a high affinity interaction and/or the binding of a cell surface receptor molecule present in high numbers on the cell surface.

Figure 4A:
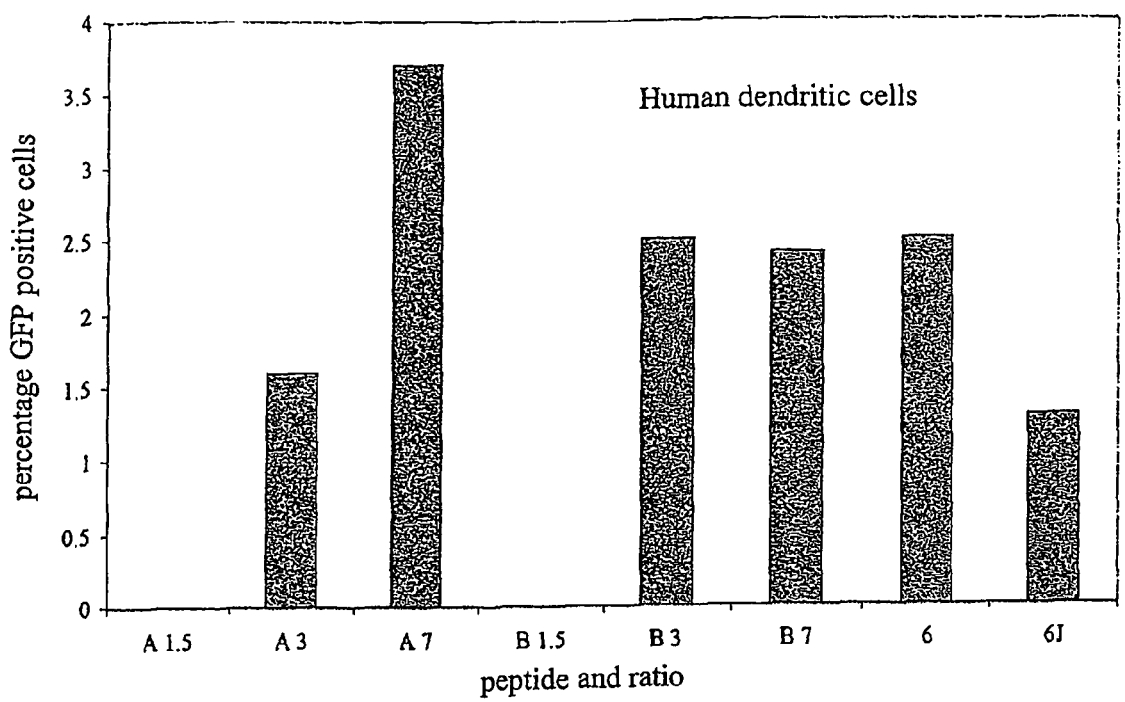
FIG. 4a shows transfection of day 6 human monocyte-derived dendritic cells with phage derived peptide A derivative ([K]$_{16}$-GACSHVKLNSCG) [SEQ. ID. NO.:44], peptide B derivative ([K]$_{16}$-GACAPSNSTACG) [SEQ. ID. NO.:45], peptide 6 derivative [K]$_{16}$-GACRREEWACG) [SEQ. ID. NO.:51] or the scrambled control peptide 6J ([K]$_{16}$-GAC-ATRWARECG) [SEQ. ID. NO.:50]. Peptide A and B derivatives are used in a transfection complex in a ratio to phage DNA of 1.5:1 (A1.5, B1.5) 3:1 (A3, B3), and 7:1 (A7, B7). Controls include cells with no transfection complexes added (OptiMEM only), and also cells transfected with peptide 6 derivative and peptide 6J, its scrambled control both at 3:1 ratio of peptide:DNA. Each result is the percentage GFP positive cells from 3 pooled transfection reactions.

The peptides A to F were synthesized in a constrained form with a DNA-binding $[K]_{16}$ domain, a GAC (inter and a C-terminal CG group. The peptides derivatives were tested for their ability to transfect immature dendritic cells in a transfection complex with DNA and lipid (an "LID" or "lipopolyplex" vector, L denoting lipid, I denoting peptide derivative and D denoting nucleic acid). The results are shown in FIG. 4.

Transfection efficiency in day 6 cells, as measured in non-optimised experiments by the percentage of cells positive for the reporter gene EGFP determined by FACS, was increased by the use of the phage-derived peptide A (SHVKLNS) [SEQ. ID. NO.:29] to a level approximately one and a half times that of the positive control, peptide 6, which is an integrin binding peptide RRETAWA [SEQ. ID. NO.:53] and the negative control, peptide 6J, (a scrambled version of peptide 6). Peptide B (APSNSTA) [SEQ. ID. NO.:15] produced transfection levels equal to those of peptide 6, see FIG. 4a. Optimisation in conditions for a particular peptide may result in improved transfection efficiencies. The percentage of cells transfected did not reach 5%, possibly due to the toxic effect of the transfection procedure on the dendritic cells.

Figure 4B:
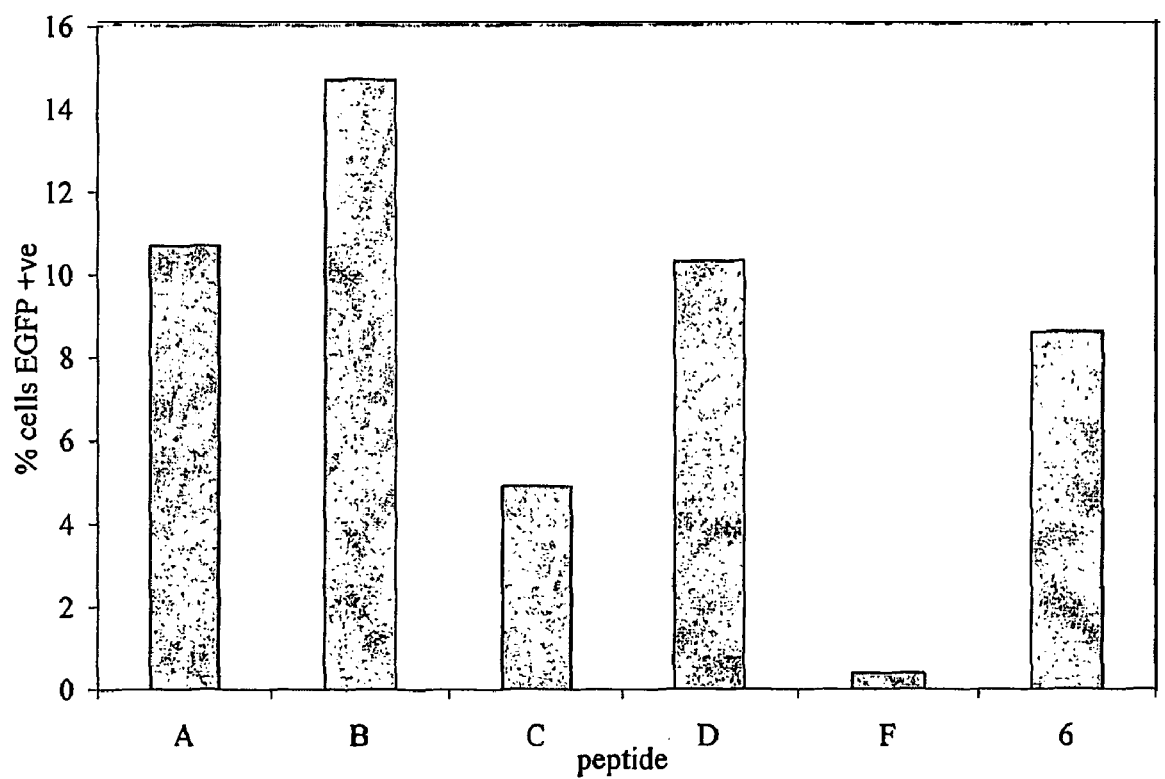
FIG. 4b shows the results of transfection of day 4 human monocyte-derived dendritic cells with phage derived peptides A, B, C ([K])₁₆-GACMASISMKCQ) [SEQ. ID. NO.:52], D ([K]₁₆-GACFPRAPHHCG) [SEQ. ID. NO.:47] and F ([K]₁₆-GACDWWHTSACG) [SEQ. ID. NO.:48].

A comparison of transfection efficiencies of all five peptides synthesised derivates A, B, C, D and F in the LID format using lipofectin and transfecting day 4 dendritic cells, identified peptides A, B and D as giving the best transfection efficiencies, all transfecting over 10% of dendritic cells, with peptide C giving approximately half that value, and peptide F performing poorly, with less than 1% of cells transfected, see FIG. 4b.

Transfection efficiency, as measured by the percentage cells positive for the reporter gene EGFP determined by FACS, was increased by the use of the phage derived peptide A (SHVKLNS) [SEQ. ID. NO.:29] to a level approximately one and a half times that of the positive control, peptide 6, the integrin binding peptide RRETAWA [SEQ. ID. NO.:53] and the negative control, peptide 6J, (the scrambled version of peptide 6). Peptide B (APSNSTA) [SEQ. ID. NO.:15] produced transfection levels equal to those of peptide 6. The percentage of cells transfected did not reach 5%, possibly due to the toxic effect of the transfection procedure on the dendritic cells.

Figure 5A:
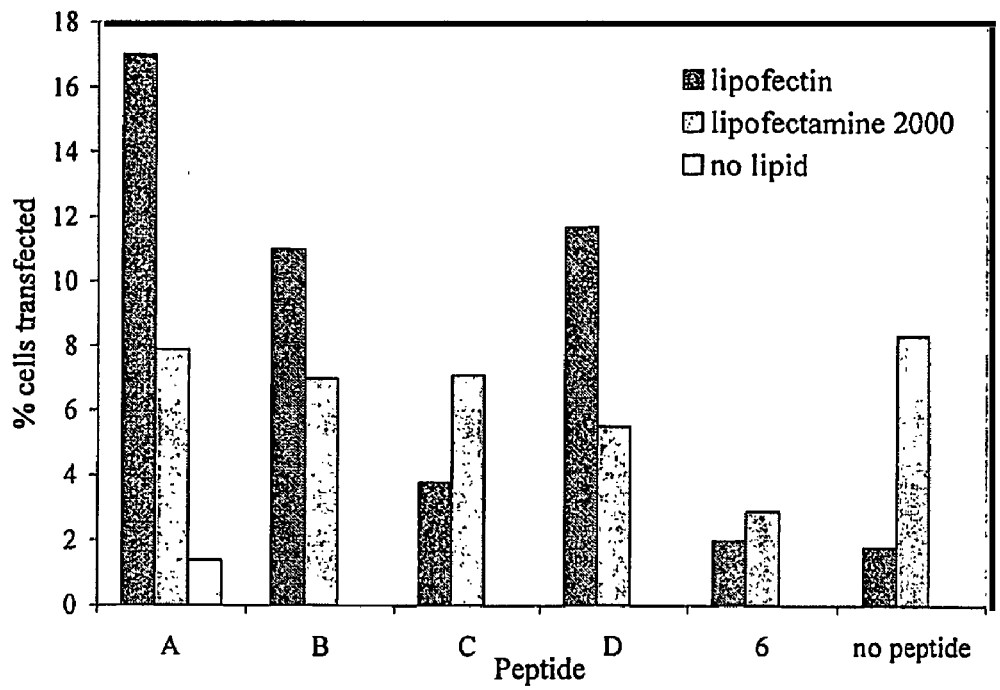
FIG. 5 shows transfection and cell death after transfection of day 4 human immature monocyte-derived dendritic cells using a lipid-peptide-DNA (LID) transfection vector (see legend to FIG. 4). Peptide derivatives A, B, C, D and 6 were used, with a vector containing no peptide as a control. Vectors containing lipofectin or lipofectamine 2000 as lipid were used, and a vector containing peptide derivative A and no lipid was also used as a control. The lipid:DNA ratio was 0.75:1 by weight. All peptide:DNA charge ratios were 7:1.
FIG. 5b shows cell death following transfection using the vectors of FIG. 5a. Cell death was measured by retention of 7AAD measured by flow cytometry 24 hours following transfection.

The four constrained peptides A, B, C and D synthesised with a DNA-binding $[K]_{16}$ [SEQ. ID. NO.: 54] domain, were tested for their ability to transfect day 4 immature dendritic cells in a lipopolyplex (LID) transfection comprising commercially available lipids Lipofectin and Lipofectamine, see FIG. 5a. Where lipofectin was used, all peptides produced transfection efficiencies above that of peptide 6 (an integrin binding peptide). Peptide A produced the highest efficiency of 17%, with peptides B and D giving 11% positive cells, C producing about 7% positive, only just above the 2% achieved with peptide 6 and no peptide control. Where no lipid was used, transfection was less than 1% for peptide A, demonstrating the importance of the lipid for the efficacy of the complex.

Figure 5B:
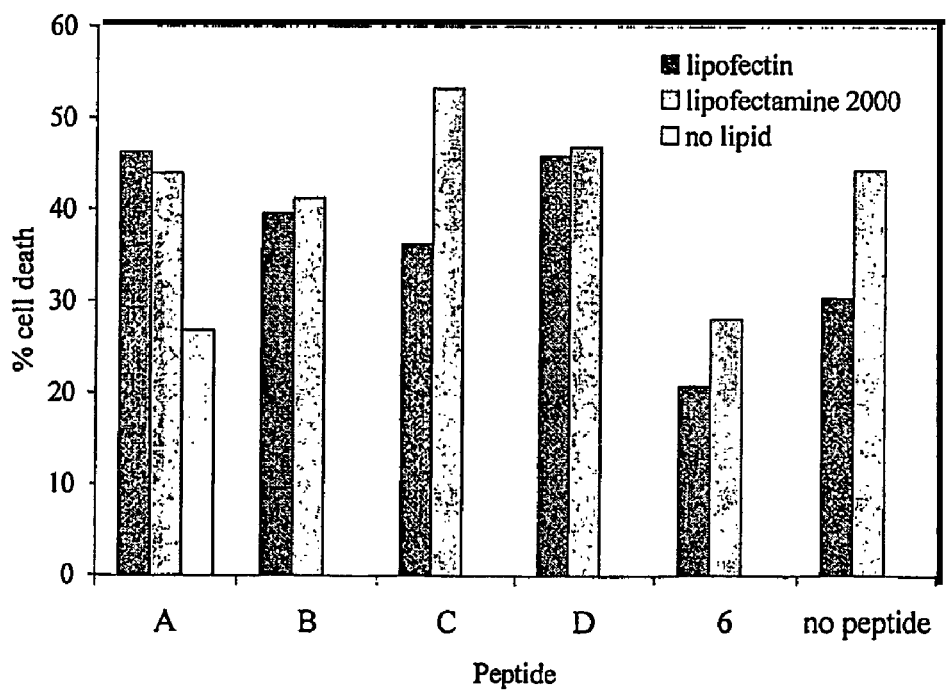

Lipofectamine 2000 produced generally lower transfection efficiencies than lipofectin, between 5 and 8%, except for peptide 6, which provided 3% positive cells. Toxicity was high in all cases, see FIG. 5b, at between 40 and 53%, with the lipofectin giving similar levels of toxicity to Lipofectamine 2000, except in the case of peptide C and no peptide, where lipofectamine 2000 is noticeably more toxic than Lipofectin. This toxicity can vary between experiments, with Lipofectin resulting in cell death in the range 17 to 46%, and lipofectamine 2000 in the range 26 to 53%. When metafetene was used in accordance with the manufacturers' instructions, a much higher level of cell death was seen, between 78 and 84%, data not shown, suggesting choice of lipid can seriously affect cell death following transfection.

Figure 6A:
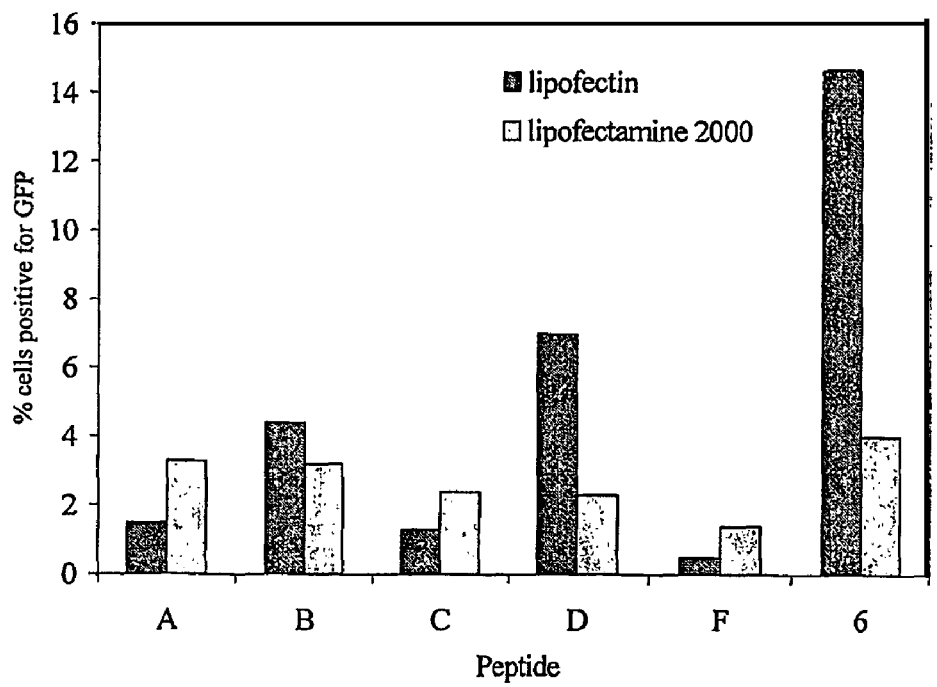
FIG. 6a shows transfection efficiency.
Figure 6B:
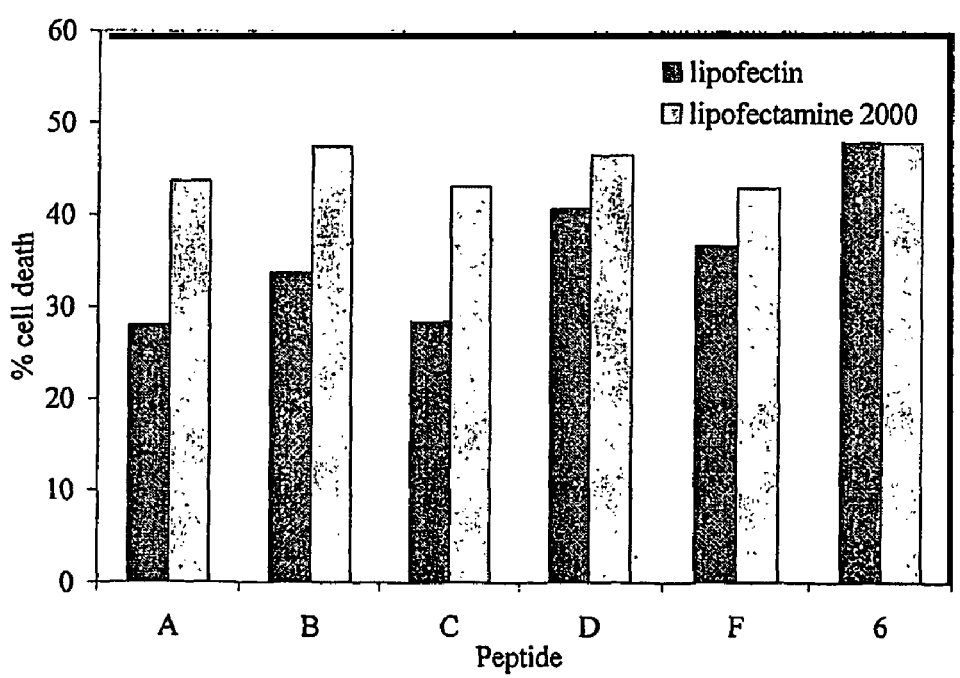
FIG. 6b shows cell death.

Transfection efficiencies of day 3 dendritic cells were considerably lower than day 4 dendritic cells, at 7% EGFP positive cells and lower, except for the control, peptide 6 which gave an efficiency of 14%, see FIG. 6a. Cell death was high in all samples, at between 28 and 48%, with Lipofectin being slightly less toxic than Lipofectamine 2000, see FIG. 6b.

Figure 7A:
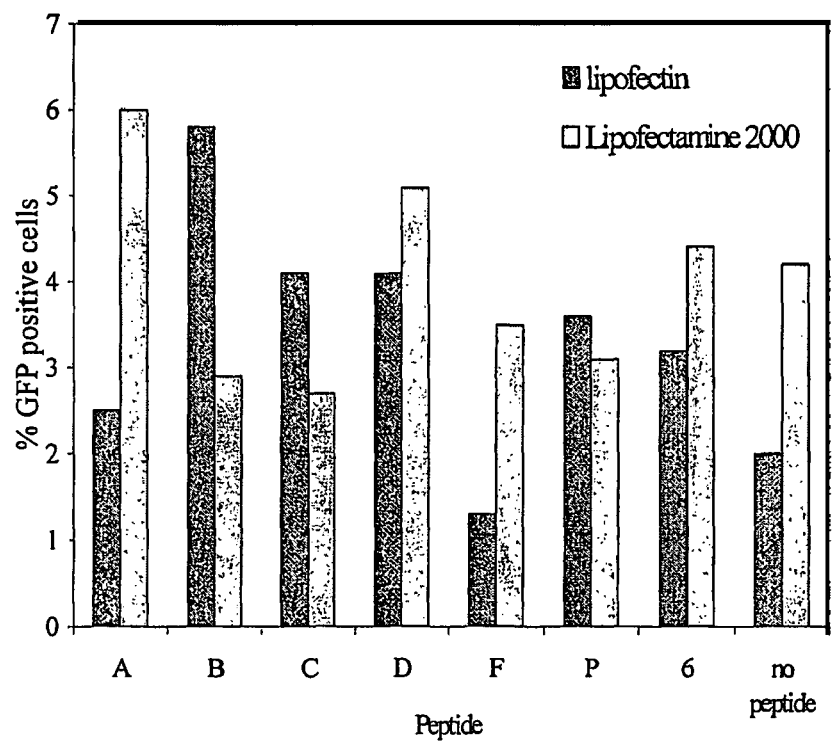
FIG. 7a shows transfection efficiency.
Figure 7B:
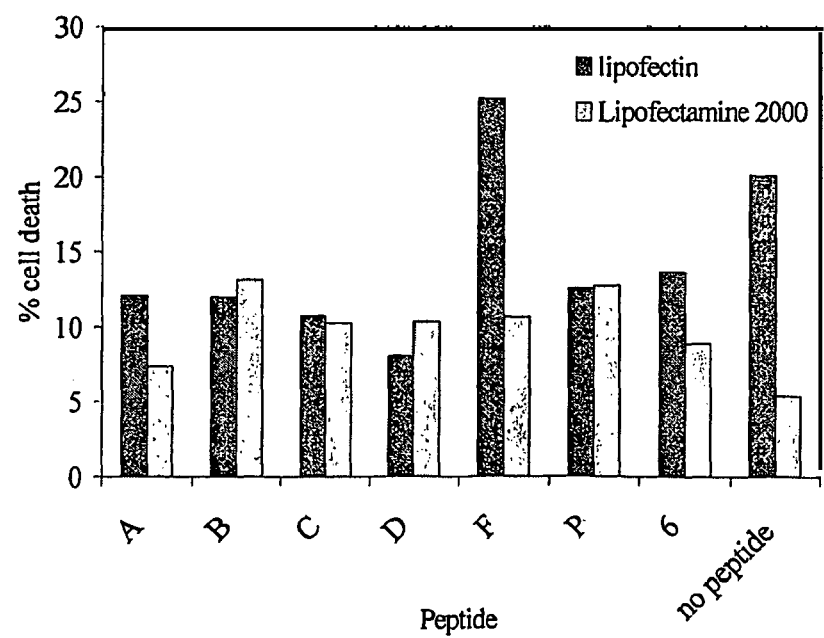
FIG. 7b shows cell death.

Transfection of monocytes using the targeting peptides gave comparable efficiencies to transfections using peptide 6, with peptides A, B and D again giving highest percentages of cells transfected, see FIG. 7a, although levels were lower than day 4 dendritic cells, with only 6% being the highest percent positive for EGFP (peptide A combined with Lipofectin). Toxicity was fairly low in most cases, at between 5 and 14% cell death, see FIG. 7b, except where peptide F or no peptide was used in conjunction with Lipofectin, where cell death rose to 25% and 20% respectively. Interestingly these were the conditions where transfection efficiency was lowest.

Figure 8:
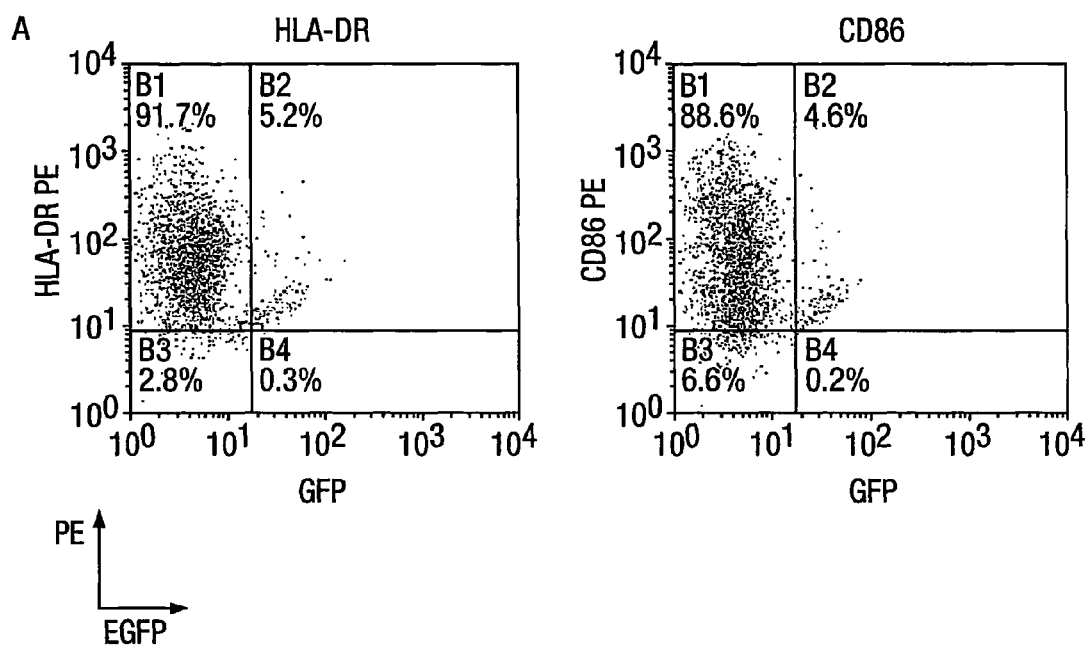
FIG. 8 shows that day 4 immature dendritic cells transfected with LID transfection vector containing peptide A and lipofectin (see the legend to FIG. 5) show upregulated CD86 and HLA-DR. The upper row of cells (A) are untransfected, the lower row of cells (B) are transfected. Cells from each sample were stained with PE-conjugated antibodies to HLA-DR and CD86 before flow cytometry. The results show pooled cells from two separate transfections and were reproducible with dendritic cells from another donor.
Figure 8:
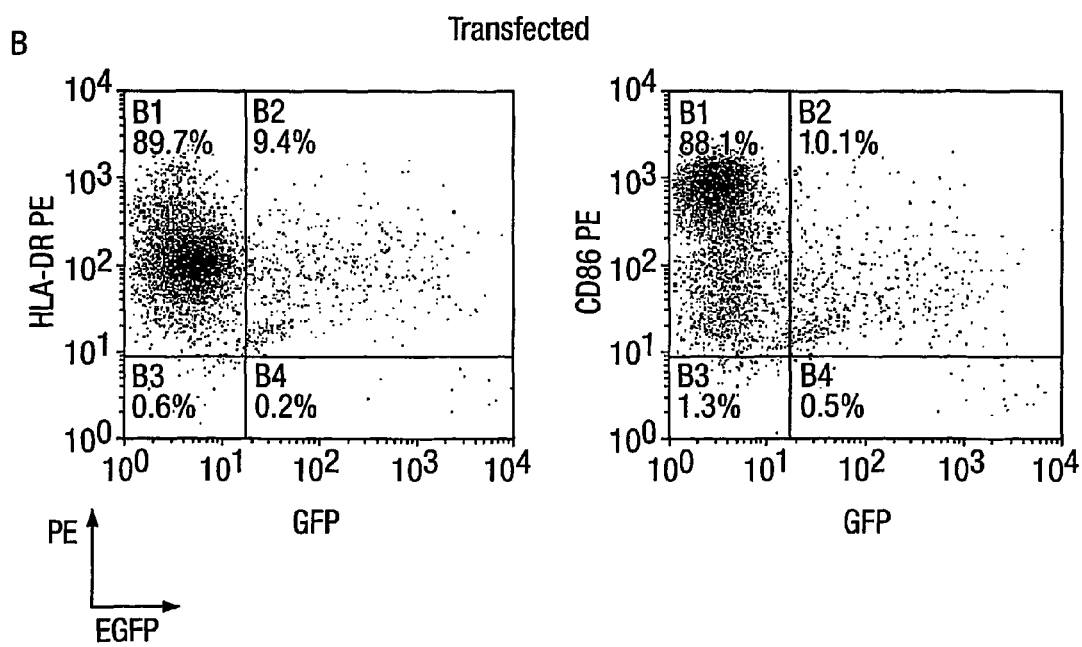

Transfection of immature day 4 dendritic cells resulted in upregulation of HLA-DR and CD86 molecules on the cells surface, see FIG. 8, indicating that activation of the dendritic cells is occurring. Both the EGFP positive and negative cells display upregulated markers, and not all transfected Dendritic cells show upregulated markers, suggesting the transfection process and not expression of EGFP is responsible for activation.

Figure 9:
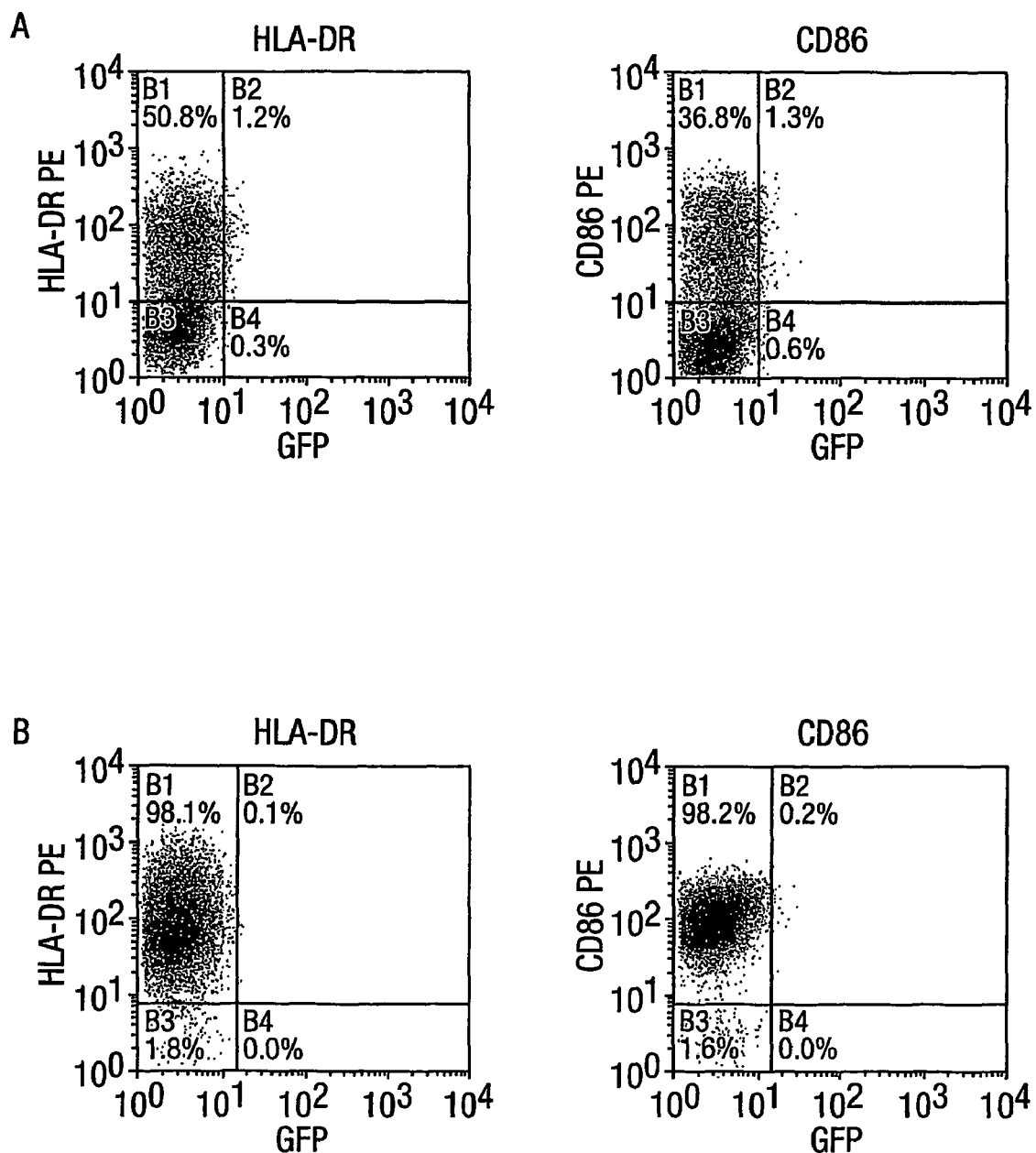
FIG. 9 shows maturation of transfection of day 4 dendritic cells in response to LPS (lypopolysaccaride). The immature cells were transfected with LID vector containing peptide D an dlipofectin (see the legend to FIG. 5). Cells were stained with antibodies as in FIG. 8. Results shown are the pooled cells from two separate transfections. Row A shows immature cells, Row B shows cells matured with LPS, Row C shows cells transfected and matured with LPS on day 4, Row D shows cells transfected on day 4 and matured with LPS on day 6.
Figure 9:
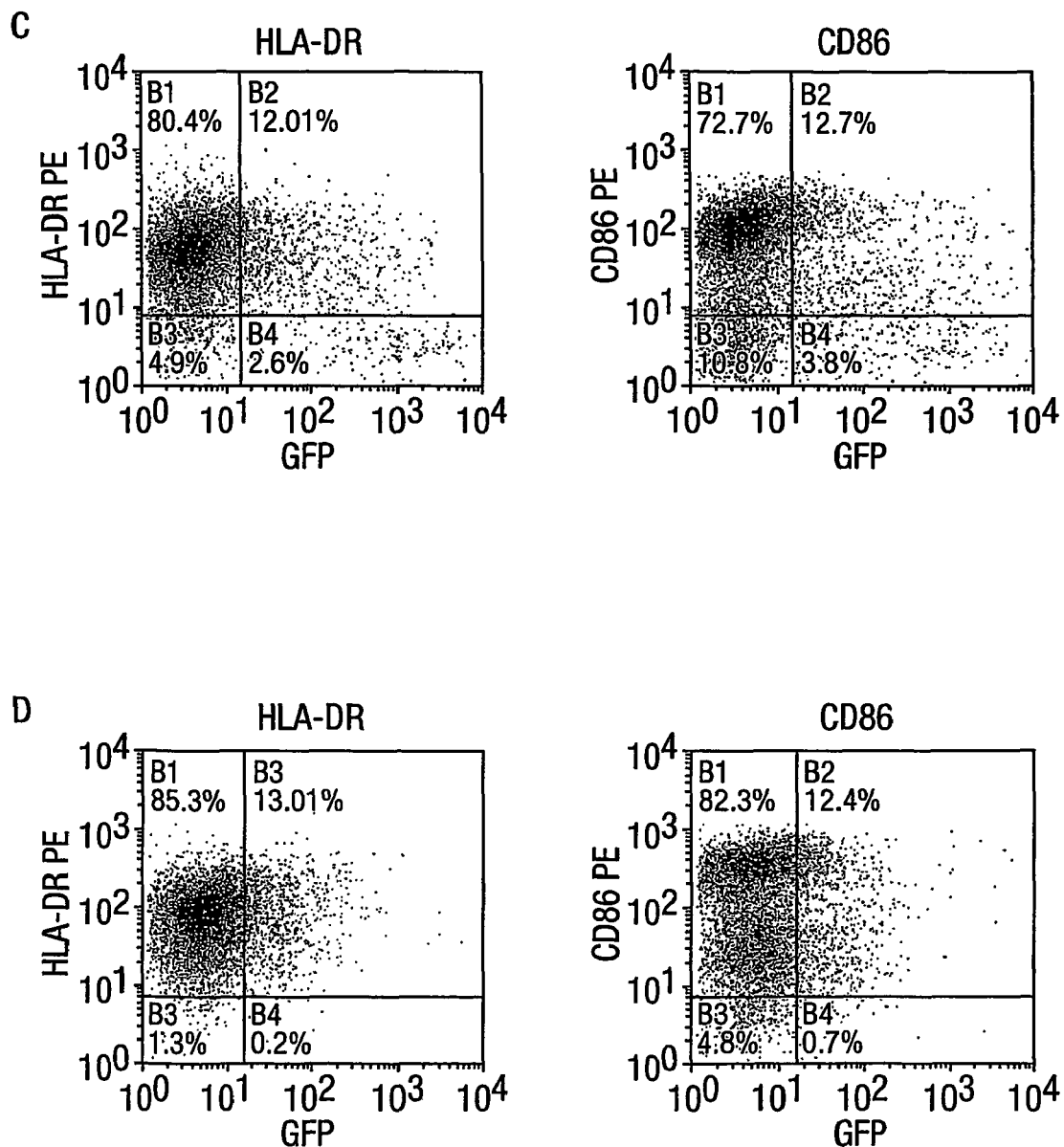

Maturation of dendritic cells following transfection using LPS showed a similar degree of upregulation of HLA-DR and CD86 to the transfected Dendritic cells without LPS, but with a lesser degree of activation compared to untransfected Dendritic cells incubated with LPS, suggesting that transfection may have a slightly inhibitory effect on activation, see FIG. 9. Addition of LPS to day 4 or day 6 cells had little effect on activation levels, with CD86 showing slightly less activation when cells were incubated with LPS on day 6 compared to day 4.

Although the peptide sequences of the invention were identified using dendritic cells, their utility is not limited to use with dendritic cells. The receptors to which the peptides bind may be expressed in other cell types. Cell types with which peptides of the invention may be used may be identified by any suitable screening procedure.

For example, peptides A and B in transfection vectors were tested for their ability to transfect other cell lines. The transfection efficiency was measured by luciferase activity per mg of protein present. In all cell lines tested, namely HMEC-1, HAEo- and N2a cells, at least one of the peptides A and B produced transfection efficiencies equal to or above those seen with peptide 6, the integrin targeting peptide.

In HMEC-1 cells, whilst peptide A produces a transfection efficiency approximately equal to that seen with peptide 6, peptide B can increase efficiency by one and a half times that of peptide 6, see FIG. 5.

In HAEo- cells, peptide A produced the highest efficiency of transfection, approximately double that seen with peptide 6, whilst efficiency using peptide B was one and a half times that using peptide 6, see FIG. 6.

In N2a (Neuro2A) cells, only peptide A produced transfection efficiencies equal to those seen with peptide 6, with peptide B producing efficiencies of less than half that value, see FIG. 7.

Furthermore, as described herein and in more detail below, the peptides of the invention may be used to retarget viral vectors to cells other than their normal targets.

Gene transfer of EGFP-reporter gene-bearing adenoviral constructs retargeted to immature dendritic cells from two different donors at 100,000 viral particles/cell in complete medium was measured by FACS. In both donors, retargeting the adenovirus with either peptide A or peptide B produced a transduction efficiency of between 64 and 79%, both being of similar efficiencies, and both transducing a significantly higher percentage of cells compared with adenovirus with a wild type fibre protein in the capsid, (between 43 and 46% positive), a KO1 fibre protein (between 0.7 and 1.4%), and a fibre protein bearing an irrelevant peptide (between 12 and 20%). No significant toxicity was seen in any transduction, ith cell death being measured at between 5 and 15%, see FIG. 8.

Using the same viral vectors, transduction of human monocyte-derived primary macrophages at 10,000 viral particles/cell in 2.5% serum also demonstrated that incorporating either peptide A (67.6% cells transduced) or peptide B (34.6% of cells transduced) into the viral coat significantly increased the efficiency of transduction above that seen with virus bearing a wild type fibre protein (13.3%) or KO1 fibre protein (9.2% cells transduced), see FIG. 8.

In all other cell types, and using the same viral vectors, when virus was added at 10,000 particles per cell in Opti-MEM, virus bearing peptide A or peptide B resulted in significantly higher transduction efficiency than virus bearing wild type fibre protein, KO1 fibre protein or fibre protein bearing an irrelevant peptide.

In N2a cells, virus bearing peptide A produced 63.5% transduced cells, peptide B 53.7%, whilst wild type produced 24.3, KO1 1.4% and irrelevant peptide 1.3%.

In HAEo- cells, peptide A produced 82.9% transduced cells, peptide B 79%, whereas wild type fibre bearing virus transduced 45.8%, KO1 virus 2% and virus bearing an irrelevant peptide 3.2%.

The same patterns of transduction efficiencies were seen with HMEC cells (peptide A 95.7%, peptide B 94.2%, wild type 73.3, KO1 2.7% and irrelevant 25.1%) and HepG2 cells (peptide A 88.5%, peptide B 79.7%, wild type 63.8%, KO1 1.7% and irrelevant 9.7%).

Incorporation of either peptide SHVKLNS [SEQ. ID. NO.: 29] or APSNSTA [SEQ. ID. NO.:15] into the adenoviral HI loop increased transduction efficiency of primary mouse dendritic cells to 71.7% and 54.1% respectively, a level considerably better than achieved with wild-type Ad5 (13.5%) (see Table 6). A much lower transduction efficiency of mouse Sca1-positive stem cells was achieved with all adenovirus samples, with SHVKLNS or APSNSTA retargeted adenovirus providing the best transduction efficiency of 5.4%, Ad5 virus transducing 2.2% and KO1 0.6%. Murine neuroblastoma cells (Neuro-2A) were also transduced more efficiently than with the wild-type virus, producing 63.5% and 53.7% GFP-positive cells with SHVKLNS [SEQ. ID. NO.: 29] and APSNSTA [SEQ. ID. NO.: 15] retargeted virus respectively compared to 24% with wild-type virus.

The ability of dendritic cells to mature in response to LPS was measured in virally transduced and untransduced samples by studying five maturation markers; HLA-DR, CD40, CD83 and the costimulatory molecules CD80 and CD86. Levels of all five markers (as assayed by flow cytometry) increased on maturation of untransduced cells by LPS, see Table 11.

The present invention provides a peptide derivative of formula A-B-C wherein

A is a polycationic nucleic acid-binding component,
B is a chemical bond or a spacer element, and
C is a peptide of the present invention.

The polycationic nucleic acid-binding component A is any polycation that is capable of binding to DNA or RNA. A polycation may be polycationic itself or it may have any number of cationic monomers provided the ability to bind to DNA or RNA is retained. For example, from 3 to 100 cationic monomers may be present, for example, from 10 to 20, for example from 14 to 18, for example, about 16.

An example of a nucleic acid-binding polycationic molecule is an oligopeptide comprising one or more cationic amino acids. Such a oligopeptide may, for example, be an oligo-lysine molecule having, for example, from 3 to 35, for example, 5 to 25 lysine residues, for example, having from 10 to 20 lysine residues, for example, from 14 to 18 lysine residues, for example, 16 lysine residues, an oligo-histidine molecule or an oligo-arginine molecule having, for example, from 3 to 35, for example, from 5 to 25, for example, from 10 to 20, for example, from 14 to 18, for example, 16 histidine or arginine residues, respectively, or a combined oligomer comprising any combination of histidine, arginine and lysine residues and having, for example, a total of from 3 to 35, for example, from 5 to 25 residues, preferably for example, from 10 to 20 residues, for example, from 14 to 18 residues, for example 16 residues.

An oligolysine is particularly preferred, for example, having from 3 to 35, for example, from 2 to 25, for example, form 10 to 20 lysine residues, for example, from 13 to 19, for example, from 14 to 18, for example, from 15 to 17 residues, for example, 16 residues i.e. $[K]_{16}$, [SEQ. ID. NO.:54] "K" denoting lysine.

Further examples of polycationic components include dendrimers and polyethylenimine. Polyethylenimine (PEI) is a non-toxic, cross-linked cationic polymer with gene delivery potential (*Proc. Natl. Acad. Sci.,* 1995, 92, 7297-7301). Polyethylenimine is obtainable from Fluka (800 kDa) or from Sigma (50 kDa) or alternatively pre-diluted for transfection purposes from PolyPlus-tranfection (Illkirch, France). Typically, PEI is most efficient when used in a 9 fold excess over DNA, the excess ratio being calculated as PEI nitrogen: DNA phosphate, and at pH 5 to 8. Such parameters may optimised in a manner familiar to the person skilled in the art.

The polycationic nucleic acid-binding component may be linked or otherwise attached to the peptide of the invention to form a peptide derivative of the invention A-B-C in which C denotes a peptide of the present invention, B denotes a chemical bond or a spacer element, and A denotes a polycationic nucleic acid binding component. The polycationic component may be linked at any appropriate position of the peptide. A polycationic nucleic acid-binding component may, for example, be chemically bonded directly to a peptide of the invention, in which case the component B represents a chemical bond. For example, a peptide of the invention may be linked by a peptide bond, for example, in the case of an oligolysine polycationic nucleic acid-binding component. An example of a peptide derivative of the invention is an oligolysine, for example, $[K]_{16}$ [SEQ. ID. NO.:54], linked via a peptide bond to a peptide of the invention, for example, a peptide as described above. A further example of a peptide derivative of the invention is a polyethylenimine linked via a covalent link to a peptide of the invention, for example, a peptide as described above. Such a covalent link may be, for example, a disulphide bridge or a succinimidyl bridge, using methods known in the art see for example, *Gene Therapy,* 1999, 6, 138-145).

In another embodiment, a peptide of the invention may be attached to a polycationic nucleic acid binding component via a spacer to form a peptide derivative of the invention.

A spacer element is generally a peptide, that is to say, it comprises amino acid residues. The amino acids may be naturally occurring or non-naturally occurring. They may have L- or D-configuration. A spacer may have two or more amino acids. It may, for example, comprise three or more amino acids, for example, four or more, for example, five or more, for example, up to ten amino acids or more. The amino acids may be the same or different, but the use of multiple lysine residues (or other cationic amino acids suitable for use in the polycationic nucleic acid-binding component of a vector complex) should generally be avoided in the spacer as oligo-lysine sequences have activity as a polycationic nucleic acid-binding component.

The spacer may be, for example, the dipeptide glycine-glycine (GG) or glycine-alanine (GA). Generally it is preferable that the spacer is longer and/or more hydrophobic than the dipeptide spacers GG and GA.

The spacer may be more hydrophobic than the dipeptides GG and GA. For example, amino acids that are more hydrophobic than glycine and alanine may be used. Examples of hydrophobic amino acids are well known and include ε-amino hexanoic acid.

A spacer may be either longer or more hydrophobic than the dipeptides GG and GA, or it may be both longer and more hydrophobic. An example of the latter type of spacer is XSXGA [SEQ. ID. NO.:55], wherein S=serine, G=glycine, A=alanine and X=ε-amino hexanoic acid. This spacer is highly hydrophobic.

A combined peptide/polycationic nucleic acid binding component i.e. a peptide derivative of the invention may be referred to below as component "I".

The present invention further provides a transfection mixture that comprises (i) lipid component, (ii) a polycationic nucleic acid binding component, and (iii) a peptide of the invention.

The present invention also provides a non-viral transfection transfection complex that comprises (i) lipid component, (ii) a polycationic nucleic acid binding component, and (iii) a peptide of the invention, and (iv) a nucleic acid.

In a transfection mixture or transfection complex of the invention, components (ii) and (iii) are preferably in the form of a peptide derivative of the invention, for example, as described above.

The lipid component of a transfection mixture or transfection complex of the invention may be or may form a cationic liposome.

The lipid component may be or may comprise one or more lipids selected from cationic lipids and lipids having membrane destabilising or fusogenic properties, especially a combination of a cationic lipid and a lipid that has membrane destabilising properties.

A preferred lipid component ("L") is or comprises the neutral lipid dioleyl phosphatidylethanolamine, referred to herein as "DOPE". DOPE has membrane destabilising properties sometimes referred to as "fusogenic" properties (Farhood et al. 1995). Other lipids, for example, neutral lipids, having membrane destabilising properties, especially membrane destabilising properties like those of DOPE may be used instead of or as well as DOPE.

Other phospholipids having at least one long chain alkyl group, for example, di(long alkyl chain)phospholipids may be used. The phospholipid may comprise a phosphatidyl group, for example, a phosphatidylalkanolamine group, for example, a phosphatidyl-ethanolamine group.

A further preferred lipid component is or comprises the cationic lipid N-[1-(2,3-dioleyloxy)propyl]-N,N,N-trimethylammonium chloride, referred to herein as "DOTMA". DOTMA has cationic properties. Other cationic lipids may be used in addition to or as an alternative to DOTMA, in particular cationic lipids having similar properties to those of DOTMA. Such lipids are, for example, quaternary ammonium salts substituted by three short chain alkyl groups, and one long alkyl group. The short chain alkyl groups may be the same or different, and may be selected from methyl and ethyl groups. At least one and up to three of the short chain alkyl group may be a methyl group. The long alkyl chain group may have a straight or branched chain, for example, a di(long chain alkyl)alkyl group.

Another preferred lipid component is or comprises the lipid 2,3-dioleyloxy-N[2-(spermidinecarboxamido)ethyl]-N,N-dimethyl-1-propanaminiumtrifluoridoacetate, referred to herein as "DOSPA". Analogous lipids may be used in addition to or as an alternative to DOSPA, in particular lipids having similar properties to those of DOSPA. Such lipids have, for example, different short chain alkyl groups from those in DOSPA.

A preferred lipid component comprises DOPE and one or more other lipid components, for example, as described above. Especially preferred is a lipid component that comprises a mixture of DOPE and DOTMA. Such mixtures form cationic liposomes. An equimolar mixture of DOPE and DOTMA is found to be particularly effective. Such a mixture is known generically as "lipofectin" and is available commercially under the name "Lipofectin". The term "lipofectin" is used herein generically to denote an equimolar mixture of DOPE and DOTMA. Other mixtures of lipids that are cationic liposomes having similar properties to lipofectin may be used. Lipofectin is particularly useful as it is effective in all cell types tested.

A further preferred lipid component comprises a mixture of DOPE and DOSPA. Such mixtures also form cationic liposomes. A mixture of DOPE and DOSPA in a ratio by weight 3:1 DOSPA:DOPE is particularly effective. Such a mixture, in membrane filtered water, is available commercially under the name "Lipofectamine", for example, Lipofectamine 2000. Mixtures comprising DOPE, DOTMA and DOSPA may be used, for example, mixtures of lipofectin and lipofectamine.

Other cationic lipids are available commercially, for example, DOTAP (Boehringer-Mannheim) and lipids in the Tfx range (Promega). DOTAP is N-[1-(2,3-diolyloxy)propyl]-N,N,N-tri-methylammonium methylsulphate. The Tfx reagents are mixtures of a synthetic cationic lipid [N,N,N,N'-tetramethyl-N,N'-bis(2-hydroxyethyl)-2,3-di(oleoyloxy)-1,4-butanediammonium iodide and DOPE. All the reagents contain the same amount of the cationic lipid component but contain different molar amounts of the fusogneic lipid, DOPE.

However, lipofectin and lipofectamine appear to be markedly more effective for promoting transfection of cells with a nucleic acid than are DOTPA and Tfx agents.

WO 03/094974 (PCT/GB03/01985) describes several lipids. Such lipids include dicationic lipids, PEG-based lipids incorporating a spacer between cationic centres, and erythritol-based lipids.

Two of the lipids described in WO 03/094974 have the general formula (I) or (II):

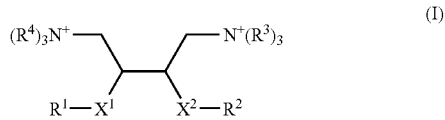

(I)

wherein

X¹ and X² are the same or different and are selected from —O—CH₂— and —O—C(O)—;

R¹ and R² are the same or different and are straight or branched, saturated or unsaturated $C_7$ to $C_{24}$ hydrocarbyl groups which are unsubstituted or substituted by one or more substituents selected from hydroxy, halogen and OR', wherein R' is a $C_1$ to $C_6$ hydrocarbyl group;

each $R^3$ and each $R^4$ is the same or different and is a straight or branched, saturated or unsaturated $C_1$ to $C_{10}$ hydrocarbyl group which is unsubstituted or substituted by one or more substituents selected from hydroxy, halogen, —OR', —C(O)OH, —CN, —NR'R", and —C(O)R" wherein R' and R" are the same or different and are $C_1$ to $C_6$ hydrocarbyl;

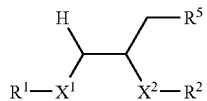

(I)

wherein
$X^1$ and $X^2$ are the same or different and are as defined above;
$R^1$ and $R^2$ are the same or different and are as defined above;
$R^5$ is —$N^+(R^3)_2$—$R^6$ wherein each $R^3$ is the same or different and is as defined above and $R^6$ is either:
(a) -[A-Y]—$_n$$R^4$ wherein
each Y is the same or different and is —$N^+(R^4)_2$— wherein $R^4$ is as defined above; each A is the same or different and is a $C_{1-20}$ alkylene group which is unsubstituted or substituted by one or more substituents selected from hydroxy, halogen, —OR', —C(O)OH, —CN, —NR'R", and —C(O)R" wherein R' and R" are the same or different and are $C_{1-6}$ hydrocarbyl; and
n is from 1 to 10, and
$R^4$ is as defined above; or
(b) —[B—O]-$_m$B-Q wherein:
each B is the same or different and is a $C_{1-10}$ alkylene group which is unsubstituted or substituted by one or more substituents selected from hydroxy, halogen, —OR', —C(O)OH, —CN, —NR'R" and —C(O)R" wherein R' and R" are the same or different and are $C_{1-6}$ hydrocarbyl;
m is from 1 to 10; and
Q is selected from —$N^+(R^3)_3$, —OH, —OR', —OC(O)R' and halogen, wherein $R^3$ and R' are as defined above.

WO 03/094974 also describes a structure III, which is an erythritol-based lipid

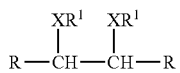

wherein:
the Rs, which may be the same or different, are
(a) H,
(b) —$CH_2$—$N^+(R_2)^2$—$CH_2$—$CH_2$—[Y—$(CH_2)_p]_q$-Z, or
(c) —$CH_2$—$N^+(R^4)_3$,
with the proviso that one R is H and the other is group (b); or both groups R are groups (c); and wherein the Xs which may be the same or different, are $OCH_2$ or O—C(O);
the $R^1$s, which may be the same or different, are saturated or unsaturated, C7 to C23 chains;
the $R^2$s, which may be the same or different, are C1 to C6 saturated or unsaturated chains;
Y is NH, $CH_2$, O or N(acetyl);

Z is $O(C_1$ to $C_4)$, $OC(O)R^3$, $N^+R_3^4$, OH, F, Cl, Br or I where $R^3$ is C1 to C6 alkyl;
the $R^4$s, which may be the same or different, are C1 to C6 chains;
n is from 2, 3 or 4; and
m is from 1 to 200 and where it is at least 2 the resulting repeating units may be the same or different.

Any of the lipids described in WO 03/094974 may be used as the lipid component according to the present invention, or as one element of a lipid component according to the present invention, for example, a lipid according to WO 03/094974, for example, as described above, may be used in combination with any other lipid component, for example, one of the preferred lipids described above. Preferred ratios are, for example, as described above.

The nucleic acid component of a transfection complex of the invention may, for example, be obtained from natural sources, or may be produced recombinantly or by chemical synthesis.

The nucleic acid component may, for example, consist of or comprise a molecule having a specific function, for example, a nuclear targeting molecule. The nucleic acid may be DNA or RNA. DNA may be single stranded or double stranded. The nucleic acid may be suitable for use in gene therapy, in gene vaccination or in anti-sense therapy. The nucleic acid may be or may relate to a gene that is the target for particular gene therapy or may be a molecule that can function as a gene vaccine or as an anti-sense therapeutic agent. The nucleic acid may be or correspond to a complete coding sequence or may be part of a coding sequence.

Alternatively, the nucleic acid may encode a protein that is commercially useful, for example industrially or scientifically useful, for example an enzyme; that is pharmaceutically useful, for example, a protein that can be used therapeutically or prophylactically as a medicament or vaccine; or that is diagnostically useful, for example, an antigen for use in an ELISA. Host cells capable of producing commercially useful proteins are sometimes called "cell factories".

In the case of a nucleic acid sequence to be expressed, appropriate transcriptional and translational control elements are generally provided.

The nucleic acid is generally DNA but RNA may be used in some cases, for example, in cancer vaccination. The nucleic acid component may be referred to below as the "plasmid component" or component "D".

Examples of nucleic acids that can be used in gene therapy and/or in gene vaccination include the coding sequence of a protein and the cDNA copy and genomic version thereof, the latter including introns as well as exons, and also the regulatory upstream and downstream sequences. Other useful nucleic acids include sequences involved in repairing genes and in homologous recombination. These can be molecules such as RNA/DNA chimeras (Bandyopadhyay et al., 1999; Cole-Strauss et al., 1996; Kren et al., 1998; Yoon et al., 1996) or DNA oligonucleotides (Goncz et al., 1998). A useful nucleic acid can be a short sequence contained in a plasmid, or another large nucleic acid that mediates integration of plasmids or nucleic acids, for example, phage integrase (Groth et al., 2000; Olivares et al., 2001; Stoll et al., 2002; Thyagarajan et al., 2000; Thyagarajan et al., 2001) and "Sleeping Beauty" transposons (Yant et al., 2000).

DNA oligonucleotides can be delivered for purposes of antisense regulation (Bachmann et al., 1998; Knudsen and Nielsen, 1997; Mannion et al., 1998; Woolf et al., 1995) or as transcription factor decoys (Ehsan et al., 2001; Ehsan et al., 2002; Mann et al., 1999; Morishita et al., 1995). CpG-rich oligonucleotide sequences may be useful as adjuvants to boost vaccine responses (Krieg et al., 1995).

Another important new class of molecules that can be used in gene therapy includes small interfering RNA. As explained above, RNA interference in mammalian cells has emerged in the last two or three years as an important new approach to the regulation of gene expression, with a high degree of specificity (reviewed Shi 2003). Double-stranded RNA molecules of 20-30 nt in length, known as small interfering RNA (siRNA) molecules, target homologous regions of mRNA. They then activate a conserved pathway that leads to degradation of the mRNA target. The precise mechanism of action of siRNA is under intense investigation but it is clear that the application of siRNA to mammalian cells has the potential to revolutionize the field of functional genomics. The ability to simply, effectively, and specifically down-regulate the expression of genes in mammalian cells holds enormous scientific, commercial, and therapeutic potential.

Currently there is no way to predict an effective siRNA target so screening of numerous sequences is performed and numerous potential molecules may have to be screened. Such screening is most conveniently performed with chemically synthesised siRNA molecules delivered by non-viral vectors. The use of the transfection complexes of the invention for transfecting siRNA molecules for subsequent screening thus provides benefits of cost-effectiveness as well as greater functionality. siRNA molecules may also be used therapeutically. Such transfection and subsequent screening of siRNAs is part of the present invention.

The efficiency of transfection of a peptide of the invention, a polycationic nucleic acid-binding component, a peptide derivative of the invention, a lipid component or any combination thereof may be determined readily using the methods described herein.

The efficiency of transfection using a transfection complex as described above as transfection vector is influenced by the ratio lipid component:peptide/polycationic nucleic acid-binding component i.e. peptide derivative of the invention: DNA or RNA. For any chosen combination of components for any particular type of cell to be transfected, the optimal ratios can be determined simply by admixing the components in different ratios and measuring the transfection rate for that cell type, for example, as described herein.

Lipofectin and lipofectamine appear to be particularly effective in enhancing transfection in the system described above. Lipofectin has the advantage that only very small amounts are required. Any side effects that may occur are therefore minimised. The cationic lipids described in WO 03/-94974 may also be particularly effective.

A suitable weight ratio between the lipid and the DNA components may be from 0.75 to 4:1. A ratio of 0.75:1 has been found suitable. For any given transfection experiment, this ratio may be optimised using methods known in the art.

A transfection mixture of the invention may be produced by admixing component (i), the lipid component, component (ii), the polycationic nucleic acid binding component, and component (iii), the peptide of the invention. A transfection complex as described above may be produced by admixing components (i), (ii), (iii) and (iv), the nucleic acid component. Components (ii) and (iii) are preferably in the form of a peptide derivative of the invention.

Although the components may be admixed in any order, it is generally preferable that the lipid component is not added last. In the case where a peptide derivative is used, it is generally preferable to combine the components in the following order: lipid component; peptide derivative; DNA or RNA component, ie to combine the lipid derivative and the peptide, and finally to combine the nucleic acid component with the lipid/peptide mixture.

A transfection mixture comprising a peptide derivative and a lipid component may be used to produce a nucleic acid-containing transfection complex by the incorporation of the nucleic acid with the transfection mixture, for example, by admixture. Alternatively, the transfection mixture may be used for the production of a vector complex which comprises, instead of the nucleic acid component, any other component that is capable of binding to the polycationic nucleic-acid binding component, for example, a protein.

Transfection mixtures of the invention are generally stable on storage at 4° C. It may therefore be convenient to prepare the transfection mixture in bulk and to use portions of the transfection mixture as and when required to prepare a transfection complex incorporating a nucleic acid of choice.

A transfection mixture of the invention may preferably comprise an equimolar mixture of DOPE and DOTMA (lipofectin) as the lipid component, and a peptide of the invention, especially peptide derivative of the invention, for example, a $[K]_{16}$-peptide. A spacer as described above may be present in the peptide derivative. The preferred molar ratio lipofectine:peptide derivative is 0.75:4.

The individual components of a transfection mixture of the invention are each described herein.

The preferred components, preferred combinations of components, preferred ratios of components and preferred order of mixing, both with regard to the transfection mixture and to the transfection complex and its production are described herein.

The invention further provides a non-viral transfection complex comprising:
(i) a nucleic acid,
(iii) a polycationic nucleic acid-binding component, and
(iv) a peptide of the invention.

Cells that may be transfected by a transfection complex comprising a peptide of the invention include, for example, endothelial and epithelial cells, for example, cells of any part of the airway epithelium, including bronchial and lung epithelium, and the corneal endothelium. The airway epithelium is an important target for gene therapy for cystic fibrosis and asthma.

The invention also provides a viral vector, which vector comprises a peptide of the invention.

A viral vector is targeted to the receptor to which the virus binds to gain entry into its host cell. Such a vector can be retargeted by combining a peptide of the invention with the vector. The peptide should be combined in such a manner and at such a site that the vector can bind to host cells and that can still function as a vector.

The viral vector also comprises a nucleic acid of interest. Such a nucleic acid may be as described above in relation to a transfection complex of the invention. The incorporation of a peptide of the invention in a viral vector should not interfere with the nucleic acid. The peptide of the invention may be incorporated with the viral vector before or after the nucleic acid is inserted into the vector.

The viral vector is, for example, an adenovirus, the native receptor for which is the Coxsackie-Adenovirus Receptor (CAR) protein. This is the primary receptor for adenovirus. Secondary receptors include integrins and proteoglycans. CAR is found on many cell types but only at low levels on dendritic cells and either not, or only at low levels, on the apical surface of airway epithelial cells, which restricts the efficiency of adenoviral vectors in the cells and tissues. Adenoviral vectors can be retargeted, for example, by incorporation of a peptide of the invention, for example, in the HI region of the fibre protein in the capsid (Nicklin et al., 2001).

Adenovirus type 5, for example, is a good vector in principle as it transduces a wide range of cell types with high efficiency but is a poor vector for dendritic cells as such cells have low levels of the CAR receptor. When a peptide of the present invention is inserted into the HI region of the fibre protein of the capsid, transfection efficiency for dendritic cells increased from 20 to 45% as observed using an adenoviral type 5 vector with a wild type fibre protein in the capsid to between 64 and 79%. Moreover, the increase in transfection efficiency is also observed in other cells, not only dendritic cells. For example, transfection of human primary macrophages using a retargeted adenoviral vector incorporating a peptide of the invention increased from about 13% as observed with wild-type virus (and about 9% with KO1 fibre) to up to about 67% for peptide SHVKLNS [SEQ. ID. NO.:29] and about 35% for peptide APSNSTA [SEQ. ID. NO.:15]; with N2a cells the transefection efficiency was about 63% for retargeted vector compared with about 24% for wild type vector; with HAEo- cells the values were about 83% for peptide SHVKLNS [SEQ. ID. NO.:29] and about 79% for peptide APSNSTA [SEQ. ID. NO.:15] whereas wild type fibre bearing virus had a transduction efficiency of about 45%, KOl virus about 2% and virus bearing an irrelevant peptide about 32%. The same patterns of transduction efficiencies were seen with HMEC-1 endothelial cells: peptide SHVKLNS [SEQ. ID. NO.:29] about 95% peptide APSNSTA [SEQ. ID. NO.:15] about 94%, wild type about 73%, KO1 virus about 3% 2.7% and irrelevant peptide about 25% and HepG2 hepatocarcinoma cells: peptide SHVKLNS [SEQ. ID. NO.:29] about 88%, peptide APSNSTA [SEQ. ID. NO.:15] about 80%, wild type about 64%, KO1 about 2% and irrelevant peptide about 10%.

Alternatively, a viral vector may be retargeted by formation of a complex with a peptide of the invention that comprises a cationic domain that is capable of binding electrostatically to the viral capsid or coat. An example of such a peptide is a peptide derivative of the invention, which comprises a polycationic nucleic acid binding component, for example, a polycationic oligolysine, for example, having from 3 to 32 lysine residue, for example, as described above, for example $[K]_{16}$ [SEQ. ID. NO.:15]. An electro-static complex between the virus and the modified peptide may be produced by mixing solutions of the virus and the peptide. Such a complex is part of the present invention.

In a further alternative, a peptide of the invention is incorporated with the viral vector by means of an antibody that is capable of binding to the virus. The antibody may be a bispecific antibody capable of binding to the peptide and to the virus, or the peptide and the antibody may be in the form of a fusion protein. In either case the peptide may be used to mediate adenoviral binding and display on the virus, allowing retargeted transduction (Watkins et al., 1997). The antibody component may be of any antibody class, may be an appropriate antigen-binding domain or domains, and may be or be derived from a chimeric or humanised antibody. Such a fusion protein is part of the present invention. A bispecific antibody and the peptide or the peptide-antibody fusion protein may be contacted with a viral vector and allowed to bind. Methods of making and selecting bispecific antibodies and peptide/antibody fusion proteins are known in the art, see for example, (Nicklin et al., 2001; Pereboev et al., 2002; Tillman et al., 1999; Watkins et al., 1997; Wickham et al., 1997)

A complex, a bispecific antibody and a peptide-antibody fusion protein are all part of the present invention.

The transfection efficiency of a viral vector of the present invention for any particular cell or cell type relative to the efficiency of a wild type vector may be determined readily, for example, as described in Example 3 below.

Although described above in relation to adenovirus, a viral vector of the present invention may be a viral vector that can be retargeted using a peptide of the present invention. Examples of such viral vectors include genetically engineered, replication-defective derivatives of retrovirus, lentivirus, adenovirus, adeno-associated virus (AAV), and herpes simplex virus (HSV).

Unless specified otherwise, a viral vector of the present invention may be used analogously to a transfection complex of the invention, for example, for same purposes.

The present invention also provides a process for expressing a nucleic acid in host cells, which comprises contacting the host cells in vitro or in vivo with a transfection complex or viral vector of the invention comprising the nucleic acid, and culturing the host cells under conditions that enable the cells to express the nucleic acid.

The present invention further provides a process for the production of a protein in host cells, which comprises contacting the host cells in vitro or in vivo with a transfection complex or viral vector of the invention that comprises a nucleic acid that encodes the protein, allowing the cells to express the protein, and obtaining the protein. The protein may be obtained either from the host cell or from the culture medium. Suitable host cells are well know. Examples of suitable host cells include Chinese hamster ovary (CHO) cells, (Castilho et al., 2002), BHK cells (Cruz et al., 2002), 293 cells (Durocher et al., 2002) and insect cells such as Sf9 [Wang, 2000 #1964].

The present invention further provides a method of transfecting cells comprising contacting the cells with a transfection complex or viral vector according to the invention. Such transfection may be carried out in vitro or in vivo. Cells transfected in vitro may, if desired, be administered to a human or non-human animal subject for therapeutic purposes, see below.

The invention further provides cells, transfected with a nucleic acid by a method according to the invention, and also the progeny of such cells.

The present invention also provides a pharmaceutical composition which comprises a transfection complex or viral vector of the invention comprising a nucleic acid in admixture or conjunction with a pharmaceutically suitable carrier. The composition may be a vaccine, in which case it may comprise an adjuvant.

The present invention also provides a method for the treatment or prophylaxis of a condition caused in a human or in a non-human animal by a defect and/or a deficiency in a gene, which comprises administering to the human or to the non-human animal a transfection complex or viral vector of the invention comprising a nucleic acid suitable for correcting the defect or deficiency.

The present invention also provides a method for therapeutic or prophylactic immunisation of a human or of a non-human animal, which comprises administering to the human or to the non-human animal a transfection complex or viral vector of the invention comprising an appropriate nucleic acid.

The present invention also provides a method of anti-sense therapy of a human or of a non-human animal, comprising anti-sense DNA administering to the human or to the non-human animal a transfection complex or viral vector of the invention comprising the anti-sense nucleic acid.

The present invention also provides the use of a transfection complex or viral vector of the invention comprising a nucleic acid for the manufacture of a medicament for the prophylaxis of a condition caused in a human or in a non-human animal by a defect and/or a deficiency in a gene, for therapeutic or prophylactic immunisation of a human or of a non-human animal, or for anti-sense therapy of a human or of a non-human animal.

An alternative to administering a complex or vector of the invention is to administer cells that have been transfected in vitro.

A non-human animal is, for example, a mammal, bird or fish, and is particularly a commercially reared animal.

The nucleic acid, either DNA or RNA, in the transfection complex or viral vector is appropriate for the intended use, for example, for gene therapy, gene vaccination, anti-sense therapy or protein production, see above. The DNA or RNA and hence the transfection complex or viral vector is administered in an amount effective for the intended purpose.

The treatments and uses described above may be carried out by administering the respective transfection complex, viral vector, agent or medicament in an appropriate manner, for example, administration may be systemic, local or topical, depending on the site of the target cells and the intended effect. For example, in the case of airway epithelia, delivery is generally local and topical, and may involve nebulisation or bronchoscopy. For treatment of eyes, administration may be intraocular. For other target systemic administration may required, in which case administration may be by injection, for example, intravenous, intramuscular or intraperitoneal injection.

In a further embodiment, the present invention provides a kit comprising a transfection complex or viral vector of the invention comprising a nucleic acid.

The present invention also provides a kit that comprises the following items: (a) a peptide of the invention; (b) a polycationic nucleic acid-binding component; and (c) a lipid component. Such a kit may further comprise (d) a nucleic acid. Components (a) and (b) are preferably in the form of a peptide derivative of the invention. Alternatively, a kit may comprise components (a), (b) and (d).

Such a nucleic acid may be single-stranded or double stranded and may be a plasmid or an artificial chromosome. The nucleic acid component may be provided by a transfection transfection complex suitable for the expression of the nucleic acid, the vector complex being either empty or comprising the nucleic acid.

The components (a) to (d) kit are, for example, as described above in relation to a transfection vector mixture or transfection complex.

The polycationic nucleic acid binding component is preferably an oligolysine, as described above. The lipid component is preferably capable of forming a cationic liposome, and preferably is or comprises DOPE and/or DOTMA, for example, an equimolar mixture thereof, or is or comprises DOSPA, for example, a mixture of DOPE and DOSPA, for example in the weight ratio DOPE:DOSPA of 1:3. The ratios between the components are preferably as described above, as is the order of mixing of the components.

A kit generally comprises instructions, which preferably indicate the preferred ratios of the components and the preferred order of use or admixing of the components, for example, as described above. A kit may be used for gene therapy, gene vaccination or anti-sense therapy. Alternatively, it may be used for transfecting a host cell with a nucleic acid encoding a commercially useful protein i.e. to produce a so-called "cell factory".

Targets for gene therapy are well known and include monogenic disorders, for example, cystic fibrosis, various cancers, and infections, for example, viral infections, for example, with HIV. For example, transfection with the p53 gene offers great potential for cancer treatment. Targets for gene vaccination are also well known, and include vaccination against pathogens for which vaccines derived from natural sources are too dangerous for human use and recombinant vaccines are not always effective, for example, hepatitis B virus, HIV, HCV and herpes simplex virus. Targets for anti-sense therapy are also known. Further targets for gene therapy and anti-sense therapy are being proposed as knowledge of the genetic basis of disease increases, as are further targets for gene vaccination. The present invention enhances the transfection efficiency and hence the effectiveness of the treatment.

Transfection of cells with pro-inflammatory cytokines may be used in cancer immunotherapy, with anti-inflammatory cytokines in the treatment of auto-immune diseases, for example, rheumatoid arthritis and multiple sclerosis.

Cells may be transfected with an anti-angiogenic gene, for example for soluble VEGF-R for treatment of cancer, or with an angiogenic gene, for example, VEGF, for myocardial diseases, or peripheral vascular disease.

Non-viral transfection complexes of the invention may be effective for intracellular transport of very large DNA molecules, for example, DNA larger than 125 kb, which is particularly difficult using conventional vectors. This enables the introduction of artificial chromosomes into cells.

Transfection of the airways, for example, the bronchial epithelium demonstrates utility for gene therapy of, for example, respiratory diseases, such as cystic fibrosis, emphysema, asthma, pulmonory fibrosis, pulmonary hypertension and lung cancer.

Cystic fibrosis (CF) is the most common monogenic disorder in the Caucasian population. Morbidity is mainly associated with lung disease. CF is caused by mutations in the gene encoding the cystic fibrosis transmembrane conductance regulator protein (CFTR), a cell membrane channel that mediates secretion of chloride ions. Correction of this defect in the bronchial cells by CFTR gene transfer will correct the biochemical transport defect and, hence, the lung disease. Clinical trials so far have generated encouraging data but highlighted the need for more efficient, non-toxic vectors.

The enhanced levels of transfection make the method of the invention particularly suitable for the production of host cells capable of producing a desired protein, so-called "cell factories". For long-term production, it is desirable that the introduced nucleic acid is incorporated in the genome of the host cell, or otherwise stably maintained. That can be readily ascertained. As indicated above, the range of proteins produced in this way is large, including enzymes for scientific and industrial use, proteins for use in therapy and prophylaxis, immunogens for use in vaccines and antigens for use in diagnosis.

The present invention is especially useful with a receptor targeted vector complex that is capable of high efficiency transfection. In a preferred embodiment, the vector complex comprises four modular elements; an oligolysine, especially $[K]_{16}$ [SEQ. ID. NO.: 54], DNA-binding or RNA-binding element; a peptide of the invention, for example, a peptide described herein; a DNA or RNA sequence, optionally in a plasmid, and optionally regulated by a viral promoter and an enhancing element; the cationic liposome DOTMA/DOPE (lipofectin). The combination of oligolysine-peptide/DNA or RNA complex with the cationic liposome formulation DOTMA/DOPE is a potent combination. Alternatively a DOPE/DOSPA formulation may be used instead of or in addition to a DOTMA/DOPE formulation. The optimisation of variables associated with complex formation and the mode of transfection by LID vector complexes has been demonstrated.

The most important variables in the formation of optimal transfection complexes appear to be the ratio of the three components and their order of mixing.

The invention further provides a method for identifying an siRNA. A panel of siRNA molecules of 20-30 nucleotides length is designed for homology to regions scattered throughout the target gene sequence. siRNA molecules can be synthesised by commercial sources, e.g. Qiagen, Promega. A cell that expresses the target gene is transfected with the individual siRNA and expression levels quantified by standard, relevant protein assays or mRNA assays.

The invention provides the use of a peptide of the invention to target an entity to a cell or cell type to which the peptide binds. The entity may be a nucleic acid or another molecule, for example, a therapeutically or pharmaceutically active molecule, or a molecule comprising a detectable label.

The following non-limiting Examples illustrate the present invention.

EXAMPLES

Example 1

Identification of Peptide Motifs

Materials and Methods (i) Antibodies

The following anti-human antibodies were used for flow cytometry: HLA-DR, CD40, CD86, and mouse IgG1 and IgG2 fluorescent isotype control antibodies (Beckton Dickinson UK Ltd, Cowley, UK) and CD80 and CD83 (Caltag Medsystems Lts, Towcester, UK), all of which were labelled with phycoerythrin (PE).

(ii) Cell Lines

The following cells lines were used HMEC-1 cells (CDC, Atlanta, Ga. 30333, U.S.A.), HAEo- cells (courtesy DC Gruenert, Human Molecular Genetics Unit, Department of Medicine, University of Vermont, Burlington, Vt. 05405, USA), Neuro-2a cells, also known as N2a cells (LGC Promochem, Teddington, Middlesex, UK), and HepG2 cells.

The human airway epithelial cell line (1HAEo-) was maintained in Eagle's Minimal Essential Medium (MEM) HEPES modification (Sigma, Poole, U.K.) supplemented with 10% foetal calf serum (FCS, Sigma, Poole, U.K.), 100 U/ml penicillin and 100 µg/ml streptomycin (InVitrogen, Paisley, U. K.) and 2 mM L-glutamine (InVitrogen, Paisley, U. K.).

The human microvascular endothelial cell line HMEC-1 was maintained in MCDB31 medium (InVitrogen, Paisley, U. K.) supplemented as for 1HAEo- cells but with 1 mg/L hydrocortisone (R & D Systems Europe Ltd, Abingdon, U. K.), 10 mg/L epidermal growth factor (EGF; Sigma, Poole, U.K).

The mouse neuroblastoma cell line Neuro-2A was maintained in Dulbecco's MEM with Glutamax-1 (InVitrogen, Paisley, U. K.) with 10% FCS, 1 mM sodium pyruvate (InVitrogen, Paisley, U. K.), 100 U/ml penicillin, 100 µg/ml streptomycin, and 0.1 mM non-essential amino acids.

The human hepatocarcinoma cell line HepG2 was maintained in Eagle's MEM containing Earle's Basic Salts Solution (BSS), 1.5 g/L sodium bicarbonate, 0.1 mM non-essential amino acids (Sigma, Poole, U.K.), and supplemented as for 1HAEo- cells except with 1 mM sodium pyruvate.

(iii) Generation of Macrophages

Monocytes were prepared from peripheral blood as described above. The mononuclear cells were plated into a 25 cm³ flask in 10% FCS, RPMI for 1-2 hours (1 flask per 10 ml blood) before removing the supernatant and adding fresh 10% FCS, RPMI+10 ng/ml MCSF (macrophage colony stimulating factor, R & D Systems). Half the media was replaced with fresh 10% FCS, RPMI+MCSF (10 ng/ml) after 48 hours and the cells were used at day 6, harvesting by scraping the cells from the well.

(iv) The Peptide Library

The library used, C7C, was obtained commercially from New England Biolabs Inc. Phage growth, titration and amplification procedures were performed as described in the manufacturer's handbook. The library consists of random peptide sequences seven residues in length and flanked by cystine residues to allow cyclisation. Constrained cyclic peptides often display higher binding affinities than their linear counterparts.

(v) Generation of Immature Human Dendritic Cells

Immature dendritic cells were generated from peripheral blood monocytes as described below. This method may be used to generate human and mouse dendritic cells.

10 ml or 40 ml samples of peripheral blood were diluted 1:1 with Hanks Buffered salt solution (HBSS; Gibco BRL-InVitrogen, Paisley, U.K.) then layered on Lymphoprep (Nycomed (UK) Ltd, Sheldon, Birmingham), centrifuged at 750 g for 30 min and lymphocytes were isolated from the interface. Excess Lymphoprep was removed by spinning the cells down at 250 g for 10 min, and any platelets present were removed by washing in HBSS twice, centrifuging the cells at 1200 rpm for 10 min each time. Monocytes were then isolated using MACs CD 14 magnetic microbeads (Miltenyi Biotec Ltd., Bisley, Surrey) as described in the manufacturer's protocol. Monocytes were seeded at $1 \times 10^6$ cells per well in a 6 well plate, in 3 ml per well complete medium (HEPES buffered RPMI (InVitrogen, Paisley, U.K.)+10% fetal calf serum (FCS Myclone low LPS, InVitrogen, Paisley, U.K.), 100 U/ml penicillin and 100 µg/ml streptomycin (complete medium)) supplemented with recombinant human GM-CSF (Granulocyte-macrophage colony-stimulating factor) (Leucomax) (purchased from Schering Plough/Sandoz, Innishannon, Ireland) and IL-4 (obtained from PreproTech EC Ltd, London, UK) cytokines (100 ng/ml and 25 ng/ml final concentrations, respectively) and incubated at 37° C., 5% $CO_2$. Fresh cytokines GM-CSF and IL-4 were added on day 3 of incubation and non-adherent immature dendritic cells were harvested on day 6 for viral transduction or day 3 or 4 for non-viral transduction.

(vi) Dendritic Cell Selection ("Panning") in Solution

Selection of dendritic cell binding phage from the peptide library ("panning"), was carried out as below using approximately $1 \times 10^6$ viable dendritic cells obtained by the method described in Example 1(iv) above per round in solution, and using $2 \times 10^{11}$ phage from the C7C library, see Example 1(i) above.

Before addition of the phage library to the cells, both were blocked for 30 min, each in 1 ml 2% Marvel (dried milk) 5% BSA-PBS (bovine serum albumin in phosphate buffered serum, pH7) at 4° C. in an up-and-over turntable (vertically rotating wheel) to reduce non-specific interactions. The phage were then allowed to bind to the cells for 2 hours at 4°

C. with mixing by rotation, before centrifuging the cells at 315 g (2000 rpm) for 3 min to remove the supernatant, which contains non-binding phage. The cells were then washed five times in 2% BSA-PBS, for five minutes each, transferring the cells to clean tubes each time to remove non-specific or weakly binding phage. Two washes in PBS only were then carried out, followed by elution using 76 mM citrate buffer pH 2.5 for 10 min with mixing in an up-and-over turntable (by vertical rotation). The cells were spun down, and the eluate removed, neutralised by the addition of 600 µl 1M Tris pH 7.5, and stored at 4° C. (the 'eluted fraction'). The remaining cells were lysed with 1 ml 30 mM Tris pH 8.0, 1 mM EDTA for 1 hour on ice, before vortexing briefly & storing at 4° C. for a phage titration later, see Example 1(vii)(b) below.

Harvested phage from each cell lysis fraction were titrated as plaque forming units (PFU) before amplification in *E. coli* ER2738 (New England Biolabs (UK) Ltd, Hitchin, Herts) as described in the manufacturer's instructions, titred and used as the input phage for the next round of panning. Three rounds of panning were carried out using dendritic cells from two different donors for each round to avoid isolating HLA-specific binding peptides. All panning was carried out at 4° C. or below to prevent alterations in the dendritic cell phenotype. For the second and third rounds of panning, the wash stringency may be reduced to three times with 2% BSA-PBS and twice with PBS only if low numbers of phage are harvested. Following titration of phase from the third round fractions, single, well-isolated plaques were picked, amplified and purified for sequencing and clone binding characterization by FACS or titration.

Phage were recovered and titred from each round of selection as follows. $2 \times 10^{11}$ Blocked phage were added to $5 \times 10^4$ blocked monocyte-derived immature dendritic cells for 1 hour on ice before washing cells three times with 0.05% Tween20-PBS, eluting phage with TBS pH5.5, and lysing cells to harvest the phage remaining bound. The numbers of phage harvested by cell lysis were calculated as plaque forming units (pfu). FIG. 1 shows results of some of the titrations. Sequencing of the bound phage shown in FIG. 1 identified the peptides as APSNSTA [SEQ. ID. NO.:15], QLLTGAS [SEQ. ID. NO.:30], TARDYRL [SEQ. ID. NO.:31], FQSQYQK [SEQ. ID. NO.:26], PLMPSLS [SEQ. ID. NO.:24], FPRAPHH [SEQ. ID. NO.:32], MASISMK [SEQ. ID. NO.:27], DWWHTSA [SEQ. ID. NO.:28], SHVKLNS [SEQ. ID. NO.:29], and SPALKTV [SEQ. ID. NO.:16].

(vii) Characterisation of Cell Binding of Selected Phage

Binding of phage to human monocyte-derived immature dendritic cells (Dendritic cells) was investigated by whole cell flow cytometry and phage titration assays.

(a) Whole Cell Flow Cytometry

Non-adherent immature human Dendritic cells produced as described in Example 1(v) above were harvested. $5 \times 10^4$ Dendritic cells and $2 \times 10^{11}$ of an individual purified phage clone were each blocked at 4° C. for 30 mins in 1 ml MBSA (2% Marvel, 5% BSA in PBS), with mixing on a turntable. The dendritic cells were spun down at 2000 rpm, a gentle centrifugation to pellet cells without lysing them, for 5 min at 4° C., and the pellet resuspended in the blocked phage solution. The mixture was held on ice for 30 min to allow the phage to bind, before spinning down the cells, removing the supernatant and washing the cells with 1 ml 1% BSA, 0.05% Tween20-PBS. The cells were spun again, the supernatant removed, and the cells fixed in 1 ml 1% paraformaldehyde for 30 min on ice. The cells were washed twice in PBS, resuspended in 1 ml 1% Marvel, 2.5% BSA in PBS and 2 µl of FITC(fluorescein-isothiocyanate)-labelled anti-Fd antibody (Sigma, Poole, Dorset) (3 mg/ml) added. The cells were incubated with the antibody on ice for 30 min before spinning down, washing twice in 0.05% Tween20, 1% BSA PBS, resuspending in 2000 PBS and measuring the percentage cells positive for FITC by FACS analysis.

Alternatively, $5 \times 10^4$ dendritic cells were mixed with $2 \times 10^{11}$ of individual phage clones as described for panning of the phage library. The mixture of phage and DC suspensions was kept on ice for 30 min before cells were centrifuged to remove the supernatant and washed with 1 ml 1% BSA, 0.05% Tween 20-PBS. The cells were again pelleted by centrifugation, then fixed for flow cytometry analysis by resuspending in 1 ml of 1% paraformaldehyde for 30 min on ice. Fixed dendritic cells were washed twice in PBS, resuspended in 1 ml 1% Marvel, 2.5% BSA in PBS and mixed with 2 µl of FITC-anti-fd phage antibody solution at 3 mg/ml (Sigma, Poole, U. K.). The cells were incubated with the antibody on ice for 30 min then pelleted by centrifugation, washed twice in 0.05% Tween 20, 1% BSA PBS and resuspended in 200 µl PBS. The percentage of FITC-positive cells was determined by flow cytometry using a Epics XL flow cytometer (Beckman Coulter, High Wycombe, UK.).

(b) Titration of Phage Clone Binding to Cells

For each titration $5 \times 10^4$ monocyte derived-dendritic cells (day 5 or day 6) were initially blocked by incubating in 200 µl blocking buffer (DMEM/2% Marvel/1% BSA) for 30 min at 4° C., mixing constantly. $2 \times 10^{11}$ Phage were also blocked in 200 µl blocking buffer for 30 min at 4° C. The dendritic cells were spun down at 2000 rpm, for 5 min at 4° C., and resuspended in the phage solution, allowing the phage to bind for 1 hour on ice with occasional mixing. The cells were then washed in PBS-Tween 20 (0.05%) three times before eluting phage with 166 µl TBS pH5.5. for 10 min on ice. The eluate was neutralised with 34 µM Tris-HCl pH 8, the cells were spun down, and the supernatant removed to be stored as eluate. The cell pellet was resuspended in 200 µl of cell lysis buffer (30 mM Tris-HCl, 1 mM EDTA pH 8.0) for 1 hour on ice, with shaking. The cell debris was removed by spinning at 5000 rpm for 5 min and the supernatant recovered. The phage in the eluate and the cell lysate were titred by measuring plaque forming units (pfu) in *E. coli* ER2738 as described in the NEB C7C technical bulletin.

The titration of phage clone binding was carried out using human and mouse dendritic cells, with binding to plastic as a control. The human cells were obtained from donors as stated below.

(c) Sequencing Phage Peptide Inserts

81 Individual phage clones isolated from the cell lysis fraction following the third round of dendritic cells selection were purified from small scale polyethylene glycol (PEG) preparations (see NEB C7C technical bulletin, and single stranded phage DNA was prepared for sequencing [Kay, 1996 #50].

Briefly, the protein coat was removed from the sample by phenol chloroform extraction, and the DNA pelleted by ethanol precipitation. Trace salt was washed from the pellet with ice cold 70% ethanol before resuspending the DNA in Tri-EDTA (TE) (10 mM Tris Hcl, ImMEDIA, pH7.5). From 50 to 100 ng purified DNA was used in a Big Dye (Applied Biosystems, Foster City, Calif., USA) terminator cycle sequencing reaction (following the manufacturers instructions) using the −96 primer (5'-CCCTCATTAGCGTAACG-3') [SEQ. ID. NO.:56] (supplied with the C7C library) and purified for loading by ethanol precipitation as described in the kit instructions. The samples were run on an ABI 377 sequencer (Applied Biosystems, Foster City, Calif., USA) and the results were analysed using the Vector NTI Suite of programs (Informax Inc, Oxford UK).

Results

Peptide Identification

"Panning" was carried out as described in Example 1(vi) to obtain titrations of the phage. FIG. 1 shows results of some of the titrations. Sequencing of the bound phage shown in FIG. 1 identified the peptides as APSNSTA [SEQ. ID. NO.:15], QLLTGAS [SEQ. ID. NO.:30], TARDYRL [SEQ. ID. NO.: 31], FQSQYQK [SEQ. ID. NO.:26], PLMPSLS [SEQ. ID. NO.:24], FPRAPHH [SEQ. ID. NO.:32], MASISMK [SEQ. ID. NO.:27], DWWHTSA [SEQ. ID. NO.:28], SHVKLNS [SEQ. ID. NO.:29], and SPALKTV [SEQ. ID. NO.:16].

Sequencing of 81 phage clones from the cell-associated fraction from the third round of titration of phages clone binding to immature dendritic cells identified 16 different sequences, see Table 2.

TABLE 2

Phage sequences from third round of titration of phage clone binding to immature dendritic cells.

| Sequence | Number of clones | Percentage of clones | SEQ. ID. NO. |
|---|---|---|---|
| APSNSTA | 17 | 21 | 15 |
| DWWHTSA | 16 | 20 | 28 |
| SHVKLNS | 10 | 12 | 29 |
| SQKNPQM | 6 | 7 | 25 |
| QLLTGAS | 5 | 6 | 30 |
| SPALKTV | 5 | 6 | 16 |
| FQSQYQK | 5 | 6 | 26 |
| TARDYRL | 4 | 5 | 31 |
| FPRAPHH | 4 | 5 | 32 |
| STPPNTT | 3 | 4 | 17 |
| PMLPSLS | 1 | 1 | 24 |
| SEWLSAL | 1 | 1 | 33 |
| IGGIRRH | 1 | 1 | 34 |
| YTMEFNR | 1 | 1 | 35 |
| MASISMK | 1 | 1 | 27 |
| PAAYKAH | 1 | 1 | 36 |

The three most frequent phage clones are present at 21% (APSNSTA) [SEQ. ID. NO.:15], 20% (DWWHTSA) [SEQ. ID. NO.:28] and 12% (SHVKLNS) [SEQ. ID. NO.:29] with the remainder present at 7% and below. Analysis of the 16 binding sequences from the phage clones identified five minimal motifs, namely, $PXN^T/_ST$ [SEQ. ID. NO.:40], $PXXXT^A/_V$ [SEQ. ID. NO.:37], $^A/_LPSXS$ [SEQ. ID. NO.:4], $S^L/_IS$ [SEQ. ID. NO.:43], and $QX^N/_QXQ$ [SEQ. ID. NO.:42], see Table 3, which motifs may play an important role in binding to receptors on dendritic cells. Of all the clones sequenced, 46% contained one or more motifs, with the most frequent clone, APSNSTA [SEQ. ID. NO.:15], showing a degree of homology to three other peptide sequences, see Table 3.

TABLE 3

Conserved amino acid motifs in peptide sequences

| Peptide Homology | Motif | % clones containing motif |
|---|---|---|
| A*PSNTA* [SEQ. ID. NO.:15] S*PALKTV* [SEQ. ID. NO.:16] | PXXXT$^A/_V$ [SEQ. ID. NO.:37] | 27 |

TABLE 3-continued

Conserved amino acid motifs in peptide sequences

| Peptide Homology | Motif | % clones containing motif |
|---|---|---|
| ST*PPNTT* [SEQ. ID. NO.:32] A*PSNSTA* [SEQ. ID. NO.:15] S*PALKTV* [SEQ. ID. NO.:16] | PX$^N$/LXT [SEQ. ID. NO.:39] | 31 |
| A*PSNSTA* [SEQ. ID. NO.:15] PM*LPSLS* [SEQ. ID. NO.:24] | $^A/_L$PSXS [SEQ. ID. NO.:41] | 22 |
| S*QKNPQM* [SEQ. ID. NO.:25] F*QSQYQK* [SEQ. ID. NO.:26] | QX$^N/_Q$XQ [SEQ. ID. NO.:42] | 13 |
| PMLP*SLS* [SEQ. ID. NO.:24] MA*SISMK* [SEQ. ID. NO.:27] | S$^L/_I$S [SEQ. ID. NO.:43] | 2 |

Identical amino acids are shown in bold and italic
Similar amino acids are shown in italic only Titrations of phage clone binding to dendritic cells in most cases showed that the clones bind to a greater extent to the cells than do phage that have no insert in the cells. Two clones, FPRAPHH [SEQ. ID. NO.:32] and MASISMK [SEQ. ID. NO.:27] bound in highest numbers in all titrations, including the titration of phage binding to mouse dendritic cells. The numbers of phage binding to plastic was low for all clones tested, suggesting that phage binding demonstrated by high titres in these experiments is due to binding to cells and not background non-specific binding to the wells or blocking molecules, see FIG. 1 and Table 4.

TABLE 4

Titration of phage binding to human dendritic cells, mouse dendritic cells and blocked plastic

| Peptide displayed on phage | human donor JD | Human donor S | Human donor LA | Mouse DCs | Plastic | SEQ. ID. NO. |
|---|---|---|---|---|---|---|
| APSNSTA | 460 | 6480 | 1920 | 480 | 480 | 15 |
| QLLTGAS | 960 | 220 | 380 | 20 | 220 | 30 |
| TARDYRL | 180 | 940 | N/D | N/D | N/D | 31 |
| FQSQYQK | 360 | 3060 | 1000 | 3260 | 1680 | 26 |
| PMLPSLS | 40 | 560 | 40 | 1520 | 80 | 24 |
| FPRAPHH | 3200 | 19400 | 15920 | 13980 | 1860 | 32 |
| MASISMK | 7780 | 9440 | 15220 | 6380 | 2380 | 27 |
| DWWHTSA | 1380 | 8020 | 2980 | 3240 | 1180 | 28 |
| SHVKLNS | 1160 | 7280 | 2620 | 2120 | 720 | 29 |
| SPALKTV |  | 6960 | 120 | 600 | 220 | 16 |
| None | 1400 | 240 | 80 | 100 | 5.6 |  |

Figures shown ×10$^3$

FACS analysis of phage binding to dendritic cells from different human dendritic cell donors with six of the most frequent clones namely APSNSTA [SEQ. ID. NO.:15], FQSQYQK [SEQ. ID. NO.:26], DWWHTSA [SEQ. ID. NO.:28], SHVKLNS [SEQ. ID. NO.:29], SPALKTV [SEQ. ID. NO.:16], and SQKNPQM [SEQ. ID. NO.:25] showed that all clones except for one, SPALKTV [SEQ. ID. NO.:16], were detected binding to a higher percentage of cells than a phage clone bearing no insert, see FIGS. 2a and 2b.

The pattern of binding identified the three clones binding to dendritic cells in highest amounts as those containing the peptides APSNSTA [SEQ. ID. NO.:15], DWWHTSA [SEQ. ID. NO.:28] and SHVKLNS [SEQ. ID. NO.:29], which clones were also the three most frequently isolated from the selection. For the second set of six clones tested, namely those containing the peptides QLLTGAS [SEQ. ID. NO.:30], TARDYRL [SEQ. ID. NO.:31], PMLPSLS [SEQ. ID. NO.:24], FPRAPHH [SEQ. ID. NO.:32], MASISMK [SEQ. ID. NO.:27], and STPPNTT [SEQ. ID. NO.:17], all clones showed a higher percentage of cells positive for bound phage than the controls with no insert. QLLTGAS [SEQ. ID. NO.:30] binds to marginally more cells than the others, see FIGS. 3a and 3b.

Of the 16 phage sequences five, namely APSNSTA [SEQ. ID. NO.:15], SHVKLNS [SEQ. ID. NO.:29], MASISMK [SEQ. ID. NO.:27], FPRAPHH [SEQ. ID. NO.:32] AND DWWHTSA [SEQ. ID. NO.:28], were chosen for synthesis on the basis that they were among the most frequent clones and also were among the top binders in the FACS assay of phage clone binding.

Example 2

Non-Viral Transfection

Materials and Methods (i) Peptide Synthesis

Peptides A, B, C, D and F (see Table 7), identified from phage that display desirable cell binding and entry characteristics, see Example 1, were synthesised using standard synthetic chemistry with a sixteen-lysine tail, a GAC linker, and a C-terminal CG group. Peptide 6, RRETEWA [SEQ. ID. NO.:53], is an integrin-binding peptide. Peptide 6J, ATRWARE [SEQ. ID. NO.:57], is a scrambled version of peptide 6, and serves as a control peptide. The term "peptide derivative" is used to denote the synthesized peptide sequence shown below i.e. "peptide A" denotes SHVKLNS [SEQ. ID. NO.:29] and "peptide A derivative" denotes $[K]_{16}$-GACSHVKLNSCG [SEQ. ID. NO.:44]. Details of the peptides and peptide derivatives are given in Table 5 below.

TABLE 5

Peptides and peptide derivatives

| Peptide name | Peptide sequence | Peptide derivative sequence |
|---|---|---|
| A | SHVKLNS [SEQ. ID. NO.:28] | $[K]_{16}$-GACSHVKLNSCG [SEQ. ID. NO.:44] |
| B | APSNSTA [SEQ. ID. NO.:16] | $[K]_{16}$-GACAPSNSTACG [SEQ. ID. NO.:45] |
| C | MASISMK [SEQ. ID. NO.:27] | $[K]_{16}$-GACMASISMKCG [SEQ. ID. NO.:46] |
| D | FPRAPHH [SEQ. ID. NO.:32] | $[K]_{16}$-GACFPRAPHHCG [SEQ. ID. NO.:47] |
| F | DWWHTSA [SEQ. ID. NO.:28] | $[K]_{16}$-GACDWWHTSACG [SEQ. ID. NO.:48] |
| 6 | RRETAWA [SEQ. ID. NO.:53] | $[K]_{16}$-GACRRETAWACG [SEQ. ID. NO.:49] |
| 6J |  | $[K]_{16}$-GACATRWARECG [SEQ. ID. NO.:50] |

(ii) Formation of Lipopolyplex (LID) Transfection Complexes and Transfection of Immature Dendritic Cells (a) Transfection Complexes for Immature Dendritic Cells Lipopolyplex (LID) transfection complexes comprising lipid (L), peptide (in the form of a peptide derivative as described above) (I) and DNA (D) were prepared. The lipid component was Lipofectin or Lipofectamine 2000 (Invitrogen Ltd, Paisley, UK), the peptide component was a synthesized peptide A to F, 6 or 6J derivative, as described in Table 7 above, and the DNA was the plasmid pEGFP-N1 (Clontech, BD Biosciences, Palo Alto, Calif.)

In the transfection complex, peptide component to DNA charge ratios (+/−) were used at 1.5:1, 3:1 and 7:1. The lipid component (Lipofectin or Lipofectamine 2000) was maintained at a constant proportion, by weight, relative to DNA of 0.75:1. Prior to making transfection complexes, in method A the lipid component was diluted to a concentration of 15 µg per ml, the peptide was prepared at 0.1 mg/ml and the DNA (plasmid pEGFP-N1, BD Biosciences, Cowley, UK, prepared using EndoFree plasmid kit, Qiagen Ltd, Crawley, UK) was at 10 µg per ml. All dilutions were performed with Opti-MEM reduced serum tissue culture medium (Life Technologies Ltd, Paisley, UK). In method B prior to making transfection complexes the lipid component was diluted to a concentration of 30 µg per ml, the peptide was prepared at 0.1 mg/ml and the DNA (plasmid pEGFP-N1, BD Biosciences, Cowley, UK, prepared using EndoFree plasmid kit, Qiagen Ltd, Crawley, UK) was at 40 µs per ml. All dilutions were performed in serum-free RPMI.

Transfection complexes were made by mixing the components in the order 1) lipid (50 µl) then 2) peptide (70 µl) and finally 3) DNA (50 µl), then diluting with OptiMEM or serum free RPMI, as appropriate, to a concentration relative to the DNA component of 2 µg DNA per 3000 (OptiMEM) or 500 µl (RPMI).

(b) Transfection of Immature Dendritic Cells & Monocytes

Immature day 6 dendritic cells, obtained as described in Example 1(v) above, were plated into a 48 well plate at $5 \times 10^4$ cells per well in complete media and allowed to settle for 3 hours at 37° C. 300 µl or 500 µl (as appropriate) of the transfection complex obtained as described above was added to each well. The transfection complex was applied to cells within 5 minutes of preparation. Transfection incubations were performed at 37° C. for 4 hours, after which the medium was replaced with complete medium with cytokines for 24 hours. Cells were harvested by scraping, spun down and resuspended in 300 µl PBS for FACS analysis to determine the percentage of cells positive for the reporter gene EGFP (Enhanced Green Fluorescent Protein). Each transfection was performed in triplicate wells.

For transfection of monocytes, peripheral blood monocytes were prepared using Lymphoprep centrifugation and CD14 bead selection as described in the method for preparation of monocyte derived dendritic cells in Example 1(v) above. These cells were then transfected as described as described for dendritic cells except that transfection of the monocytes (and also of day 3 or day 4 immature dendritic cells) was carried out in solution.

(iii) Transfection of Other Cell Types (a) Other Cell Types

The other cells types used were HMEC-1 cells (CDC, Atlanta, Ga. 30333, U.S.A), HAEo- cells (courtesy DC Gruenert, Human Molecular Genetics Unit, Department of Medicine, University of Vermont, Burlington, Vt. 05405, USA) and Neuro-2a cells, also known as N2a cells (LGC Promochem, Teddington, Middlesex, UK).

(b) Transfection Complexes for Other Cell Types

Transfection complexes comprising lipid, peptide and DNA were prepared. The lipid component was lipofectin (Invitrogen Ltd, Paisley, UK), the peptide component was a peptide A to F, 6 or 6J derivative, as described above, and the DNA was the plasmid pCILuc (Promega UK Ltd, Southampton). In the transfection complex, peptide to DNA charge ratios (+/−) were used at 3:1, 5:1 and 7:1. The lipid component was maintained at a constant proportion, by weight, relative to DNA of 0.75:1. Prior to making transfection complexes the lipid component was diluted to a concentration of 15 μg or 30 μg per ml, the peptide was prepared at 0.1 mg/ml and the DNA was at 40 μg per ml. All dilutions were performed with Opti-MEM reduced serum tissue culture medium (Life Technologies). Transfection complexes were made by mixing of components in the order 1) lipid then 2) peptide and finally 3) DNA, then diluted with OptiMEM to a concentration relative to the DNA component of 0.25 μg DNA per 2004

(c) Transfection of Other Cell Types

For transfection of these types of cell i.e. HMEC, HAEo-, N2a and HepG2, $1 \times 10^4$ cells were seeded overnight in 96 well plate. 200 μl of the suspension of the transfection complex prepared according to (b) above was added to each well. The suspension was applied to cells within 5 minutes of preparation. Transfection incubations were performed at 37° C. for 4 hours, after which the medium was replaced with the appropriate complete medium for 24 hours. Each transfection was performed in replicates of six.

Luciferase reporter gene assays in cell free extracts were performed after incubation for 24 hours using the luciferase assay from Promega UK Ltd using the manufacturer's protocol. Light units were standardised to the protein concentration within each extract.

(iv) Phenotyping of Transfected Dendritic Cells

Immature day 4 dendritic cells were transfected with LID complex with peptide A at a charge ratio 7:1 to the DNA (plasmid pEGFP-N1), with lipofectin added at a weight ratio of 0.75 to the DNA for 4 hours in RPMI before incubating in complete medium with cytokines for 24 hours. As a control, dendritic cells were incubated in complete medium for 24 hours (immature Dendritic cells) Cells were then harvested by scraping and stained for the presence of maturation markers as follows: a minimum of $5 \times 10^4$ cells in a volume of less than 2 ml medium were added to the recommended amount of antibody and incubated for 20 min on ice. 2 ml of ice-cold PBS was added before centrifugation at 300×g for 5 min at 4° C. The supernatant was flicked off and the pellet resuspended in 300 μl ice cold 1% paraformaldehyde-PBS. Cells from each sample were stained with antibodies to HLA-DR, and CD86 and isotype matched control antibodies. Cells were analysed by flow cytometry using a Epics XL (Beckman Coulter, High Wycombe, UK.) and the EXPO32 analysis software (Beckman Coulter).

(v) Maturation and Phenotyping of Transfected Dendritic Cells

Immature day 4 dendritic cells were transfected with LID complex with peptide D at a charge ratio 7:1 to the DNA (plasmid pEGFP-N1), with lipofectin added at a weight ratio of 0.75 to the DNA for 4 hours in RPMI (as described previously). In one sample LPS was added to the complete medium at a concentration of 50 ng/ml immediately after transfection for 24 hours, in the other, cells were incubated in complete medium for 2 days before adding LPS for a further 24 hours. As a control, dendritic cells were incubated in complete medium for 24 hours (immature DCs) or in complete medium with LPS (mature DCs). Cells were then harvested by scraping and stained for the presence of maturation markers as follows: a minimum of $5 \times 10^4$ cells in a volume of less than 2 ml medium were added to the recommended amount of antibody and incubated for 20 min on ice. 2 ml of ice-cold PBS was added before centrifugation at 300×g for 5 min at 4° C. The supernatant was flicked off and the pellet resuspended in 300 μl ice cold 1% paraformaldehyde-PBS. Cells from each sample were stained with antibodies to HLA-DR, and CD86 and isotype matched control antibodies. Cells were analysed by flow cytometry using a Epics XL (Beckman Coulter, High Wycombe, UK.) and the EXPO32 analysis software (Beckman Coulter).

Results

The constrained peptides synthesised with a DNA-binding $[K]_{16}$ [SEQ. ID. NO.: 54] domain were tested for their ability to transfect immature dendritic cells in a lipopolyplex (LID) transfection complex with DNA and lipid. The results are shown in FIG. 4.

A comparison of transfection efficiencies of all five peptides synthesised derivates A, B, C, D and F in the LID format using lipofectin and transfecting day 4 dendritic cells, identified peptides A, B and D as giving the best transfection efficiencies, all transfecting over 10% of dendritic cells, with peptide C giving approximately half that value, and peptide F performing poorly, with less than 1% of cells transfected, see FIG. 4b.

Transfection efficiency, as measured by the percentage cells positive for the reporter gene EGFP determined by FACS, was increased by the use of the phage derived peptide A (SHVKLNS) [SEQ. ID. NO.:29] to a level approximately one and a half times that of the positive control, peptide 6, the integrin binding peptide RRETAWA [SEQ. ID. NO.:53] and the negative control, peptide 6J, (the scrambled version of peptide 6). Peptide B (APSNSTA) [SEQ. ID. NO.:15] produced transfection levels equal to those of peptide 6. The percentage of cells transfected did not reach 5%, possibly due to the toxic effect of the transfection procedure on the dendritic cells.

The four constrained peptides A, B, C and D synthesised with a DNA-binding $[K]_{16}$ [SEQ. ID. NO.:54] domain, were tested for their ability to transfect day 4 immature dendritic cells in a lipopolyplex (LID) transfection comprising commercially available lipids lipofectin and lipofectamine, see FIG. 5a. Where lipofectin was used, all peptides produced transfection efficiencies above that of peptide 6 (an integrin binding peptide). Peptide A produced the highest efficiency of 17%, with peptides B and D giving 11% positive cells, C producing about 7% positive, only just above the 2% achieved with peptide 6 and no peptide control. Where no lipid was used, transfection was less than 1% for peptide A, demonstrating the importance of the lipid for the efficacy of the complex.

Lipofectamine 2000 produced generally lower transfection efficiencies than lipofectin, between 5 and 8%, except for peptide 6, which provided 3% positive cells. Toxicity was high in all cases, see FIG. 5b, at between 40 and 53%, with the lipofectin giving similar levels of toxicity to Lipofectamine 2000, except in the case of peptide C and no peptide, where Lipofectamine 2000 is noticeably more toxic than lipofectin. This toxicity can vary between experiments, with lipofectin resulting in cell death in the range 17 to 46%, and Lipofectamine 2000 in the range 26 to 53%. When metafetene was used in accordance with the manufacturers' instructions, a much higher level of cell death was seen, between 78 and 84%, data not shown, suggesting choice of lipid can seriously affect cell death following transfection.

Transfection efficiencies of day 3 dendritic cells were considerably lower than day 4 dendritic cells, at 7% EGFP positive cells and lower, except for the control, peptide 6 which gave an efficiency of 14%, see FIG. 6a. Cell death was high in all samples, at between 28 and 48%, with Lipofectin being slightly less toxic than Lipofectamine 2000, see FIG. 6b.

Transfection of monocytes using the targeting peptides gave comparable efficiencies to transfections using peptide 6, with peptides A, B and D again giving highest percentages of cells transfected, see FIG. 7a, although levels were lower than day 4 dendritic cells, with only 6% being the highest percent positive for EGFP (peptide A combined with lipofectin). Toxicity was fairly low in most cases, at between 5 and 14% cell death, see FIG. 7b, except where peptide F or no peptide was used in conjunction with lipofectin, where cell death rose to 25% and 20% respectively. Interestingly these were the conditions where transfection efficiency was lowest.

Transfection of immature day 4 dendritic cells resulted in upregulation of HLA-DR and CD86 molecules on the cells surface, see FIG. 8, indicating that activation of the dendritic cells is occurring. Both the EGFP positive and negative cells display upregulated markers, and not all transfected dendritic cells show upregulated markers, suggesting the transfection process and not expression of EGFP is responsible for activation.

Maturation of dendritic cells following transfection using LPS showed a similar degree of upregulation of HLA-DR and CD86 to the transfected dendritic cells without LPS, but with a lesser degree of activation compared to untransfected dendritic cells incubated with LPS, suggesting that transfection may have a slightly inhibitory effect on activation, see FIG. 9. Addition of LPS to day 4 or day 6 cells had little effect on activation levels, with CD86 showing slightly less activation when cells were incubated with LPS on day 6 compared to day 4.

For the other cell types, the transfection efficiency was measured by luciferase activity per mg of protein present. In all cell lines tested, namely HMEC-1, HAEo- and N2a cells, at least one of the peptides produced transfection efficiencies equal to or above those seen with peptide 6.

Figure 10:
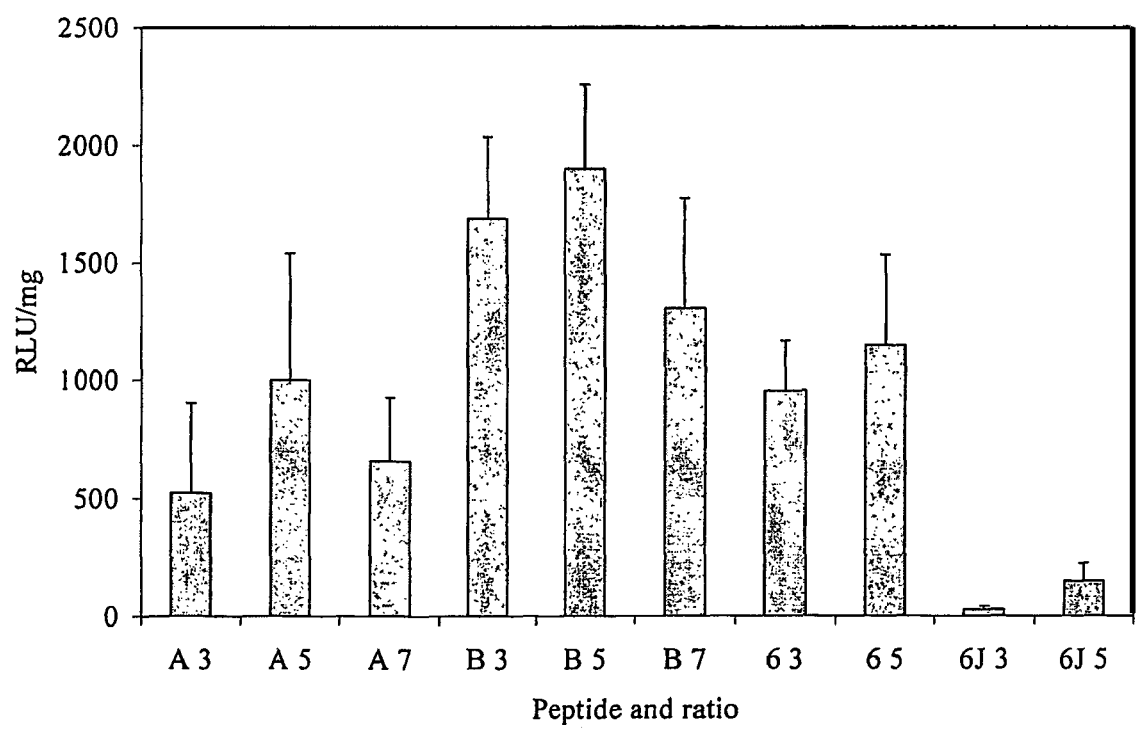
FIG. 10 shows transfection of HMEC-1 cell line with phage-derived peptide A and B derivatives (see the legend to FIG. 4 above). The results are given in RLU/mg, RLU denoting relative light unit. Transfection of cells with peptide A and B derivatives and the control peptide 6 derivative and its scrambled control peptide 6J was carried out with a range of peptide:DNA charge ratios including 3:1, 5:1 and 7:1 (A3, A5, A7, B3, B5, and B7, 6 3, 6 5 and 6J 5). Controls include cells with no transfection complexes added (OptiMEM only), cells transfected with an integrin binding peptide (peptide 6 derivative), and cells transfected with peptide 6J derivative, peptide 6J being the scrambled control of peptide 6. Each result is the percentage GFP positive cells from 3 pooled transfection reactions. Each result is the mean of 6 values and error bars represent the standard deviation about the mean.

In HMEC-1 cells, whilst peptide A produces a transfection efficiency approximately equal to that seen with peptide 6, peptide B can increase efficiency by one and a half times that of peptide 6, see FIG. 10.

Figure 11:
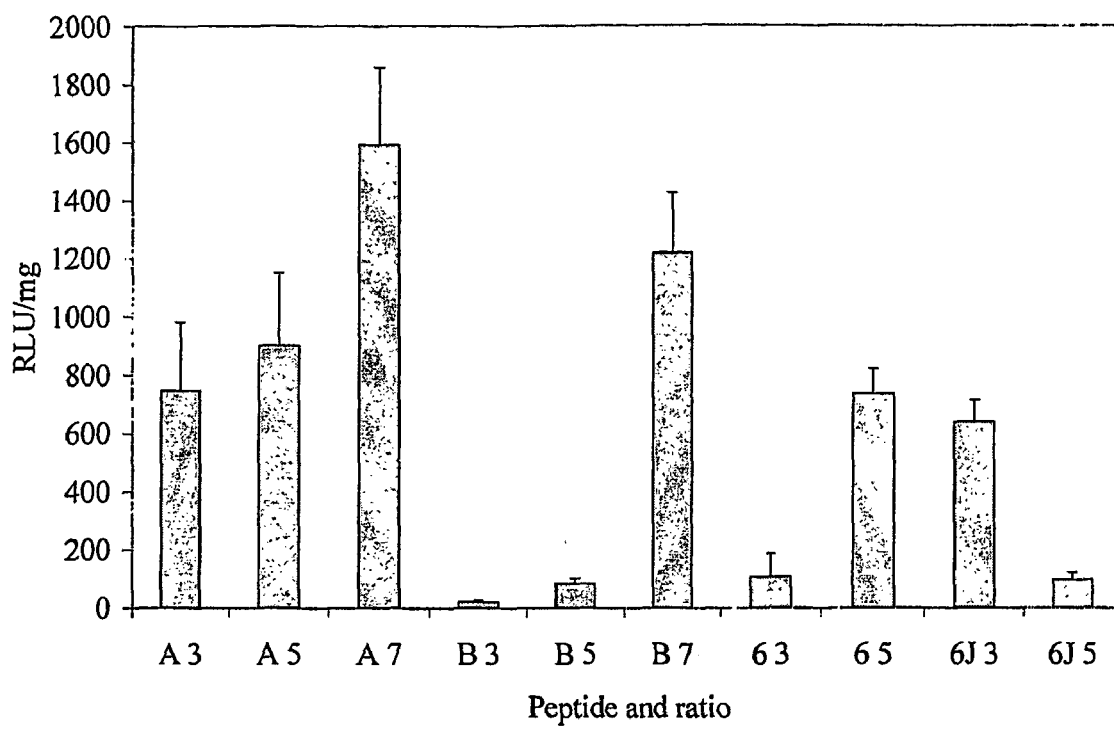
FIG. 11 shows transfection of HAEo- cell line with phage-derived synthesised peptides and controls as described for FIG. 10.

In HAEo- cells, peptide A produced the highest efficiency of transfection, approximately double that seen with peptide 6, whilst efficiency using peptide B was one and a half times that using peptide 6, see FIG. 11.

Figure 12:
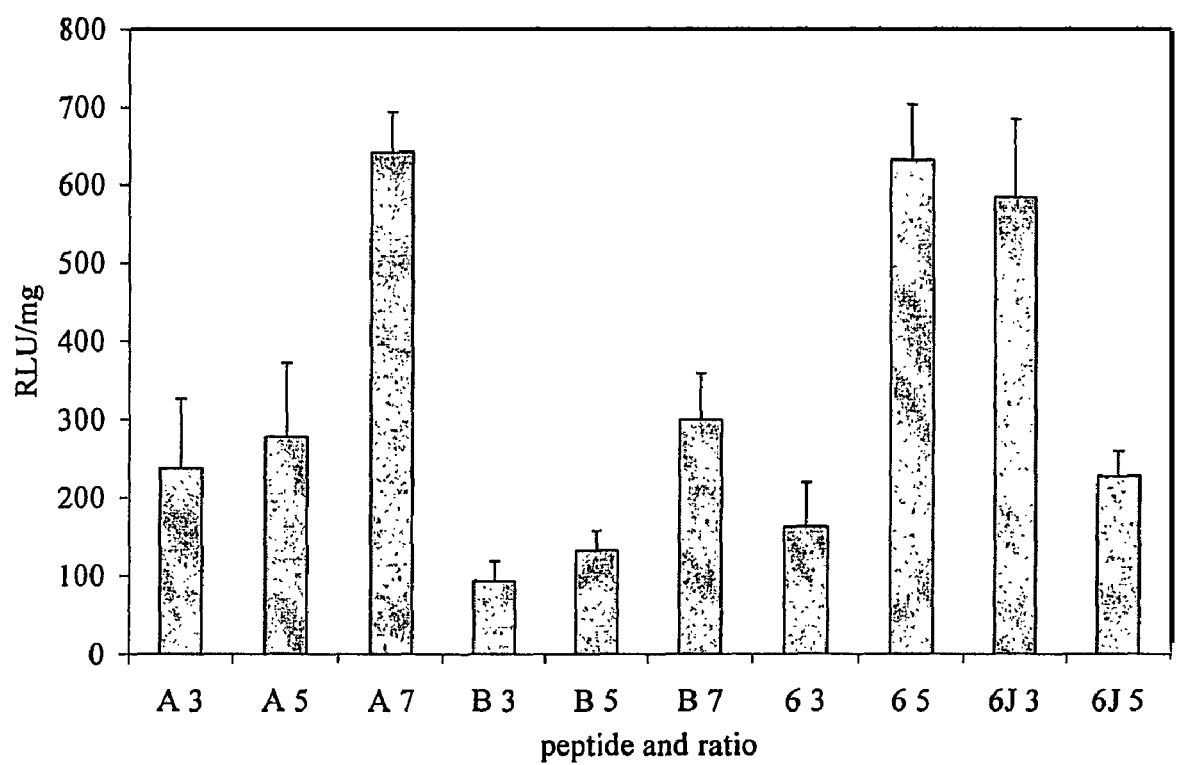
FIG. 12 shows transfection of N2a (Neuro2A) murine cell line with phage-derived synthesized peptides and controls as described for FIG. 10.

In Neuro2A (N2a) cells, only peptide A produced transfection efficiencies equal to those seen with peptide 6, with peptide B producing efficiencies of less than half that value, see FIG. 12.

Example 3

Retargeting Adenovirus

Materials and Methods (i) Mouse Bone Marrow Derived Dendritic Cells

Mouse dendritic cells were prepared from whole bone marrow flushed from the marrow cavities of the femur and tibia of 5-7 week old A/J mice and cultured in Hepes buffered RPMI+Glutamax (InVitrogen, Paisley, U. K.) supplemented with 10% FCS, penicillin/streptomycin and 20 ng/ml recombinant GM-CSF. Cytokines were added to the same concentration on day 3 and the dendritic cells isolated from the floating cell fraction by MACs CD11c microbeads (Miltenyi Biotec, Bisley, U. K.) on day 6.

(ii) Mouse Sca1+ve Stem Cells

Mouse bone marrow cells were isolated as above and Sca1+ve cells were isolated using MACs Sca1 microbeads (Miltenyi Biotec, Bisley, U.K.). These cells were plated at $7\times10^4$ cells/500 µl in RPMI with Glutamax-1 containing 30% FCS and penicillin/streptomycin and the following cytokines murine SCF (50 ng/ml; Preprotech, London, UK), IL-6 (20 ng/ml; Preprotech, London, UK) and Flt3-L (10 ng/ml) (R&D Systems, Oxford, U. K.).

(iii) Retargeted Adenovirus/Recombinant Adenovirus Production and Quantitation

Retargeted adenovirus type 5 (Ad5) having a peptide A to F or inserted into the HI region of the fibre protein of the capsid were constructed and produced in the laboratory of Dr Dan von Seggern, Scripps Research Institute, California, USA using the method described in Nicklin 2001 Mol Ther 2001 Dec.; 4(6):534-42.

Ad5 particles with the DC-binding peptides incorporated into the HI loop of the fibre protein were produced essentially as described previously [12]. Complementary oligonucleotides encoding the peptide sequences SHVKLNS [SEQ. ID. NO.: 29] (5' CC GGA AGC CAC GTG AAG CTG AAC AGC G 3' [SEQ. ID. NO.:58] and 5' CC GGC GCT GTT CAG CTT CAC GTG GCTT 3'[SEQ. ID. NO.:59]) or APSNSTA [SEQ. ID. NO.:15] (5' CC GGA GCC CCC AGC AAC AGC ACC GCC G 3' [SEQ. ID. NO.:61] and 5' CC GGC GGC GGT GCT GTT GCT GGG GGCT 3' [SEQ. ID. NO.:62]) were synthesized (Operon Technologies, Alameda Calif. U.S.A.). The oligo pairs were then kinased, annealed, and ligated into the unique BspE1 site of pDV137 [12], an expression construct encoding an Ad5 fibre protein with a double point mutant (KO1) which blocks CAR binding and a linker/restriction site in the HI loop, to create pDV178 (SHVKLNS) and pDV179 (APSNSTA). Following sequence confirmation, the plasmids were used to trans-complement the fibre-deleted vector Ad5.GFP.δF[18] by transient transfection into 293 cells as described [19]. Viral particles were purified by freeze/thaw lysis and CsCl gradient centrifugation and dialyzed into 40 mM TRIS-pH 8.1/0.9% NaCl/10% glycerol and stored at −80° C. Virus was quantified by protein assay (BioRad, Hercules Calif., U.S.A.) against BSA standards and using the relation 1 µg viral protein=$4\times10^9$ viral particles.

(iv) Transduction Using Adenovirus

Retargeted adenoviruses carrying a peptide A or B were used for the transduction experiments described below. Wild type adenovirus type 5 and type 5 adenovirus having a KO1 fibre, all supplied by Dr Dan von Seggern, and as described in Nicklin 2001 Mol Ther 2001 Dec.; 4(6):534-42), were used as controls.

(a) Transduction of Dendritic Cells

Day 6 dendritic cells (see Example 1(v) above), or mouse bone marrow derived dendritic cells or mouse Sca1+ve stem cells, see (i) and (ii) above, were plated at $5\times10^4$ cells per well in a 48 well plate in 500 µl complete medium and allowed to settle for 3 hours at 37° C. Transductions were carried out in complete media, with virus being added at 100,000 viral particles/cell for 24 hours. Cells were harvested by scraping, spun down at 650 g (2000 rpm) for 5 min, resuspended in 300 µl PBS, and kept on ice before analysis. Viral transduction as determined by percentage of GFP positive cells was measured by FACS analysis. To measure percentage viability, 10 µl of 7-amino-actinomycin D (7AAD; Sigma, Poole, Dorset) was added immediately prior to analysis. Viral transduction of macrophages was carried out at 10,000 particles/cell in medium containing 2.5% FCS. For other cell types, cells were seeded overnight at $5\times10^4$ cells per well in 24-well plates in the appropriate media. Adenovirus was added in OptiMEM at 10,000 viral particles/cell, 1 ml per well in triplicate and incubated for 24 h at 37° C. Cells were then washed twice in PBS, trypsinised, triplicate wells pooled, spun down at 350×g for 5 min and resuspended in 300 µl PBS before analysis by flow cytometry where cell viability was to be measured, 10 µl 7AAD was added just prior to analysis.

Cells were pooled from three separate transduction experiments for the calculation of results.

(b) Transduction of Human Primary Macrophages

Primary macrophages were generated from peripheral blood monocytes as described below.

10 mls of peripheral blood were diluted 1:1 with HBSS then layered on Lymphoprep (Nycomed), spun at 750 g for 30 min and purified lymphocytes were isolated from the interface. Excess Lymphoprep was removed by spinning cells down at 250 g for 10 min and any platelets present were removed by washing in HBSS twice, spinning the cells at 1200 rpm for 10 min each time. Monocytes were then isolated using MACs CD14 microbeads as described in the manufacturer's protocol. The mononuclear cells were plated into a 25 cm³ flask in 10% FCS, RPMI for 1-2 hours (1 flask per 10 ml blood) before removing the supernatant and adding fresh 10% FCS, RPMI+10 ng/ml MCSF (macrophage colony stimulating factor). Half the medium was replaced with fresh 10% FCS, RPMI+MCSF (10 ng/ml) after 48 hours and the cells were used at day 6, harvesting by scraping the cells from the well.

Viral transduction was carried out at 10,000 particles/cell in medium containing 2.5% FCS. Viral transduction as determined by percentage of GFP positive cells was measured by FACS analysis. Cells were pooled from three separate transduction experiments for the calculation of results.

(c) Transduction of Other Cell Types

N2a cells, HAEo- cells, HMEC-1 cells and HepG1 cells were transduced with the retargeted adenovirus. The N2a, HMEC-1 and HAEo- cells were obtained from the sources described in Example 2(iii)(a) above. The HepGl cells were obtained from LGC Promochem, Teddington, Middlesex, UK.

For transduction of these other cell types, cells were seeded overnight at 5×10⁴ cells per well in 24 well plates in the appropriate media. Adenovirus was added in OptiMEM at 10,000 viral particles/cell, 1 ml per well in triplicate and incubated for 24 hrs at 37° C. Cells were then washed twice in PBS, trypsinised, triplicate wells pooled, spun down at 1200 rpm for 5 min and resuspended in 3000 PBS before analysis by FACS. Where cell viability was to be measured, 10 µl 7-amino-actinomycin D (7AAD; Sigma, Poole, Dorset) was added just prior to analysis. Cells were pooled from three separate transduction experiments for the calculation of results.

(d) Maturation and Phenotyping of Day 6 Immature Dendritic Cells Following Transduction with Retargeted Adenovirus Day 6 immature dendritic cells were infected with retargeted Ad or Ad5 at 100,000 particles per cell in complete medium for 24 hours, with *E. coli* 026:B6 lipopolysaccharide (LPS) added following 3 hours incubation at a concentration of 50 ng/ml. As controls, dendritic cells were either incubated in complete medium for 24 hours or matured by the addition of LPS in complete medium for 24 hours, In all samples IL-4 and GM-CSF were present in the complete medium at 25 ng/ml and 100 ng/ml respectively. Cells were then phenotyped by staining as follows: a minimum of 5×10⁴ cells in a volume of less than 2 ml medium were added to the recommended amount of antibody and incubated for 20 min on ice. 2 ml of ice-cold PBS was added before centrifugation at 300×g for 5 min at 4° C. The supernatant was flicked off and the pellet resuspended in 300 µl ice cold PBS. Cells from each sample were stained with antibodies to HLA-DR, CD40, CD80, CD83, CD86 and isotype matched control antibodies. Where cell viability was also measured, 10 ml of 7AAD was added immediately prior to analysis. Cells were analysed by flow cytometry using a Epics XL (Beckman Coulter, High Wycombe, UK.) and the EXPO32 analysis software (Beckman Coulter).

Results

Adenoviral Transductions

The poor dendritic cell DC infectivity of Ad5 vectors has been shown to be due to lack of the Ad5 fibre receptor (CAR) on the cell surface. In order to redirect the fibre protein to bind dendritic cells, the SHVKNLS or APSNSTA peptide was were genetically inserted into the HI loop of a modified Ad5 fibre protein. This fibre was also 'detargeted' by the inclusion of a double point mutation (KO1) that has been previously shown to block CAR binding. The infectivity of GFP-marked Ad5 vector particles pseudotyped with the resulting fibres was compared with that of virus with an unmodified Ad5 fibre, or with a fibre containing the KO1 mutation alone.

Figure 13:
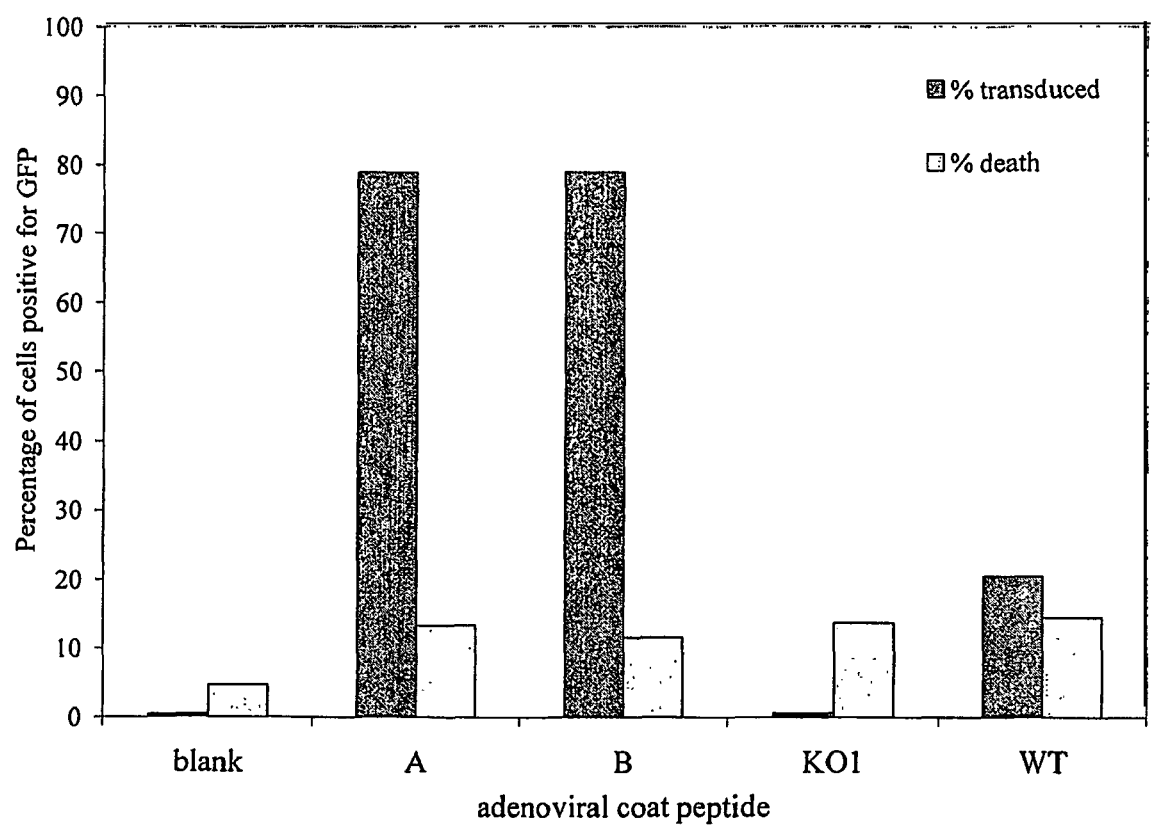
FIG. 13 shows transfection of day 6 human monocyte-derived immature dendritic cells with adenovirus retargeted by incorporating peptide A (columns A) or peptide B (columns B) in the HI region of the fibre protein in the capsid, with a KO1 fibre protein in the capsid (columns KO1), and with wild-type fibre protein in the capsid (columns WT), with a blank as control. The darker shaded columns show % transduction, the lighter shaded columns show % cell death.

Gene transfer of retargeted EGFP-reporter gene-bearing adenoviral constructs to immature dendritic cells from two different donors at 100,000 viral particles/cell in complete medium was measured by FACS. In both donors, retargeting the adenovirus with either peptide A or peptide B produced a transduction efficiency of between 64% and 79%, for example, 78.9%, both being of similar efficiencies, and both transducing a significantly higher percentage of cells compared with adenovirus with a wild type fibre protein in the capsid, between 43 and 46% positive, a KO1 fibre protein, between 0.7% and 1.4%, for example, 0.7%, see Table 6 and FIG. 13.

No significant toxicity was seen in any transduction, with cell death being measured at between 5 and 15% with no differences between viruses.

TABLE 6

Transduction of human monocyte-derived immature dendritic cells

| Donor | Wild type | KO1 | Irrelevant | A | B |
|---|---|---|---|---|---|
| A | 46.0 | 1.4 | 12.2 | 64.2 | 65.1 |
|   | (5.7) | (6.8) | (9.4) | (12.0) | (6.6) |
| B | 43.1 | 0.7 | 20.5 | 78.9 | 78.9 |
|   | (12.1) | (13.7) | (14.5) | (13.3) | (11.6) |

Percentage cell death shown in brackets

Transduction of human primary macrophages at 10,000 viral particles/cell in 2.5% serum also demonstrated that incorporating either peptide A (67.6% cells transduced) or peptide B (34.6% of cells transduced) into the viral coat significantly increased the efficiency of transduction above that seen with virus bearing a wild type fibre protein (13.3%) or KO1 fibre protein (9.2% cells transduced), see Table 7.

TABLE 7

Transduction of human monocyte-derived primary macrophages

|  | Wild type | KO1 | Irrelevant | A | B |
|---|---|---|---|---|---|
| Primary human macrophages | 13.3 | 9.2 | N/D | 67.6 | 34.6 |

In all other cell types, when virus was added at 10,000 particles per cell in OptiMEM, virus bearing peptide A or peptide B resulted in significantly higher transduction efficiency than virus bearing wild type fibre protein, KO1 fibre protein or fibre protein bearing an irrelevant peptide, see Table 8.

TABLE 8

Transduction of other cell types

| | VIRUS | | | |
|---|---|---|---|---|
| | KO1 | WT | SHVKLNS [SEQ. ID. NO.:29] | APSNSTA [SEQ. ID. NO.:15] |
| HUMAN CELLS | | | | |
| Macrophages | 9.2 | 13.3 | 67.6 | 34.6 |
| 1HAEo- | 2.0 | 45.8 | 82.9 | 79.0 |
| Cdc-HMEC-1 | 2.7 | 73.3 | 95.7 | 94.2 |
| HepG2 | 1.7 | 63.8 | 88.5 | 79.7 |
| MURINE CELLS | | | | |
| DCs | 1.5 | 13.5 | 71.7 | 54.1 |
| Sca1 + ve stem cells | 0.6 | 2.2 | 5.4 | 5.4 |
| Neuro-2A | 1.4 | 24.3 | 63.5 | 53.7 |

In Neuro-2A (N2a) cells, virus bearing peptide A produced 63.5% transduced cells, peptide B 53.7%, whilst wild type produced 24.3, KO1 1.4% and irrelevant peptide 1.3%.

In HAEo- cells, peptide A produced 82.9% transduced cells, peptide B 79%, whereas wild type fibre bearing virus transduced 45.8%, KO1 virus 2% and virus bearing an irrelevant peptide 3.2%.

The same patterns of transduction efficiencies were seen with HMEC cells (peptide A 95.7%, peptide B 94.2%, wild type 73.3, KO1 2.7% and irrelevant 25.1%) and HepG2 cells (peptide A 88.5%, peptide B 79.7%, wild type 63.8%, KO1 1.7% and irrelevant 9.7%).

Transduction of Murine Cells.

Incorporation of either peptide SHVKLNS [SEQ. ID. NO.: 29] or APSNSTA [SEQ. ID. NO.:15] into the adenoviral HI loop increased transduction efficiency of primary mouse dendritic cells to 71.7% and 54.1% respectively, a level considerably better than achieved with wild-type Ad5 (13.5%) (see Table 6). A much lower transduction efficiency of mouse Sca1-positive stem cells was achieved with all adenovirus samples, with SHVKLNS [SEQ. ID. NO.:29] or APSNSTA [SEQ. ID. NO.:15] retargeted adenovirus providing the best transduction efficiency of 5.4%, Ad5 virus transducing 2.2% and KO1 0.6%. Murine neuroblastoma cells (Neuro-2A) were also transduced more efficiently than with the wild-type virus, producing 63.5% and 53.7% GFP-positive cells with SHVKLNS [SEQ. ID. NO.:29] and APSNSTA [SEQ. ID. NO.:15] retargeted virus respectively compared to 24% with wild-type virus.

Maturation of Dendritic Cells

The ability of dendritic cells to mature in response to LPS was measured in virally transduced and untransduced samples by studying five maturation markers; HLA-DR, CD40, CD83 and the costimulatory molecules CD80 and CD86. Levels of all five markers (as assayed by flow cytometry) increased on maturation of untransduced cells by LPS, see Table 9.

TABLE 9

Effect of adenoviral transduction on ability of dendritic cells to mature in response to LPS

| | Cells | | | | |
|---|---|---|---|---|---|
| Antibody | Immature % | LPS Matured % | Transduced (SHVKLNS) [SEQ ID NO:29] % | Transduced (APSNSTA) [SEQ ID NO:15] % | Transduced Ad5 wild-type % |
| HLA-DR | 34 | 96.8 | 58.1 | 72.9 | 93.8 |
| CD40 | 0.5 | 30.2 | 15.6 | 9.8 | 26.4 |
| CD80 | 7.2 | 9.2 | 16.5 | 10.7 | 33.2 |
| CD83 | 2.4 | 48.7 | 24.6 | 18.0 | 69.9 |
| CD86 | 40.1 | 95.4 | 98.4 | 96.7 | 96.6 |

Figure 14:
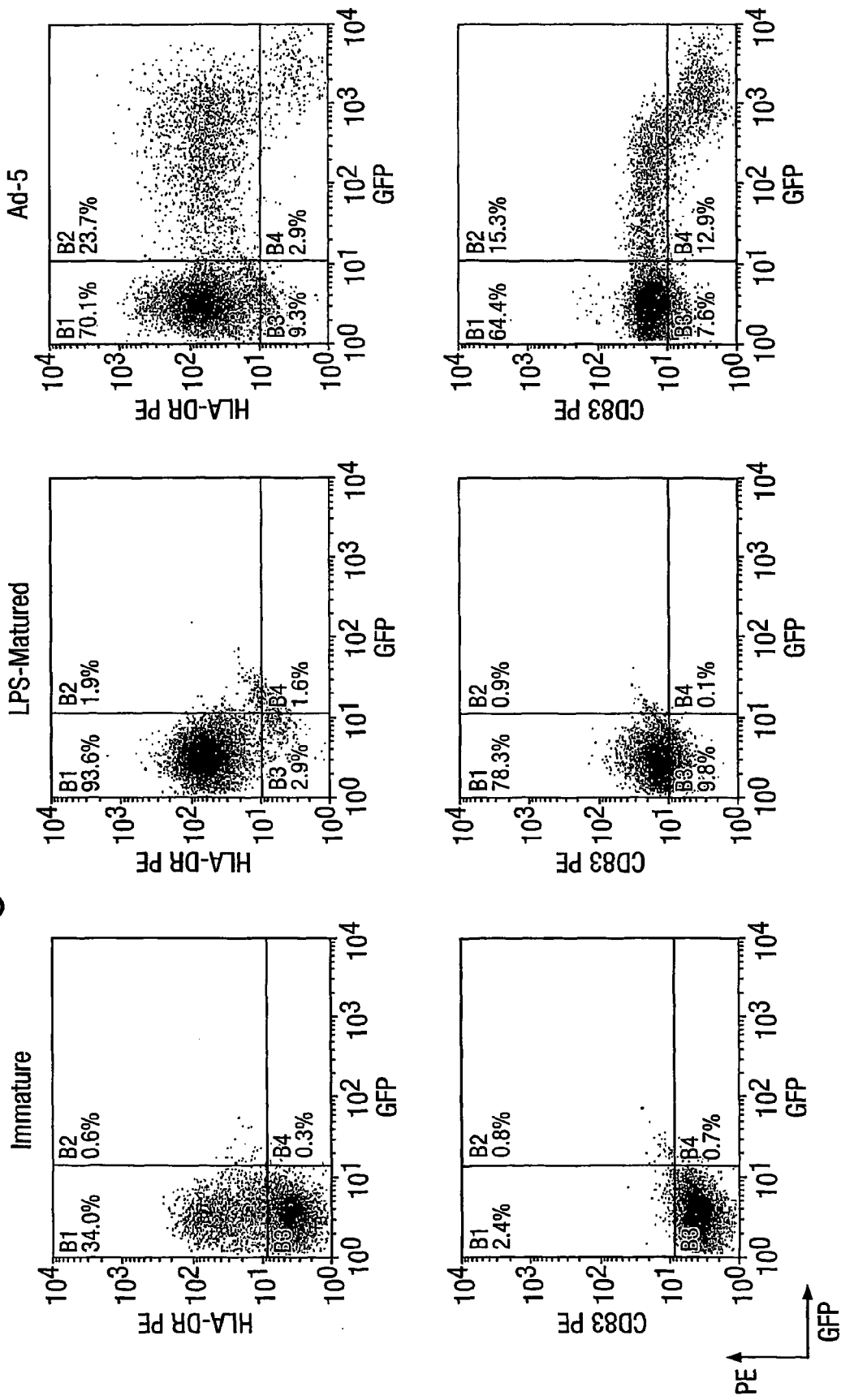
FIG. 14 shows the effect of adenoviral transduction on the ability of day 6 dendritic cells to mature in response to LPS. Immature dendritic cells were infected with wild type AD5 or with AD5 retargeted with peptide SHBKLNS or peptide APSNSTA. LPS was added following three hours incubation. The upper row shows HLA-DR, the lower row shows CD83. Results shown are pooled cells from three separate transductions and were reproducible with dendritic cells from other donors.
Figure 14:
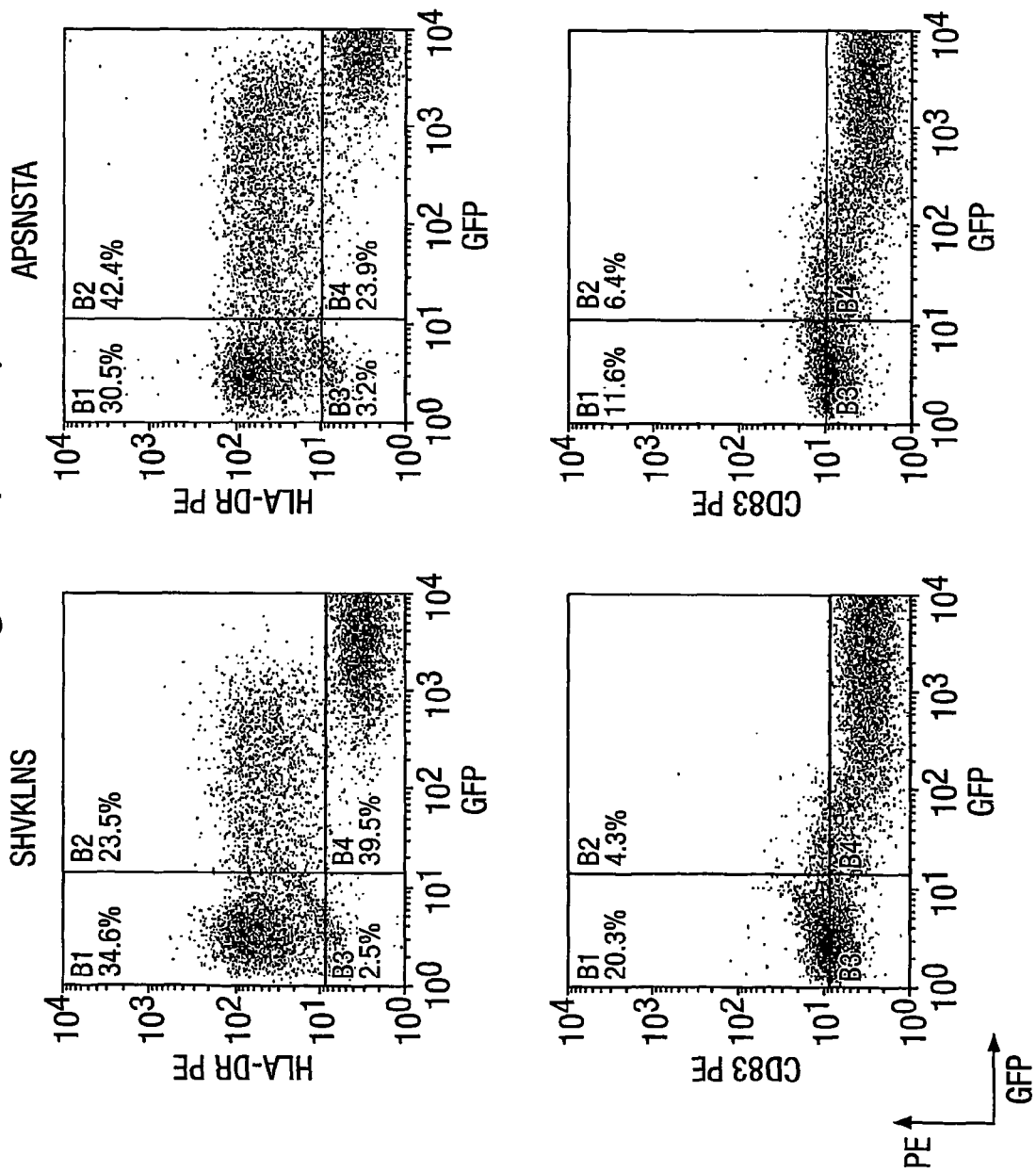

Adenovirus transduced cells did not show the same increase in the markers in response to LPS as untransduced cells. Although levels of CD86 increased in all LPS-treated cells, regardless of viral infection, induction of HLA-DR, CD40, CD80, and CD83 was reduced in cells transduced with retargeted adenovirus relative to those infected with the wild-type virus (Table 6). In the case of CD40, few (0.5%) of immature dendritic cells displayed detectable levels but this increased to 30.2% in untransduced LPS-matured dendritic cells and a similar level of maturation was seen in cells transduced with wild type virus (26.4%). However, the level of CD40 on the dendritic cells transduced with the retargeted virus was well below that induced following transduction with the wild type virus (15.6% for SHVKLNS [SEQ. ID. NO.:29] and 9.8% for APSNSTA [SEQ. ID. NO.:15]). This pattern where peptide retargeted virus results in lower levels of maturation markers on dendritic cells in response to LPS compared to wild type virus was also seen with HLA-DR, CD80 and CD83. The flow cytometry plots for HLA-DR and CD83 staining show that maturation occurs in virally infected cells expressing up to a maximum threshold of EGFP, over which maturation appears to be inhibited, see FIG. 14. It should be noted that this effect is also seen with wild type virus where EGFP expression exceeds the threshold, but is more pronounced in samples infected with the retargeted adenovirus possibly due to the higher number of cells transduced and expressing EGFP.

Example 4

Peptide Sequence Analysis by BLAST

The peptides APSNSTA [SEQ. ID. NO.:15] and SHVKLNS [SEQ. ID. NO.:29] were investigated for similarities to known ligands by BLAST sequence analysis of the two targeting peptides. Table 10 shows proteins found to have homology to peptide APSNSTA [SEQ. ID. NO.:15]. In Table 10 residues shown in bold and highlighted denote identity, residues shown in italic denote similarity.

TABLE 10

Proteins found by BLAST searches to have homology to peptide APSNSTA

| PEPTIDE | HOMOL-OGY | PROTEIN | SPECIES | LIGAND OF PROTEIN |
|---|---|---|---|---|
| APSNSTA [SEQ. ID. NO.:15] | PSNST [SEQ. ID. NO.:8] | Envelope glyco-protein gp120 | HIV I | CD4 |
| | | VP1 | Human echovirus 7 | ecay accelerating factor (DAF; CD55) |
| | AP*

Tillman, B. W., de Gruijl, T. D., Luykx-de Bakker, S. A., Scheper, R. J., Pinedo, H. M., Curiel, T. J., Gerritsen, W. R. and Curiel, D. T. (1999). Maturation of dendritic cells accompanies high-efficiency gene transfer by a CD40-targeted adenoviral vector. *J Immunol* 162, 6378-83.

Wade-Martins, R., Saeki, Y. and Antonio Chiocca, E. (2003). Infectious delivery of a 135-kb LDLR genomic locus leads to regulated complementation of low-density lipoprotein receptor deficiency in human cells. *Molecular Therapy* 7, 604-612.

Watkins, S. J., Mesyanzhinov, V. V., Kurochkina, L. P. and Hawkins, R. E. (1997). The 'adenobody' approach to viral targeting: specific and enhanced adenoviral gene delivery. *Gene Therapy* 4, 1004-12.

Wickham, T. J., Haskard, D., Segal, D. and Kovesdi, I. (1997). Targeting endothelium for gene therapy via receptors up-regulated during angiogenesis and inflammation. *Cancer Immunol Immunother* 45, 149-51.

Woolf, T. M., Chase, J. M. and Stinchcomb, D. T. (1995). Toward the therapeutic editing of mutated RNA sequences. *PNAS* 92, 8298-8302.

Yant, S. R., Meuse, L., Chiu, W., Ivies, Z., Izsvak, Z. and Kay, M. A. (2000). Somatic integration and long-term transgene expression in normal and haemophilic mice using a DNA transposon system. *Nat Genet.* 25, 35-41.

Yoon, K., Cole-Strauss, A. and Kmiec, E. B. (1996). Targeted gene correction of episomal DNA in mammalian cells mediated by a chimeric RNA.DNA oligonucleotide. *PNAS* 93, 2071-2076.

---

SEQUENCE LISTING

```
<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(4)
<223> OTHER INFORMATION: Xaa at position 2 = any amino acid residue, Xaa
      at position 3 = any amino acid residue, Xaa at position 4 = any
      amino acid residue

<400> SEQUENCE: 1

Pro Xaa Xaa Xaa Thr
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (3)..(3)
<223> OTHER INFORMATION: Xaa at position 3 = any amino acid residue

<400> SEQUENCE: 2

Pro Ser Xaa Ser
1

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(4)
<223> OTHER INFORMATION: Xaa at position 2 = any amino acid, Xaa at
      position 3 = any amino acid having an amide side chain, Xaa at
      position 4 = any amino acid

<400> SEQUENCE: 3

Gln Xaa Xaa Xaa Gln
1               5

<210> SEQ ID NO 4
```

```
<211> LENGTH: 3
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(2)
<223> OTHER INFORMATION: Xaa at position 2 = any amino acid residue
      having an aliphatic side chain

<400> SEQUENCE: 4

Ser Xaa Ser
1

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(2)
<223> OTHER INFORMATION: Xaa at position 2 = any amino acid residue
<220> FEATURE:
<221> NAME/KEY: MISC_FEATURE
<222> LOCATION: (4)..(4)
<223> OTHER INFORMATION: Xaa at position 4 = any amino acid residue

<400> SEQUENCE: 5

Pro Xaa Leu Xaa Thr
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide binding to dendritic cells

<400> SEQUENCE: 6

Pro Ala Leu Lys Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(2)
<223> OTHER INFORMATION: Xaa at position 2 = any amino acid residue
<220> FEATURE:
<221> NAME/KEY: MISC_FEATURE
<222> LOCATION: (4)..(4)
<223> OTHER INFORMATION: Xaa at position 4 = any amino acid residue

<400> SEQUENCE: 7

Pro Xaa Asn Xaa Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide binding to dendritic cells
```

```
<400> SEQUENCE: 8

Pro Ser Asn Ser Thr
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide binding to dendritic cells

<400> SEQUENCE: 9

Pro Pro Asn Thr Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(4)
<223> OTHER INFORMATION: Xaa at position 2 = any amino acid residue, Xaa
      at position 3 = any amino acid residue, Xaa at position 4 = any
      amino acid residue
<220> FEATURE:
<221> NAME/KEY: MISC_FEATURE
<222> LOCATION: (6)..(6)
<223> OTHER INFORMATION: Xaa at position 6 = any amino acid resdue
<220> FEATURE:
<221> NAME/KEY: MISC_FEATURE
<222> LOCATION: (6)..(6)
<223> OTHER INFORMATION: Xaa at position 6 = any amino acid residue

<400> SEQUENCE: 10

Pro Xaa Xaa Xaa Thr Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(2)
<223> OTHER INFORMATION: Xaa at position 2 = any amino acid residue
<220> FEATURE:
<221> NAME/KEY: MISC_FEATURE
<222> LOCATION: (4)..(4)
<223> OTHER INFORMATION: Xaa at position 4 = any amino acid residue
<220> FEATURE:
<221> NAME/KEY: MISC_FEATURE
<222> LOCATION: (6)..(6)
<223> OTHER INFORMATION: Xaa at position 6 = any amino acid residue

<400> SEQUENCE: 11

Pro Xaa Leu Xaa Thr Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
```

```
<222> LOCATION: (2)..(2)
<223> OTHER INFORMATION: Xaa at position 2 = any amino acid residue
<220> FEATURE:
<221> NAME/KEY: MISC_FEATURE
<222> LOCATION: (4)..(4)
<223> OTHER INFORMATION: Xaa at position 4 = any amino acid residue
<220> FEATURE:
<221> NAME/KEY: MISC_FEATURE
<222> LOCATION: (6)..(6)
<223> OTHER INFORMATION: Xaa at position 6 = any amino acid residue

<400> SEQUENCE: 12

Pro Xaa Asn Xaa Thr Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (1)..(1)
<223> OTHER INFORMATION: Xaa at position 1 = any amino acid residue
<220> FEATURE:
<221> NAME/KEY: MISC_FEATURE
<222> LOCATION: (3)..(5)
<223> OTHER INFORMATION: Xaa at position 3 = any amino acid residue, Xaa
      at position 4 = any amino acid residue, Xaa at position 5 = any
      amino acid residue

<400> SEQUENCE: 13

Xaa Pro Xaa Xaa Xaa Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (1)..(1)
<223> OTHER INFORMATION: Xaa at position 1 = any amino acid residue
<220> FEATURE:
<221> NAME/KEY: MISC_FEATURE
<222> LOCATION: (3)..(5)
<223> OTHER INFORMATION: Xaa at position 3 = any amino acid residue, Xaa
      at position 4 = any amino acid residue, Xaa at position 5 = any
      amino acid residue
<220> FEATURE:
<221> NAME/KEY: MISC_FEATURE
<222> LOCATION: (7)..(7)
<223> OTHER INFORMATION: Xaa at position 7 = any amino acid residue

<400> SEQUENCE: 14

Xaa Pro Xaa Xaa Xaa Thr Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 15

Ala Pro Ser Asn Ser Thr Ala
1               5
```

```
<210> SEQ ID NO 16
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 16

Ser Pro Ala Leu Lys Thr Val
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 17

Ser Thr Pro Pro Asn Thr Thr
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide binding to dendritic cells

<400> SEQUENCE: 18

Pro Ser Asn Ser
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide binding to dendritic cells

<400> SEQUENCE: 19

Pro Ser Leu Ser
1

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (1)..(1)
<223> OTHER INFORMATION: Xaa at position 1 = Ala or Lys
<220> FEATURE:
<221> NAME/KEY: MISC_FEATURE
<222> LOCATION: (4)..(4)
<223> OTHER INFORMATION: Xaa at position 4 = any amino acid residue

<400> SEQUENCE: 20

Xaa Pro Ser Xaa Ser
1               5

<210> SEQ ID NO 21
<211> LENGTH: 5
<212> TYPE: PRT
<213> ORGANISM: Artificial Sequence
<220> FEATURE:
```

-continued

<223> OTHER INFORMATION: Synthetic peptide binding to dendritic cells

<400> SEQUENCE: 21

Ala Pro Ser Asn Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide binding to dendritic cells

<400> SEQUENCE: 22

Leu Pro Ser Leu Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide binding to dendritic cells

<400> SEQUENCE: 23

Met Leu Pro Ser Leu Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 24

Pro Met Leu Pro Ser Leu Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 25

Ser Gln Lys Asn Pro Gln Met
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 26

Phe Gln Ser Gln Tyr Gln Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 27

Met Ala Ser Ile Ser Met Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 28

Asp Trp Trp His Thr Ser Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 29

Ser His Val Lys Leu Asn Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 30

Gln Leu Leu Thr Gly Ala Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 31

Thr Ala Arg Asp Tyr Arg Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 32

Phe Pro Arg Ala Pro His His
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide binding to dendritic cells

```
<400> SEQUENCE: 33

Ser Glu Trp Leu Ser Ala Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 34

Ile Gly Gly Ile Arg Arg His
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 35

Tyr Thr Met Glu Phe Asn Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide binding to dendritic cells

<400> SEQUENCE: 36

Pro Ala Ala Tyr Lys Ala His
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(4)
<223> OTHER INFORMATION: Xaa at position 2 = any amino acid residue, Xaa
      at position 3 = any amino acid residue, Xaa at position 4 = any
      amino acid residue
<220> FEATURE:
<221> NAME/KEY: MISC_FEATURE
<222> LOCATION: (6)..(6)
<223> OTHER INFORMATION: Xaa at position 6 = Ala or Val

<400> SEQUENCE: 37

Pro Xaa Xaa Xaa Thr Xaa
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(2)
<223> OTHER INFORMATION: Xaa at position 2 = any amino acid residue,
<220> FEATURE:
```

```
<221> NAME/KEY: MISC_FEATURE
<222> LOCATION: (4)..(4)
<223> OTHER INFORMATION: Xaa at position 4 = any amino acid residue,

<400> SEQUENCE: 38

Pro Xaa Asn Xaa Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(4)
<223> OTHER INFORMATION: Xaa at position 2 = any amino acid residue, Xaa
      at position 3 = Asn or Leu, Xaa at position 4 = any amino acid
      residue

<400> SEQUENCE: 39

Pro Xaa Xaa Xaa Thr
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (2)..(2)
<223> OTHER INFORMATION: Xaa at position 2 = any amino acid residue
<220> FEATURE:
<221> NAME/KEY: MISC_FEATURE
<222> LOCATION: (4)..(4)
<223> OTHER INFORMATION: Xaa at position  = Thr or Ser
<220> FEATURE:
<221> NAME/KEY: MISC_FEATURE
<222> LOCATION: (4)..(4)
<223> OTHER INFORMATION: Xaa at position  4 = Thr or Ser

<400> SEQUENCE: 40

Pro Xaa Asn Xaa Thr
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide binding to dendritic cells
<220> FEATURE:
<221> NAME/KEY: MISC_FEATURE
<222> LOCATION: (1)..(1)
<223> OTHER INFORMATION: Xaa at position 1 = Ala or Leu
<220> FEATURE:
<221> NAME/KEY: MISC_FEATURE
<222> LOCATION: (4)..(4)
<223> OTHER INFORMATION: Xaa at position 4 = any amino acid residue

<400> SEQUENCE: 41

Xaa Pro Ser Xaa Ser
1               5

<210> SEQ ID NO 42
<211> LENGTH: 5
<212> TYPE: PRT
<213> ORGANISM: Artificial Sequence
```

```
<220> FEATURE:
<223> OTHER INFORMATION: Synthetic peptide binding to dendritic cells
<220> FEATURE:
<221> NAME/KEY: MISC_FEATUR Lys Lys Lys Lys Lys Lys Lys Lys Lys Lys Lys Lys Lys Lys Lys
1               5                   10                  15

Gly Ala Cys Met Ala Ser Ile Ser Met Lys Cys Gly
            20                  25

<210> SEQ ID NO 47
<211> LENGTH: 28
<212> TYPE: PRT
<213> ORGANISM: Artificial Sequence
<220> FEATURE:
<223> OTHER INFORMATION: Peptide derivative of the invention

<400> SEQUENCE: 47

Lys Lys Lys Lys Lys Lys Lys Lys Lys Lys Lys Lys Lys Lys Lys
1               5                   10                  15

Gly Ala Cys Phe Pro Arg Ala Pro His His Cys Gly
            20                  25

<210> SEQ ID NO 48
<211> LENGTH: 28
<212> TYPE: PRT
<213> ORGANISM: Artificial Sequence
<220> FEATURE:
<223> OTHER INFORMATION: Peptide derivative of the invention

<400> SEQUENCE: 48

Lys Lys Lys Lys Lys Lys Lys Lys Lys Lys Lys Lys Lys Lys Lys
1               5                   10                  15

Gly Ala Cys Asp Trp Trp His Thr Ser Ala Cys Gly
            20                  25

<210> SEQ ID NO 49
<211> LENGTH: 28
<212> TYPE: PRT
<213> ORGANISM: Artificial Sequence
<220> FEATURE:
<223> OTHER INFORMATION: Peptide derivative of the invention

<400> SEQUENCE: 49

Lys Lys Lys Lys Lys Lys Lys Lys Lys Lys Lys Lys Lys Lys Lys
1               5                   10                  15

Gly Ala Cys Arg Arg Glu Thr Ala Trp Ala Cys Gly
            20                  25

<210> SEQ ID NO 50
<211> LENGTH: 28
<212> TYPE: PRT
<213> ORGANISM: Artificial Sequence
<220> FEATURE:
<223> OTHER INFORMATION: Peptide derivative of the invention

<400> SEQUENCE: 50

Lys Lys Lys Lys Lys Lys Lys Lys Lys Lys Lys Lys Lys Lys Lys
1               5                   10                  15

Gly Ala Cys Ala Thr Arg Trp Ala Arg Glu Cys Gly
            20                  25

<210> SEQ ID NO 51
<211> LENGTH: 27
<212> TYPE: PRT
<213> ORGANISM: Artificial Sequence
<220> FEATURE:
<223> OTHER INFORMATION: Peptide derivative of the invention

<400> SEQUENCE: 51

```
Lys Lys Lys Lys Lys Lys Lys Lys Lys Lys Lys Lys Lys Lys Lys
1               5                   10                  15

Gly Ala Cys Arg Arg Glu Glu Trp Ala Cys Gly
            20                  25
```

<210> SEQ ID NO 52
<211> LENGTH: 28
<212> TYPE: PRT
<213> ORGANISM: Artificial Sequence
<220> FEATURE:
<223> OTHER INFORMATION: Peptide derivative of the invention

<400> SEQUENCE: 52

```
Lys Lys Lys Lys Lys Lys Lys Lys Lys Lys Lys Lys Lys Lys Lys
1               5                   10                  15

Gly Ala Cys Met Ala Ser Ile Ser Met Lys Cys Gln
            20                  25
```

<210> SEQ ID NO 53
<211> LENGTH: 7
<212> TYPE: PRT
<213> ORGANISM: Artificial Sequence
<220> FEATURE:
<223> OTHER INFORMATION: integrin-binding peptide

<400> SEQUENCE: 53

```
Arg Arg Glu Thr Glu Trp Ala
1               5
```

<210> SEQ ID NO 54
<211> LENGTH: 16
<212> TYPE: PRT
<213> ORGANISM: Artificial Sequence
<220> FEATURE:
<223> OTHER INFORMATION: synthetic nucleic acid binding domain

<400> SEQUENCE: 54

```
Lys Lys Lys Lys Lys Lys Lys Lys Lys Lys Lys Lys Lys Lys Lys Lys
1               5                   10                  15
```

<210> SEQ ID NO 55
<211> LENGTH: 5
<212> TYPE: PRT
<213> ORGANISM: Artificial Sequence
<220> FEATURE:
<223> OTHER INFORMATION: hydrophobic spacer sequence
<220> FEATURE:
<221> NAME/KEY: MISC_FEATURE
<222> LOCATION: (1)..(1)
<223> OTHER INFORMATION: x = epsilon-amino hexanoic acid residue
<220> FEATURE:
<221> NAME/KEY: MISC_FEATURE
<222> LOCATION: (3)..(3)
<223> OTHER INFORMATION: x = epsilon-amino hexanoic acid residue

<400> SEQUENCE: 55

```
Xaa Ser Xaa Gly Ala
1               5
```

<210> SEQ ID NO 56
<211> LENGTH: 17
<212> TYPE: DNA
<213> ORGANISM: Artificial Sequence
<220> FEATURE:
<223> OTHER INFORMATION: Primer

<400> SEQUENCE: 56
ccctcattag cgtaacg                                                    17

<210> SEQ ID NO 57
<211> LENGTH: 7
<212> TYPE: PRT
<213> ORGANISM: Artificial Sequence
<220> FEATURE:
<223> OTHER INFORMATION: control peptide

<400> SEQUENCE: 57

Ala Thr Arg Trp Ala Arg Glu
1               5

<210> SEQ ID NO 58
<211> LENGTH: 24
<212> TYPE: DNA
<213> ORGANISM: Artificial Sequence
<220> FEATURE:
<223> OTHER INFORMATION: Oligonucleotide encoding peptide ligand

<400> SEQUENCE: 58
ccggaagcca cgtcaagctg aacg                                            24

<210> SEQ ID NO 59
<211> LENGTH: 27
<212> TYPE: DNA
<213> ORGANISM: Artificial Sequence
<220> FEATURE:
<223> OTHER INFORMATION: complementary oligonucleotide encoding SEQ ID
      NO:29

<400> SEQUENCE: 59
ccggcgctgt tcagcttcac gtggctt                                         27

<210> SEQ ID NO 60
<211> LENGTH: 7
<212> TYPE: PRT
<213> ORGANISM: Artificial Sequence
<220> FEATURE:
<223> OTHER INFORMATION: Peptide ligand

<400> SEQUENCE: 60

Ala Pro Thr Asn Ala Thr Ala
1               5

<210> SEQ ID NO 61
<211> LENGTH: 26
<212> TYPE: DNA
<213> ORGANISM: Artificial Sequence
<220> FEATURE:
<223> OTHER INFORMATION: oligonucleotide encoding peptide ligand

<400> SEQUENCE: 61
ccggagcccc cagcaacagc accgcc                                          26

<210> SEQ ID NO 62
<211> LENGTH: 27
<212> TYPE: DNA
<213> ORGANISM: Artificial Sequence
<220> FEATURE:
<223> OTHER INFORMATION: complementary oligonucleotide encoding SEQ ID
      NO:15

<400> SEQUENCE: 62
ccggcggcgg tgctgttgct gggggct                                         27

The invention claimed is:

1. An isolated polypeptide comprising a sequence selected from the group consisting of PPNTT (SEQ ID NO: 9), STPPNTT (SEQ ID NO: 17), APSNSTA(SEQ ID NO: 15), and SPALKTV (SEQ ID NO: 16), wherein the length of the polypeptide is up to 30 amino acids, the polypeptide is capable of binding to dendritic cells, and the polypeptide is not a full-length naturally-occurring protein.

2. A peptide selected from the group consisting of PALKT (SEQ ID NO: 6), PSNST (SEQ ID NO: 8), PPNTT (SEQ ID NO: 9), STPPNTT (SEQ ID NO: 17), APSNSTA (SEQ ID NO: 15), and SPALKTV (SEQ ID NO: 16), and wherein the peptide is linked to a polycationic nucleic acid-binding component.

3. The peptide according to claim 2, wherein the peptide is linked to the polycationic nucleic acid binding component via a spacer element.

4. A non-viral transfection mixture comprising:
(i) a lipid component,
(ii) a polycationic nucleic acid-binding component, and
(iii) the peptide PALKT (SEQ ID NO: 6) or a peptide with a length up to 30 amino acids comprising an amino acid sequence selected from the group consisting of PSNST (SEQ ID NO: 8), PPNTT (SEQ ID NO: 9), STPPNTT (SEQ ID NO: 17), APSNSTA (SEQ ID NO: 15), and SPALKTV (SEQ ID NO: 16).

5. The mixture according to claim 4, wherein the lipid component comprises one or more lipids selected from the group consisting of cationic lipids, lipids having membrane destabilising properties, and lipids having fusogenic properties.

6. A non-viral transfection complex comprising:
(i) a nucleic acid,
(ii) a lipid component,
(iii) a polycationic nucleic acid-binding component, and
(iv) the peptide PALKT (SEQ ID NO: 6) or a peptide with a length up to 30 amino acids comprising an amino acid sequence selected from the group consisting of PSNST (SEQ ID NO: 8), PPNTT (SEQ ID NO: 9), STPPNTT (SEQ ID NO: 17), APSNSTA (SEQ ID NO: 15), and SPALKTV (SEQ ID NO: 16).

7. A process for the production of a complex according to claim 6, which comprises admixing components (i), (ii), (iii) and (iv) in the following order: lipid component, peptide, polycationic nucleic acid binding component, and nucleic acid.

8. A non-viral transfection complex comprising:
(i) a nucleic acid,
(ii) a polycationic nucleic acid-binding component, and
(iii) the peptide PALKT (SEQ ID NO: 6) or a peptide with a length up to 30 amino acids comprising an amino acid sequence selected from the group consisting of PSNST (SEQ ID NO: 8), PPNTT (SEQ ID NO: 9), STPPNTT (SEQ ID NO: 17), APSNSTA (SEQ ID NO: 15), and SPALKTV (SEQ ID NO: 16).

9. A method of transfecting a cell with a nucleic acid, which method comprises contacting the cell in vitro or in vivo with the transfection complex according to claim 6 or claim 8.

10. A composition comprising the transfection complex according to claim 6 or claim 8, said composition being in admixture or conjunction with a pharmaceutically suitable carrier.

11. A method for expressing a gene in a human or in a non-human animal with a defect and/or a deficiency in a gene, which method comprises administering the transfection complex according to claim 6 or claim 8 to the human or to the non-human animal.

12. A method for inducing an immune response in a human or a non-human animal, which method comprises administering the transfection complex according to claim 6 or claim 8 to the human or to the non-human animal.

13. A method of inhibiting the expression of a gene, which comprises administering the transfection complex according to claim 6 or claim 8 to a human or to a non-human animal.

14. A kit comprising:
(i) a nucleic acid,
(ii) a polycationic nucleic acid-binding component, and
(iii) the peptide PALKT (SEQ ID NO: 6) or a peptide with a length up to 30 amino acids comprising an amino acid sequence selected from the group consisting of PSNST (SEQ ID NO: 8), PPNTT (SEQ ID NO: 9), STPPNTT (SEQ ID NO: 17), APSNSTA (SEQ ID NO: 15), and SPALKTV (SEQ ID NO: 16), and, optionally,
(iv) a lipid component.

15. The peptide according to claim 1, wherein the peptide consists of the amino acid sequence APSNSTA [SEQ ID NO: 15].

* * * * *